(12) United States Patent
Lavis et al.

(10) Patent No.: US 11,958,976 B2
(45) Date of Patent: Apr. 16, 2024

(54) PHOTOACTIVE FLUOROPHORES AND METHODS OF IN VIVO LABELING

(71) Applicant: HOWARD HUGHES MEDICAL INSTITUTE, Chevy Chase, MD (US)

(72) Inventors: Luke D. Lavis, Ashburn, VA (US); Jonathan B. Grimm, Ashburn, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 0 days.

(21) Appl. No.: 17/975,310

(22) Filed: Oct. 27, 2022

(65) Prior Publication Data

US 2023/0095090 A1    Mar. 30, 2023

Related U.S. Application Data

(62) Division of application No. 16/087,864, filed as application No. PCT/US2017/033842 on May 22, 2017, now abandoned.

(60) Provisional application No. 62/339,643, filed on May 20, 2016.

(51) Int. Cl.
| | | |
|---|---|---|
| *C07D 405/12* | (2006.01) | |
| *C07D 311/80* | (2006.01) | |
| *C07D 313/14* | (2006.01) | |
| *C07D 473/32* | (2006.01) | |
| *C07D 493/10* | (2006.01) | |
| *C07F 7/08* | (2006.01) | |
| *C09B 11/24* | (2006.01) | |
| *C09B 11/28* | (2006.01) | |
| *G01N 21/64* | (2006.01) | |

(52) U.S. Cl.
CPC ............ *C09B 11/24* (2013.01); *C07D 311/80* (2013.01); *C07D 313/14* (2013.01); *C07D 405/12* (2013.01); *C07D 473/32* (2013.01); *C07D 493/10* (2013.01); *C07F 7/0816* (2013.01); *C09B 11/28* (2013.01); *G01N 21/6458* (2013.01); *G01N 2021/6439* (2013.01)

(58) Field of Classification Search
CPC . C07D 205/04; C07F 7/0816; G01N 21/6458; G01N 2021/6439
See application file for complete search history.

*Primary Examiner* — Joseph R Kosack
*Assistant Examiner* — Karen Cheng
(74) *Attorney, Agent, or Firm* — Stites & Harbison, PLLC; Mandy Wilson Decker

(57) ABSTRACT

Provided are a photoactive fluorophore, a photoactive ligand, and a photoactive complex. The photoactive fluorophore includes a photoactivatable derivative of an azetidine-containing Janelia-Fluor dye. The photoactive ligand includes a photoactive fluorophore and a protein tag. The photoactive complex includes a photoactive ligand conjugated to a protein. Also provided are methods of in vivo labeling with and photoactivation of the photoactive fluorophore, ligand, and complex.

7 Claims, 40 Drawing Sheets

6: R = HaloTag ligand
7: R = SNAP-tag ligand

HaloTag ligand

SNAP-tag ligand

18: R = HaloTag ligand
19: R = SNAP-tag ligand

12

13

14

15

PHOTOACTIVE FLUOROPHORES AND METHODS OF IN VIVO LABELING

RELATED APPLICATIONS

This application is a division of U.S. patent application Ser. No. 16/087,864, which entered the national stage from International Patent Application No. PCT/US17/33842 filed May 22, 2017, which claims priority from U.S. Provisional Application Ser. No. 62/339,643 filed May 20, 2016, the entire disclosures of which are incorporated herein by this reference.

TECHNICAL FIELD

The presently-disclosed subject matter generally relates to photoactive fluorophores and methods of in vivo labeling. More specifically, the presently-disclosed subject matter relates to small molecule photoactive fluorophores, methods of in vivo labeling with small molecule photoactive fluorophores, and methods of photo activation of fluorescent compounds in vivo.

BACKGROUND

Small molecule fluorophores are important tools for advanced imaging experiments. These fluorophores, which are brighter than fluorescent proteins, are a crucial element of modern microscopy methods. Recently, the development of new protein-specific labeling strategies, such as the self-labeling tag concept pioneered by Johnsson, has enabled the formation of fluorescent bioconjugates inside living cells: membrane-permeable synthetic dye "ligands" that passively diffuse into cells where they form covalent bonds with their cognate protein "tag." This type of self-labeling tag combines genetic encoding—one of the main advantages of fluorescent proteins—with the favorable photophysics of organic fluorophores.

Building upon these sophisticated attachment techniques, the instant inventors recently reported that incorporation of four-membered azetidine rings could substantially improve the brightness and photostability of small, cell-permeable fluorophores. These "Janelia Fluor" (JF) dyes are excellent labels for live-cell imaging, especially in single-molecule tracking experiments where they enable longer observations and better localization of individual fluorescent conjugates. However, most caging groups are large and hydrophobic, which diminishes solubility and reactivity with self-labeling tag proteins. Moreover, classic photocaging strategies are incompatible with fully N-alkylated rhodamine dyes such as $JF_{549}$ and $JF_{646}$.

Although Hell and coworkers have discovered a caging strategy in which treatment of rhodamine dyes with oxalyl chloride and diazomethane generates a spirocyclic diazoketone that is colorless and nonfluorescent, this strategy has not been applied to dyes with cyclic amine substituents. Additionally, while the resulting diazoketone-caged dyes have been employed as antibody labels for fixed cell imaging, they have not been incorporated into self-labeling tag systems nor have they been used in live-cells. Accordingly, there remains a need for photoactivatable (PA) versions of JF dyes that are compatible with existing live-cell labeling strategies and maintain the superior brightness of the JF dyes.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature (s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter is directed to a photoactive fluorophore. In some embodiments, the photoactive fluorophore includes a photoactivatable derivative of an azetidine-containing Janelia-Fluor dye. In some embodiments, the photoactive fluorophore is decarboxylated by photoinduction.

In some embodiments, the presently-disclosed subject matter is directed to a method of forming a photoactive fluorophore. In some embodiments, the method includes caging a Janelia-Fluor dye. In some embodiments, caging the Janelia-Fluor dye includes adding oxalyl chloride to a solution of the Janelia-Fluor dye to form a first mixture, adding triethylamine and (trimethylsilyl)diazomethane in succession to the first mixture to form a second mixture, concentrating the second mixture to form a concentrate, and purifying the concentrate to prove the photoactive fluorophore. In some embodiments, the caged Janelia-Fluor dye includes a Si-rhodamine.

In some embodiments, the presently-disclosed subject matter is directed to a photoactive ligand comprising a photoactive fluorophore and a protein tag. In some embodiments, the photoactive fluorophore comprises a photoactivatable derivative of an azetidine-containing Janelia-Fluor dye. Suitable protein tags include, but are not limited to, a HaloTag ligand, a SNAP-tag ligand, any other suitable protein tag, or a combination thereof. In some embodiments, conjugation of the photoactive ligand to a cognate protein increases light absorption of the photoactive ligand after photolysis. In some embodiments, a brightness of the photoactive fluorophore is substantially similar to the brightness of a parent fluorophore from which the photoactive fluorophore is derived.

In some embodiments, the presently disclosed subject matter is directed to a photoactive complex comprising a photoactive ligand conjugated to a protein. In some embodiments, the photoactive ligand is conjugated to the protein in vivo. In some embodiments, the photoactive ligand comprises a photoactive fluorophore and a protein tag. In some embodiments, the photoactive fluorophore is arranged and disposed to decarboxylate upon photoinduction. In some embodiments, the photoactive fluorophore is arranged and disposed to form a methyl-Janelia-Fluor compound upon decarboxylation. In some embodiments, the photoactive fluorophore is arranged and disposed to provide increased fluorescence upon decarboxylation.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1A:
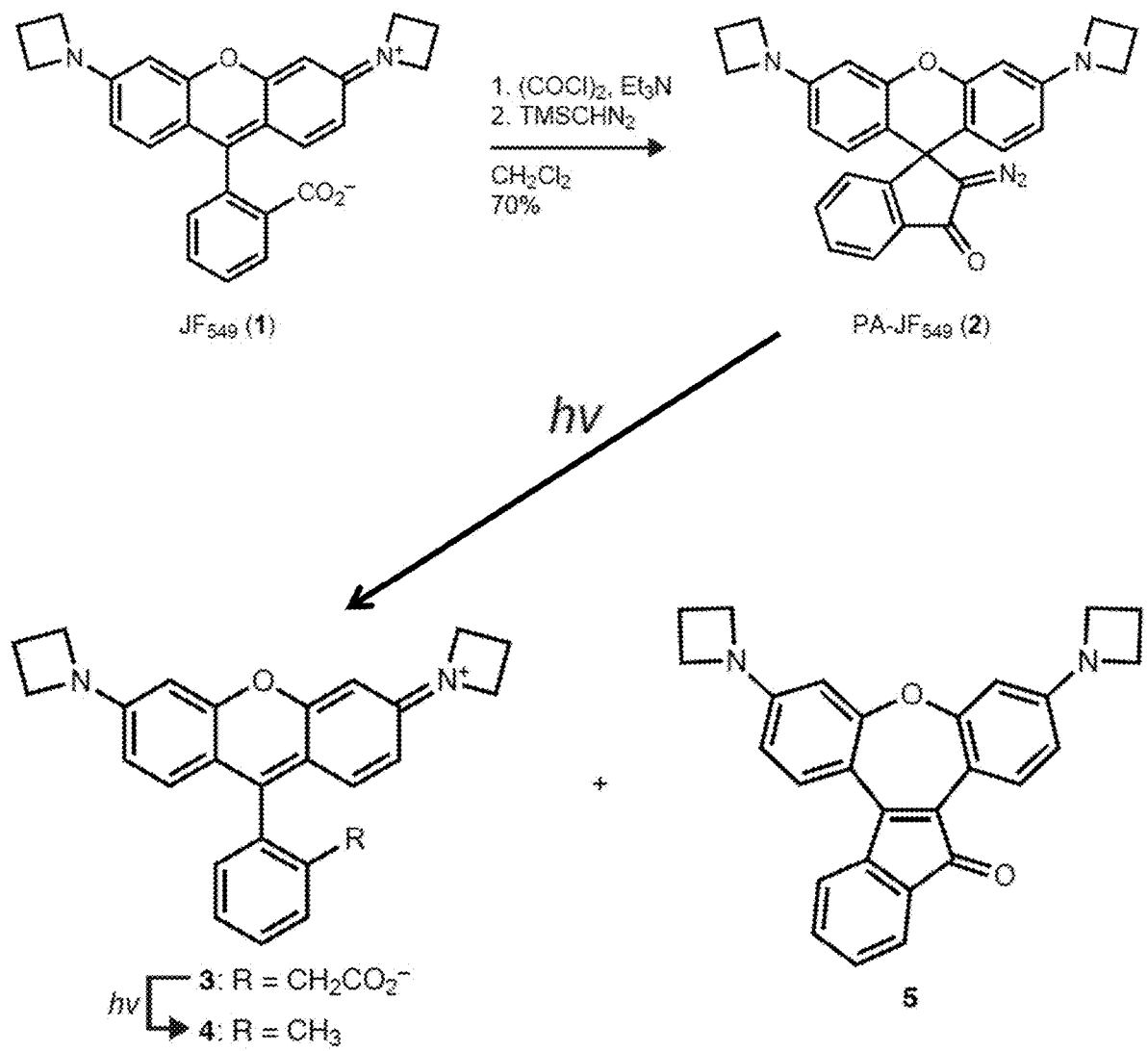
FIGS. 1A-I show graphs and images illustrating synthesis, characterization, and utility of photoactivatable Janelia Fluor 549 (PA-JF$_{549}$). (A) Synthesis and photochemistry of PA-JF$_{549}$. Treatment of JF$_{549}$ (1) with oxalyl chloride and TMS diazomethane yields PA-JF$_{549}$ (2). Photoactivation (365 nm) yields only a trace amount of the expected phenylacetic acid derivative (3) with methyl-substituted JF$_{549}$ (4) as the major product (50%) and the inadone 5 as the minor (10%) product. (B) Normalized absorption (abs) and fluorescence emission (fl) of 1, 3, and 4. (C) Chemical structure of PA-JF$_{549}$-HaloTag ligand (6) and PA-JF$_{549}$-SNAP-tag ligand (7). (D) Image of cumulative single-particle tracks of HaloTag-Sox2 labeled with PA-JF$_{549}$ ligand 6, scale bar: 5 µm. (E) Histogram of detected photons/particle/frame when performing sptPALM of Sox2 using the 6-HaloTag fusion (magenta, median=120.7 photons) or mEos3.2 fusion (black, median=70.9 photons) under identical imaging conditions. (F) Histogram of track length when performing sptPALM of Sox2 using the 6-HaloTag fusion (magenta, mean=0.20 s) or mEos3.2 fusion (black, mean=0.07 s) under identical imaging conditions. (G) PALM image of U2OS cell expressing TOMM20-HaloTag and labeled with PA-JF$_{549}$ ligand 6; The 268,561 detected molecules are displayed according to their localization full-width at half-maximum; scale bar: 2 µm. (H) Histogram of detected photons/localization/frame when performing PALM of TOMM20 using the 6-HaloTag fusion (magenta, median=636.6 photons) or mEos3.2 fusion (black, median=266.8 photons) under identical imaging conditions. (I) Histogram of calculated localization precision when performing PALM of TOMM20 using the 6-HaloTag fusion (magenta, median=13.5 nm) or mEos3.2 fusion (black, median=20.2 nm) under identical imaging conditions.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes photoactive fluorophores and methods of in vivo labeling. More specifically, the presently-disclosed subject matter relates to small molecule photoactive fluorophores, methods of in vivo labeling with small molecule photoactive fluorophores, and methods of photo activation of fluorescent compounds in vivo.

In some embodiments, the photoactive fluorophores include photoactivatable derivatives of one or more fluorophores. The photoactivatable derivates are formed from any suitable fluorophore, such as, but not limited to, fluorophores containing one or more cyclic amine substituents. For example, in one embodiment, the photoactive fluorophores include photoactivatable derivatives of an azetidine-containing "Janelia-Fluor" (JF) dye. In another embodiment, these JF dyes include four-membered azetidine rings in place of the ubiquitous dimethylamino groups of existing fluorophores, forming small, cell-permeable fluorophores having increased brightness and photostability.

As illustrated below, in some embodiments, the photoactive fluorophore includes photoactivatable Janelia-Fluor 549 (PA-JF$_{549}$), photoactivatable Janelia-Fluor 646 (PA-JF$_{646}$), or any other suitable photoactivatable Janelia Fluor. These photoactivatable derivatives retain the brightness and photostability of the JF dyes once activated, providing increased brightness as compared to existing fluorescent proteins. Additionally, the facile photoactivation of these compounds provides improved single-particle tracking and facile localization microscopy experiments. Furthermore, a cell-permeability of the PA-JF compounds facilitates in vivo imaging.

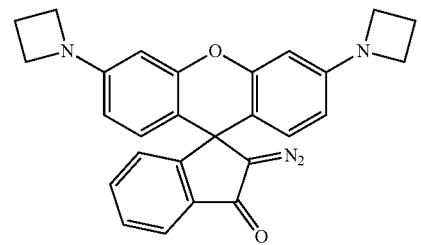

PA-JF$_{549}$

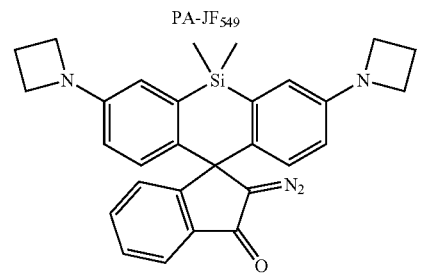

PA-JF$_{646}$

In some embodiments, a method of forming the photoactive fluorophores includes a caging strategy involving treatment of the JF dyes with oxalyl chloride and diazomethane. For example, in one embodiment, the method of forming the photoactive fluorophore includes adding oxalyl chloride to a solution of the JF dye and stirring the reaction at room temperature. Next, triethylamine and (trimethylsilyl)diazomethane are added in succession and the reaction is stirred at room temperature, concentrated, and then purified. The concentration and purification include any suitable concentration and purification method, such as, but not limited to, concentration in vacuo, flash chromatography on silica gel, or a combination thereof.

In contrast to the expected phenylacetic acid derivative, the photochemistry of the photoactive fluorophores described herein unexpectedly provides methyl-JF as the major photoproduct (50%). Without wishing to be bound by theory, it is believed that the methyl-JF is produced by photoinduced decarboxylation of the initial photochemical product (i.e., the expected phenylacetic acid derivative). In some embodiments, the methyl-JF produced by the PA-JF compound maintains the brightness of the parent JF dye. In some embodiments, the brightness is substantially similar to the brightness of the parent. In some embodiments, at least about 60, 65, 70, 75, 80, 85, 90, or 95% of the brightness is maintained.

In some embodiments, the PA-JF compound is joined with a protein tag, such as HaloTag, SNAP tag, or any other suitable protein tag, to form a PA-JF-protein tag ligand. For example, as shown below, the PA-JF-protein tag ligand may include, but is not limited to, PA-JF$_{549}$-HaloTag ligand, PA-JF$_{549}$-SNAP-tag ligand, PA-JF$_{646}$-HaloTag ligand, and/or PA-JF$_{646}$-SNAP-tag ligand shown below.

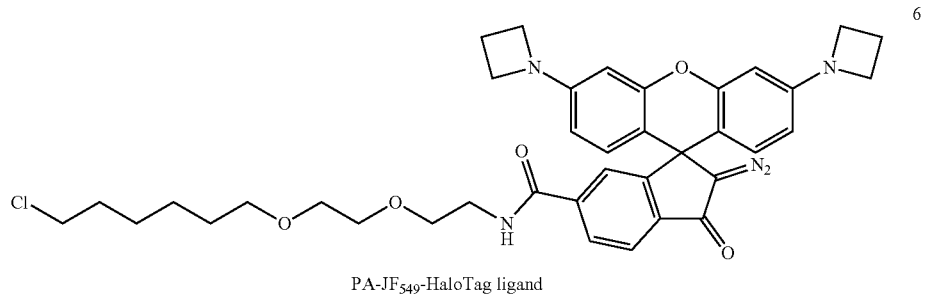

PA-JF$_{549}$-HaloTag ligand

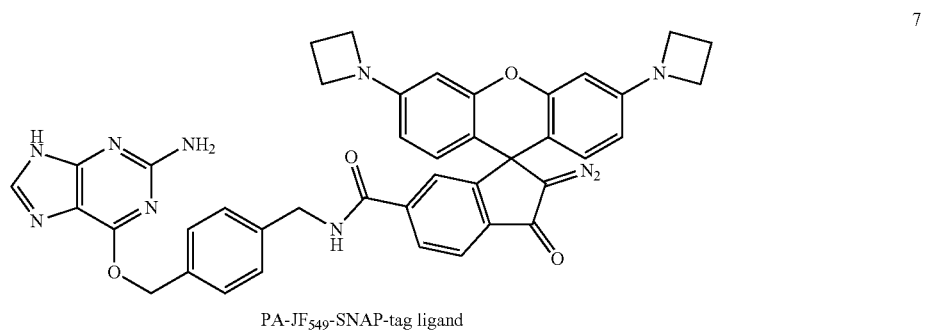

PA-JF$_{549}$-SNAP-tag ligand

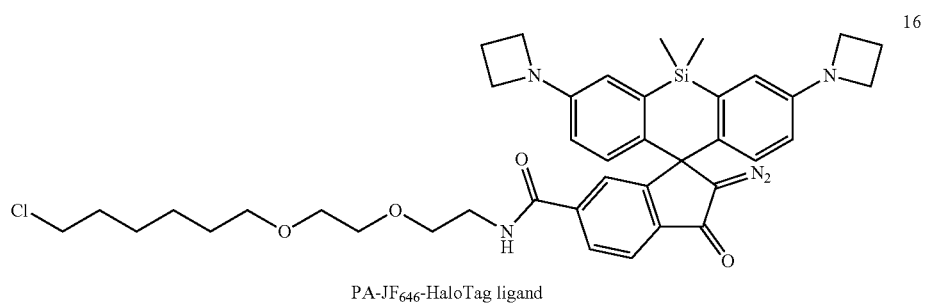

PA-JF$_{646}$-HaloTag ligand

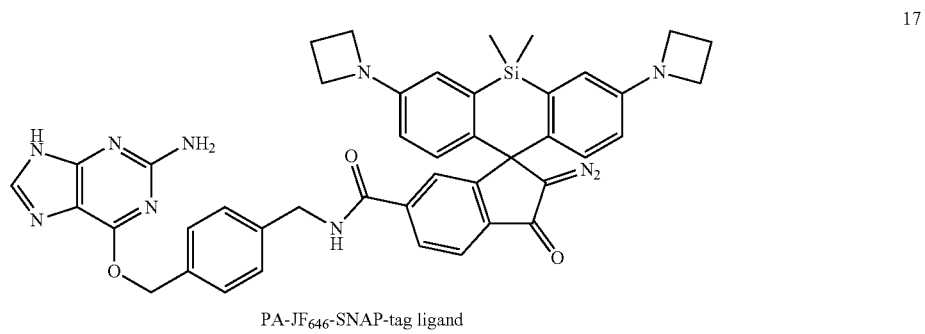

PA-JF$_{646}$-SNAP-tag ligand

In some embodiments, a method of forming the PA-JF-protein tag ligand includes forming a 6-Methoxycarbonyl-JF compound of the desired JF, converting the 6-Methoxycarbonyl-JF compound to a photoactivatable 6-Methoxycarbonyl-JF compound (6-Methoxycarbonyl-PA-JF), converting the 6-Methoxycarbonyl-PA-JF compound to a PA-JF-N-hydroxysuccinimide compound (PA-JF-NHS), and then converting the PA-JF-NHS compound into the PA-JF-protein tag ligand.

In one embodiment, forming the 6-Methoxycarbonyl-JF compound includes charging a vial with a starting compound, $Pd_2dba_3$, XPhos, and $Cs_2CO_3$, sealing the vial, and evacuating/backfilling the vial with nitrogen. Next, dioxane is added to the vial and the reaction is flushed with nitrogen. Azetidine is then added to the vial and the reaction is stirred at an elevated temperature, such as, but not limited to, 100° C. After stirring the reaction at the elevated temperature, the composition is cooled to room temperature, diluted with MeOH, deposited onto a filter aid (e.g., Celite), concentrated to dryness, and then purified to provide the 6-Methoxycarbonyl-JF compound. As will be appreciated by those skilled in the art, the starting compound will vary depending upon the PA-JF-protein tag ligand being formed. For example, the starting compound for the PA-$JF_{549}$-protein tag ligand may include 3',6'-Dibromo-6-methoxycarbonylfluoran, while the starting compound for the PA-$JF_{646}$-protein tag ligand may include 6-Methoxycarbonylsilafluorescein ditriflate.

Following the formation of the 6-Methoxycarbonyl-JF compound, the converting of the 6-Methoxycarbonyl-JF compound to the 6-Methoxycarbonyl-PA-JF compound includes the caging method described in detail above. Next, converting the 6-Methoxycarbonyl-PA-JF compound to the PA-JF-NHS compound includes adding NaOH to a solution of the 6-Methoxycarbonyl-PA-JF compound in 2:1 MeOH/THF, under nitrogen, and stirring the reaction at room temperature. The reaction is then acidified, diluted, and extracted, such as, for example, with HCl, water, and $CH_2Cl_2$, respectively. After extraction, the organic extracts are dried, filtered, and concentrated to provide a carboxylic acid. The carboxylic acid is then combined with TSTU in DMF, DIEA is added, and the reaction is stirred at room temperature. Following the stirring, the reaction is concentrated to dryness, deposited onto a filter aid, and purified to provide the PA-JF-NHS compound.

The PA-JF-NHS is then converted to a desired PA-JF-protein tag ligand by any suitable method. For example, converting the PA-JF-NHS compound to a PA-JF-HaloTag ligand includes dissolving the PA-JF-NHS compound in DMF, adding a solution of HaloTag(O2)amine in DMF, subsequently adding DIEA, and then stirring the reaction at room temperature. After stirring, the reaction is concentrated to dryness and purified to provide the PA-JF-HaloTag ligand. In another example, converting the PA-JF-NHS compound to a PA-JF-SNAP-tag ligand includes combining the PA-JF-NHS compound with $BG-NH_2$ and DMF, subsequently adding DIEA, and then stirring the reaction at room temperature. After stirring, the reaction is concentrated to dryness and purified to provide the PA-JF-SNAP-tag ligand. While these method are described in more detail in the Examples below, as will be understood by those skilled in the art, modifications to the concentrations and/or reaction conditions are contemplated herein and are intended to be covered by the instant disclosure.

In some embodiments, conjugation of the PA-JF-protein tag ligand to the cognate protein provides a substantial increase in light absorption after photolysis as compared to the PA-JF-protein ligand in the absence of the cognate protein. For example, as compared to compounds in the absence of the cognate protein, the PA-$JF_{549}$-HaloTag ligand exhibited at least a two-fold increase in the photochemical efficiency to the desired fluorescent product when conjugated to the cognate HaloTag protein, while the PA-$JF_{646}$-HaloTag ligand exhibited at least a five-fold increase in the generation of the far-red absorbing product when conjugated to the cognate HaloTag protein. Accordingly, in some embodiments, conjugation of the PA-JF-protein ligand to a cognate protein influences the photochemical outcome of the reaction towards a desirable fluorescent form. Additionally or alternatively, in some embodiments, the PA-JF-protein ligands facilitate single-molecule tracking, super-resolution imaging, and/or in vivo imaging.

As the PA-JF-protein tag ligands are formed from cell permeable JF dyes, in some embodiments, the PA-JF-protein tag ligands facilitate in vivo imaging. For example, the PA-JF-protein tag ligand may enter one or more cells after being delivered to a subject, upon which the ligand binds to a desired protein. Subsequent photoinduction of the PA-JF-protein tag ligand conjugated to the desired protein provides increased fluorescence, which facilitates in vivo imaging. In some embodiments, more than one PA-JF-protein tag ligand may be used to provide multiple color and/or molecule imaging. For example, a first PA-JF-protein tag ligand may include a first PA-JF that exhibits a first color and a first protein tag that binds to a first protein, and a second PA-JF-protein tag ligand may include a second PA-JF that exhibits a second color and a second protein tag that binds to a second protein. Upon photoactivation, the first and second PA-JF-protein tag ligands will exhibit the first and second color, the first and second color corresponding to a location of the first and second protein, respectively.

EXAMPLES

Example 1

As recently described by the instant inventors, the formation of azetidine-containing "Janelia Fluor" (JF) dyes provides a general method for improving the brightness and photostability of small, cell-permeable fluorophores. In this example, the utility of the JF dyes is refined and extended through synthesis of photoactivatable derivatives that are compatible with established live-cell labeling strategies.

More specifically, this example describes photoactivatable (PA) versions of $JF_{549}$ and $JF_{646}$, demonstrates their compatibility with existing live-cell labeling strategies, and shows their utility in single-molecule tracking and super-resolution imaging. $JF_{549}$ and $JF_{646}$ are fully N-alkylated rhodamine dyes and cannot be caged using N-acylation with standard photolabile groups as can other rhodamine dyes. As such, in order to form the photoactivatable versions of $JF_{549}$ and $JF_{646}$, a caging strategy involving treatment of the JF dyes with oxalyl chloride and diazomethane was used.

As illustrated in FIG. 1A, to test the compatibility of this caging strategy with the azetidinyl Janelia Fluor dyes, the photoactivatable $JF_{549}$ (PA-$JF_{549}$) (2) was first prepared in good yield from $JF_{549}$ (1). The photochemistry of compound 2 was then evaluated in water; previous reports had only described the photolysis of diazoketone-caged dyes in methanol. Surprisingly, the major product from exhaustive photolysis of compound 1 in aqueous solution was not the expected phenylacetic acid dye (3) but rather the methyl-substituted $JF_{549}$ (4) along with the putative nonfluorescent "dark product" (5). Compound 4 was generated with an apparent photochemical quantum yield ($\Phi_{PC}$) value of 2.2%, similar to photoswitchable fluorescent proteins ($\Phi_{PC}\approx1\%$). Without wishing to be bound by theory, this unexpected product is believed to be the result of efficient ($\Phi_{PC}=15\%$) photoinduced decarboxylation of the initial photochemical product 3.

Figure 1B:
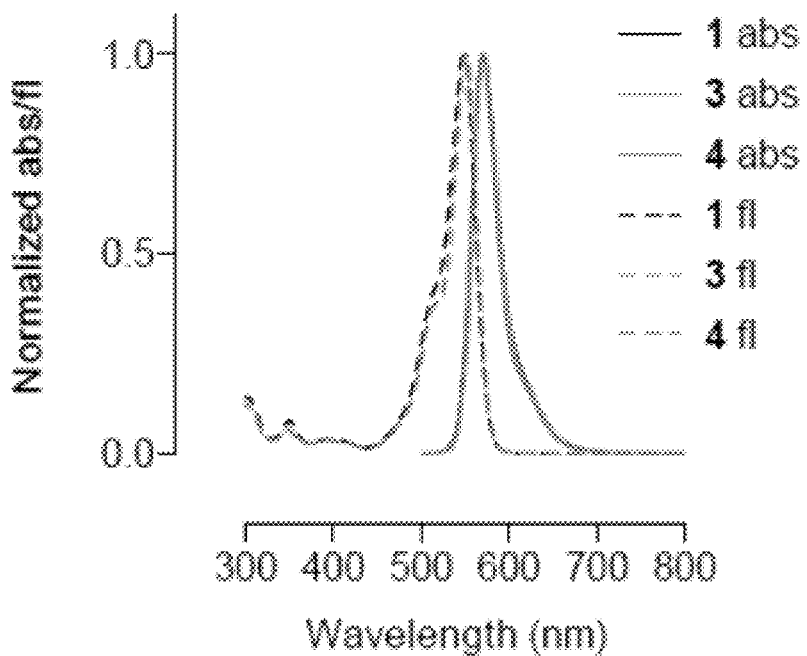

Nevertheless, as shown in FIG. 1B, the two photoproducts 3 and 4 are highly fluorescent molecules with similar spectral properties to compound 1, the parent JF$_{549}$. That is, these compounds retain the superior brightness of the JF dyes. As reported before, fluorophore 1 exhibits an absorption maximum ($\lambda_{max}$) of 549 nm, extinction coefficient ($\varepsilon$) of $1.01\times10^5$ M$^{-1}$ cm$^{-1}$, emission maximum ($\lambda_{em}$) of 571 nm, and a fluorescence quantum yield ($\Phi_F$) of 0.88. Fluorophore 3 showed $\lambda_{max}/\lambda_{em}=553$ nm/573 nm and retained 95% of the brightness of 1 ($\varepsilon=9.89\times10^4$ M$^{-1}$ cm$^{-1}$; $\Phi_F=0.85$) whereas dye 4 gave $\lambda_{max}\lambda_{em}=551$ nm/570 nm and retained 75% of the brightness of 1 ($\varepsilon=8.59\times10^4$ M$^{-1}$ cm$^{-1}$; $\Phi_F=0.78$). Additionally, the facile photoactivation of these compounds provides improved single-particle tracking and localization microscopy experiments.

Figure 1C:
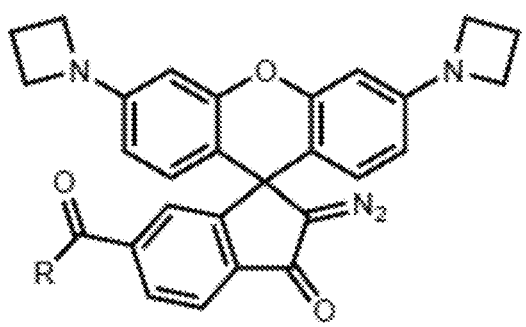
Figure 1C:
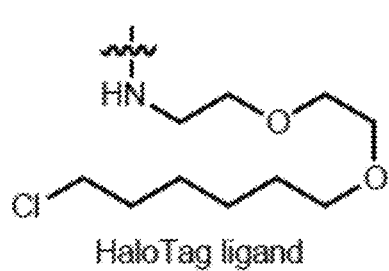
Figure 1C:
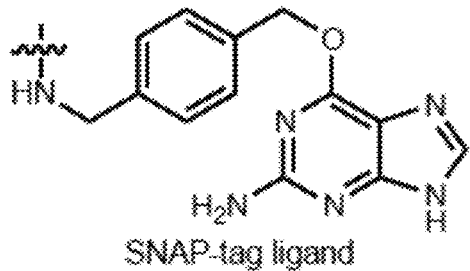
Figure 3A:
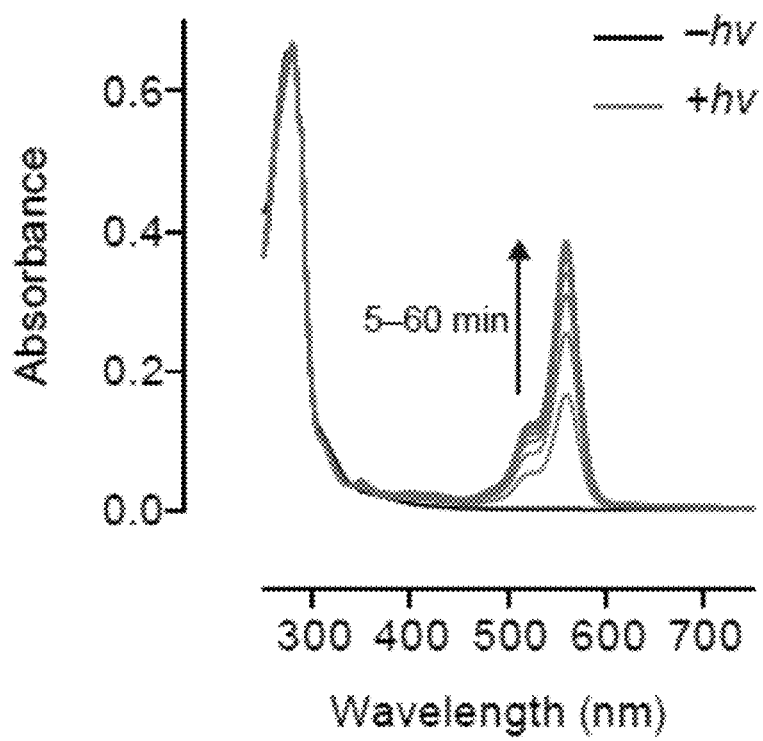
FIGS. 3A-V shows graphs and images illustrating properties and performance of photoactivatable Janelia Fluor 549 (PA-JF$_{549}$). (A) Absorbance spectrum of PA-JF$_{549}$-HaloTag ligand (6) bound to HaloTag protein before (−hv, black line) and after photoactivation (365 nm; +hv, magenta lines). (B) Structure of JF$_{549}$-HaloTag ligand (8) and TMR-HaloTag ligand (9). (C) Comparison of the absolute absorbance spectrum of 8 (5 µM) incubated with HaloTag protein (black) with the absorbance spectrum of 6 (5 µM) incubated with (magenta) or without (dashed magenta) HaloTag protein and then exhaustively photoactivated with 365 nm light. (D) Absorbance spectrum of PA-JF$_{549}$-SNAP-tag ligand (7) bound to HaloTag protein before (−hv, black line) and after photoactivation (365 nm; +hv, magenta lines). (E) Structure of JF$_{549}$-SNAP-tag ligand (10). (F) Comparison of the absolute absorbance spectrum of 10 (5 µM) incubated with SNAP-tag protein with the absorbance spectrum of 7 (5 µM) incubated with (magenta) or without (dashed magenta) SNAP-tag protein and then exhaustively photoactivated with 365 nm light. (G) Activation rates of histone H2B-HaloTag labeled with PA-JF$_{549}$-HaloTag ligand (6) or histone H2B-mEos3.2 in live U2OS cells under identical imaging conditions (n=5, shading shows±s.e.m.) overlaid with exponential fit (black). (H) Plot comparing the spontaneous activation of TOMM20-HaloTag labeled with PA-JF$_{549}$-HaloTag ligand (6; magenta) or TOMM20-mEos3.2 (black) in fixed U2OS cells in the absence of 405 nm activation light; solid lines show linear fits. (I) Histogram of detected photons/localization using TOMM20-HaloTag labeled with PA-JF$_{549}$-HaloTag ligand (6) or TOMM20-mEos3.2 in fixed U2OS cells. (J) Cartoon showing experimental workflow of spt-dSTORM experiment (top) and sptPALM experiment (bottom). ES cells expressing HaloTag-Sox2 were labeled to saturation with PA-JF$_{549}$-HaloTag ligand 6 or TMR-HaloTag ligand 8 and imaged on a multifocus microscope, which allows simultaneous imaging of 9 focal planes across an axial depth of ~4 µm. (K) Plot of the number of single molecule trajectories measured per frame in ES cell expressing HaloTag-Sox2 labeled with PA-JF$_{549}$ ligand 6 (sptPALM mode, magenta) or the commercial TMR-HaloTag ligand (9; spt-dSTORM mode, black); n=5 cells for each ligand; s.d. shown in gray. (L-M) Image of cumulative single-particle tracks imaged for frames 2000-2500 (between dashed lines in K; only trajectories observed in >5 successive frames shown); lower left: number of trajectories measured; lower right: scale bars: 2 µm. (L) Cell labeled with PA-JF$_{549}$ ligand 6 (1544 trajectories). (M) Cell labeled with standard TMR ligand 9 (191 trajectories). (N-O) Statistics from 3D tracking experiments (shown in J-M) in ES cells expressing HaloTag-Sox2 and labeled with 6 or 9. (N) Histogram of detected photons/particle/frame using labels 6 (magenta) or 9 (black). (O) Histogram of particle localization/frame using labels 6 (magenta) or 9 (black). (P) PALM image of fixed U2OS cells expressing TOMM20-mEos3.2 fusions. Scale-bar: 2 µm. The 195,422 detected molecules are displayed according to their localization full-width at half-maximum. The median calculated localization error was 20.2 nm. (Q) Zoom-in of PALM image of fixed U2OS cell expressing clathrin-HaloTag fusions and labeled with ligand 6. The full-chip image is composed of 1,048,575 drift-corrected localizations with a median localization error of 10.8 nm. The data shows the expected ring structure of clathrin; each subpanel is 1 µm². (R) PALM image of U2OS cell expressing ensconsin-HaloTag fusions and labeled with ligand 6. The image is composed of 445,242 localizations with a median calculated localization error of 28.7 nm. Scale-bar: 5 (S) PALM image of U2OS cell expressing Sec61β-HaloTag fusions and labeled with ligand 6. The image is composed of 29,356 localizations with a median calculated localization error of 20.9 nm. Scale bar: 5 µm. (T-V) Analysis of blinking behavior of PA-JF$_{549}$ during PALM of ensconsin-HaloTag shown in R. (T) Histogram of the duration of individual blinking events (magenta), overlaid with the fit to an exponential distribution (black). (U) Histogram of the duration of intervals between blinking events (magenta), overlaid with the fit to an exponential distribution (black). (V) Histogram of the number of blinking events per molecule (magenta), overlaid with the fit to a geometric distribution (black).
Figure 3B:
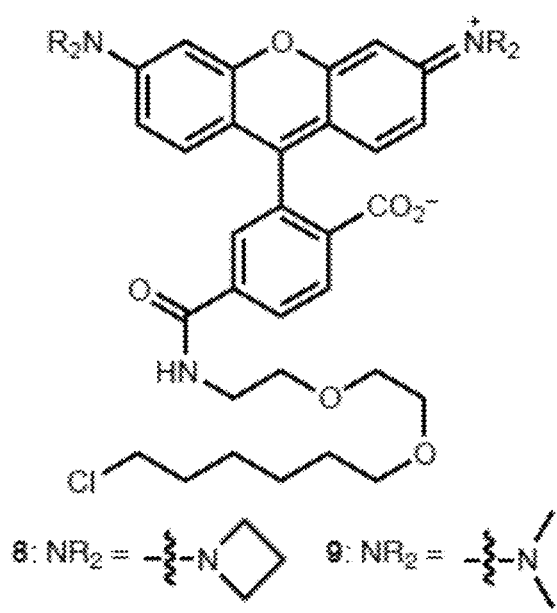
Figure 3C:
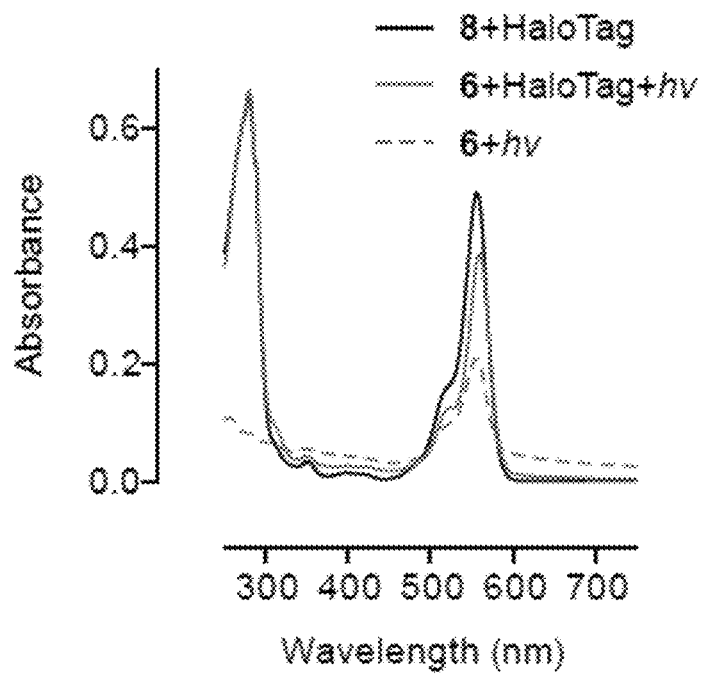
Figure 3D:
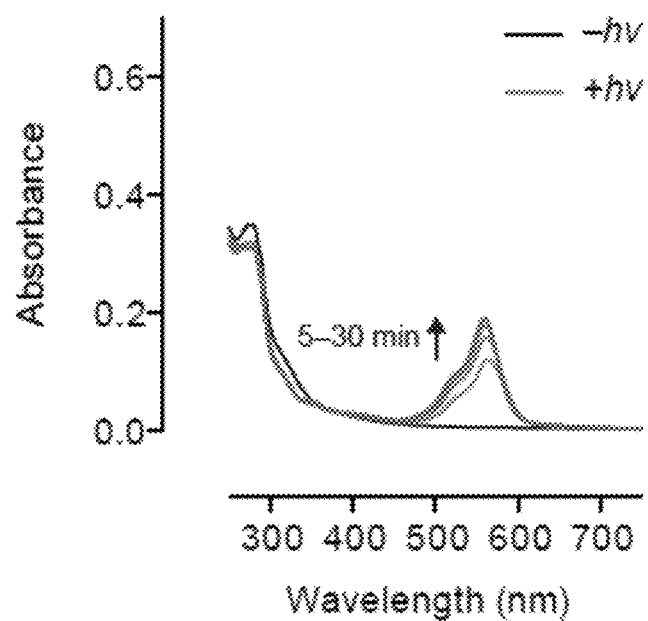
Figure 3E:
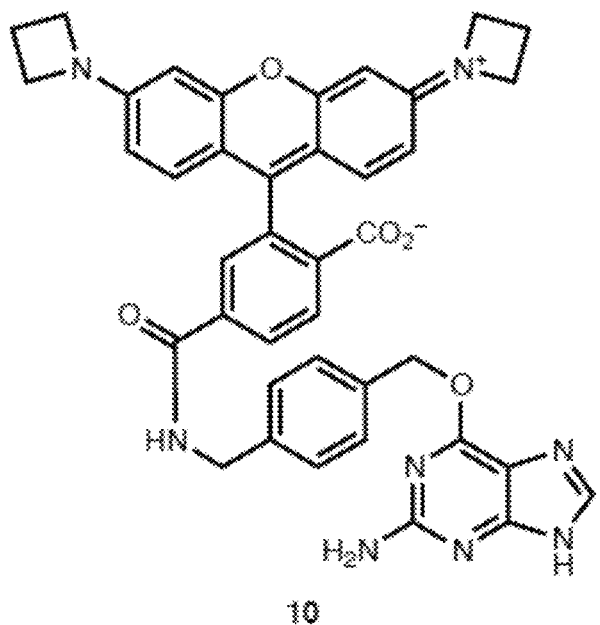
Figure 3F:
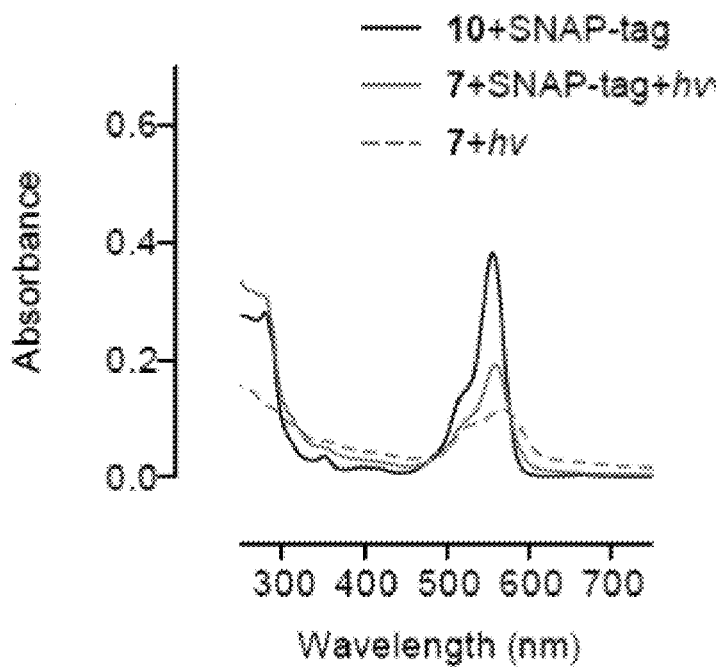

After measuring the brightness of the resulting photoactivated fluorophore, a HaloTag ligand of PA-JF$_{549}$ (6) was synthesized (FIG. 1C). Labeling of HaloTag protein with 6 either in vitro, in live cells, or in fixed cells gave conjugates with low background absorption and fluorescence that could be activated by one- or two-photon illumination (FIG. 3A). It was found that attachment of 6 to the HaloTag improves the yield of the desired fluorescent product compared to the free PA-JF$_{549}$ ligand (FIGS. 3B-C), which, without wishing to be bound by theory, is believed to be by restricting conformational flexibility and preventing the formation of the planar dark product 5 (FIG. 1A). Referring to FIGS. 3D-F, this enhancement in desired photochemical outcome upon conjugation to protein was also observed for the PA-JF$_{549}$-SNAP-tag ligand (7), the synthesis of which is shown in (FIG. 1C). Although advantageous, this improvement in photochemistry upon conjugation is not large enough to eliminate the need for washing out free ligand.

Figure 3G:
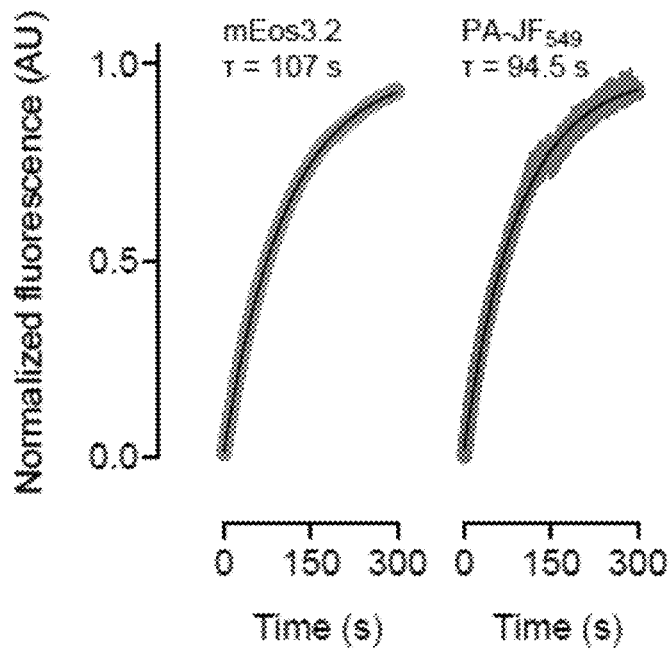
Figure 3H:
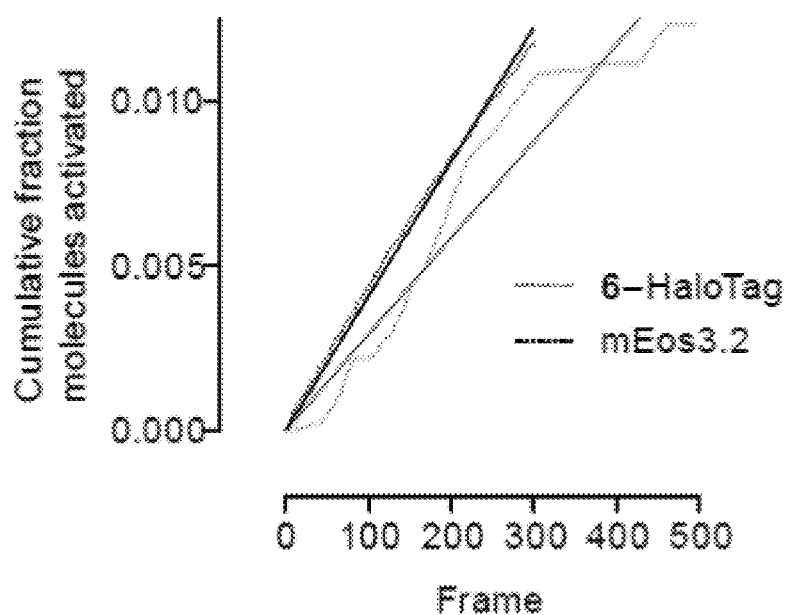

The performance of the PA-JF$_{549}$-HaloTag ligand (6) was directly compared to the genetically encoded mEos3.2. As illustrated in FIG. 3G, the activation rate of PA-JF$_{549}$ ($\tau=94.5$ s) was similar to mEos3.2 ($\tau=107$ s). Additionally, as shown in FIG. 3H and Table 1, the on-off activation ratios were also similar ($\sim10^{-5}$). However, the median number of detected photons/localization (FIG. 3I) was higher for PA-JF$_{549}$ compared to mEos3.2 (JF$_{549}$=870.9, mEos3.2=533.7).

TABLE 1

| On-off ratio of photoactivatable fluorophores | | | |
|---|---|---|---|
| Fluorophore | on-rate ($\times10^{-5}$ frames$^{-1}$) | off-rate (frames$^{-1}$) | on-off ratio ($\times10^{-5}$) |
| mEos3.2 | 4.5 ± 0.4 | 1.1 ± 0.1 | 4.2 ± 0.4 |
| PA-JF$_{549}$ | 8 ± 6 | 0.6 ± 0.1 | 10 ± 7 |
| PA-JF$_{646}$ | 0.18 ± 0.02 | 1.1 ± 0.2 | 0.16 ± 0.02 |

Figure 1D:
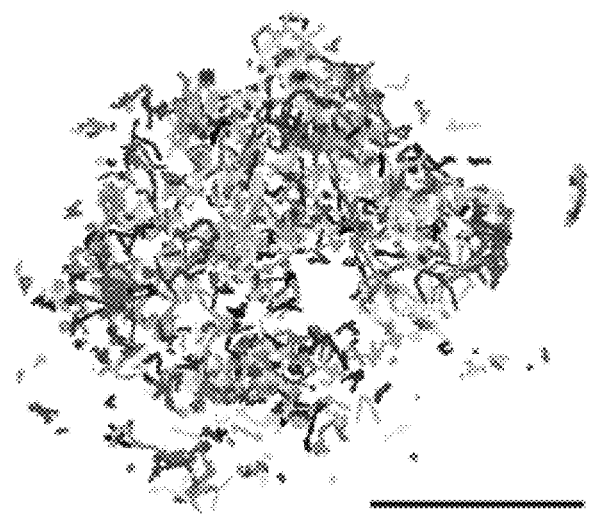
Figure 1E:
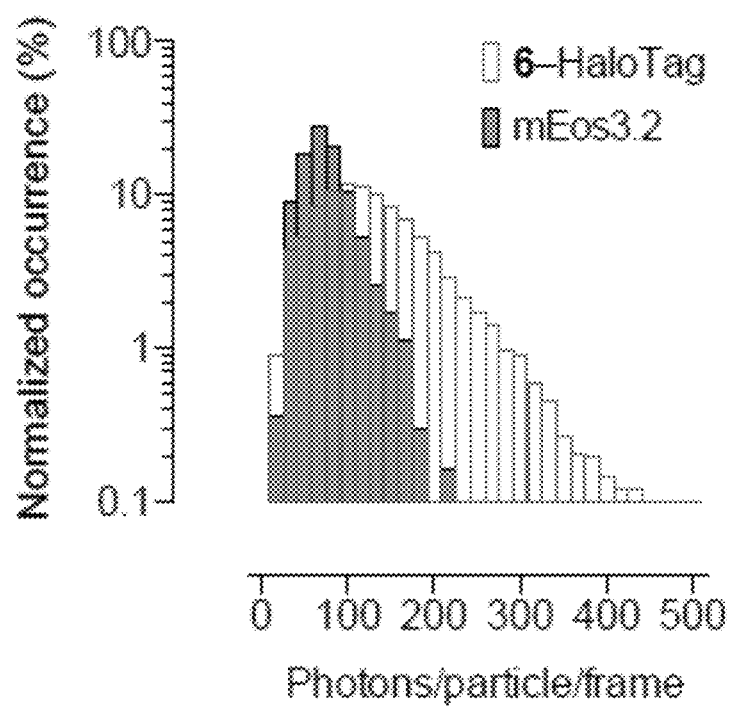
Figure 1F:
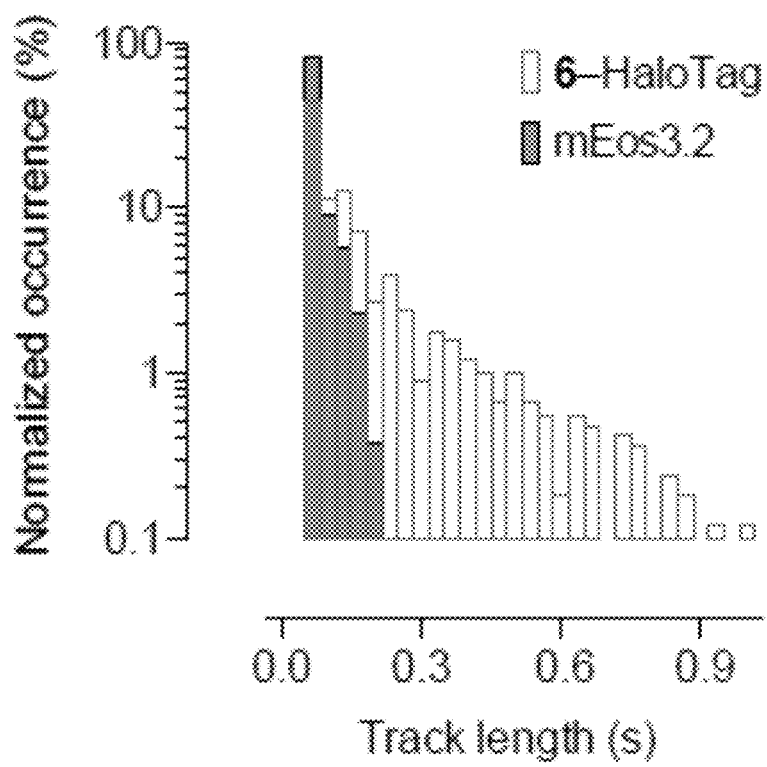

The dyes were then compared in single-particle tracking photoactivated localization microscopy (sptPALM) experiments in live mouse embryonic stem (ES) cells expressing HaloTag-Sox2 or mEos3.2-Sox2 fusions (FIG. 1D). As shown in FIGS. 1E-F, the PA-JF$_{549}$ showed a sizeable improvement in performance compared to the mEos3.2 fluorophore, giving higher detected photons/particle/frame (median=120.7) and longer tracks (mean=0.20 s) than mEos3.2 (median detected photons/particle/frame=70.9; mean track length=0.07 s). Performance of the PA-JF$_{549}$-HaloTag ligand (6) was also compared to the commercially available tetramethylrhodamine (TMR) HaloTag ligand (9) using a multifocus microscope (MFM) setup where superior performance of the PA-JF$_{549}$ ligand was observed in 3D tracking (FIGS. 3J-O).

Next, the utility of the PA-JF$_{549}$-HaloTag ligand as a label for PALM in fixed cells was tested. Mitochondrial protein TOMM20 fused to either mEos3.2 (FIG. 3P) or the HaloTag protein and labeled with ligand 6 (FIG. 1G) was imaged. As expected (FIG. 3I), the PA-JF$_{549}$-HaloTag conjugate gave higher photon counts per localization event per frame (median=636.6) (FIG. 1H) and calculated localization precision (median $\sigma$=13.5 nm) (FIG. 1I) compared to mEos3.2 (median detected photons/localization/frame=266.8; median $\sigma$=20.2 nm). It was also confirmed that the dyes could function as PALM labels with other HaloTag fusions in different cellular regions (FIGS. 3Q-S). Overall, the PA-JF$_{549}$ label gave relatively high photon counts and calculated localization precision and showed only modest blinking (FIGS. 3T-V). Nevertheless, the use of genetically encoded self-labeling tags does not address issues with labeling density—a key determinant of image quality in localization microscopy.

Figure 2A:
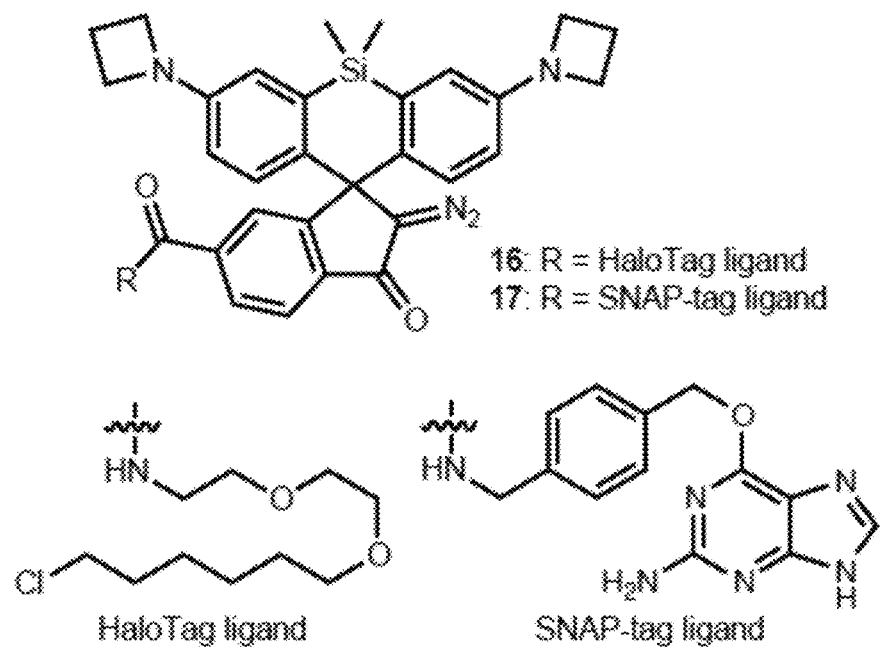
FIGS. 2A-H show graphs and images illustrating multicolor imaging using photoactivatable Janelia Fluor 646 (PA-JF$_{646}$). (A) Structures of PA-JF$_{646}$-HaloTag ligand (16) and PA-JF$_{646}$-SNAP-tag ligand (17). (B) Image of U2OS cell expressing TOMM20-HaloTag and labeled with 10 nM JF$_{549}$-HaloTag ligand 8 and 10 nM PA-JF$_{646}$-HaloTag ligand 16. The spatial distribution of the wide-field fluorescence microscopy image from JF$_{549}$-HaloTag ligand 8 resembles typical mitochondrial distribution in a cell (scale bar: 5 µm). The tracks (n=154) of single TOMM20 fusions labeled with PA-JF$_{646}$ are plotted on the averaged wide-field TOMM20-JF$_{549}$ signal (inset; scale bar: 1 µm). The majority of single molecule trajectories (>95%) colocalize with the JF$_{549}$-HaloTag signal, indicating specific labeling of PA-JF$_{646}$. (C-G) Simultaneous two-color sptPALM experiment in a live ES cell expressing histone H2B-SNAP-tag labeled with 17 and HaloTag-Sox2 labeled with PA-JF$_{549}$-HaloTag ligand (6). (C) PALM image of histone H2B-SNAP-tag labeled with 17; scale bar: 5 µm. (D) Single-particle trajectories of HaloTag-Sox2 that are colocalized with histone H2B-SNAP-tag (6272 trajectories, magenta) or non-colocalized with histone H2B-SNAP-tag (7081 trajectories, green). (E) Apparent diffusion coefficient map of colocalized fraction of Sox2. (F) Apparent diffusion coefficient map of non-colocalized fraction of Sox2. (G) Histogram of apparent diffusion coefficient calculated for each step in the colocalized and non-colocalized Sox2 trajectories. (H) Overlay of the PALM image of Htt84Q-mEos3.2-NLS clusters with the PALM image of histone H2B-HaloTag labeled with 16. The PALM images were simultaneously recorded and are each composed of 10,000 consecutive frames. The 128,740 detected mEos3.2 molecules (green) and the 739,964 PA-JF$_{646}$ molecules (magenta) are displayed according to their localization full-width at half-maximum. The median number of detected photons per mEos3.2 molecule per frame was 115.6, and the median number of detected photons per PA-JF$_{646}$ molecule per frame was 757.6. The median calculated localization error for mEos3.2 was 34.5 nm, and for PA-JF$_{646}$ was 21.3 nm. Scale-bar: 5 µm.
Figure 2B:
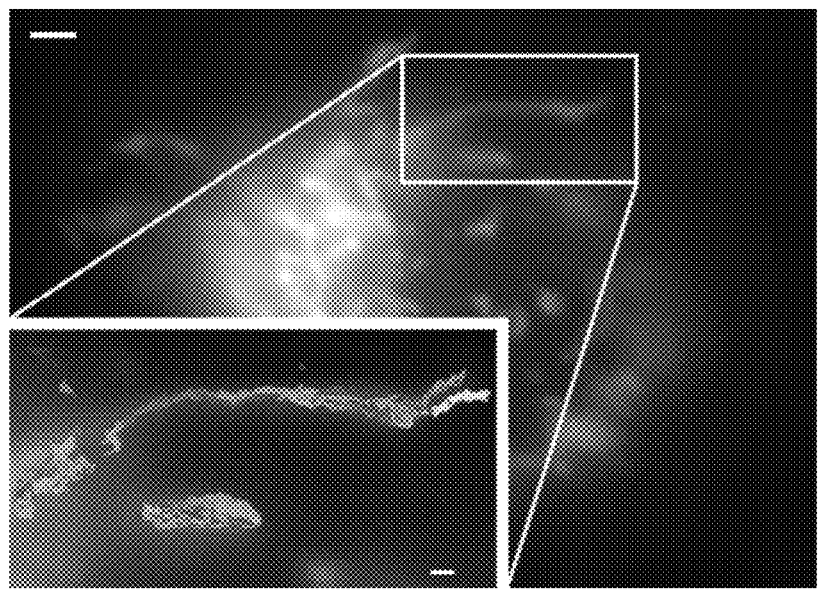
Figure 4A:
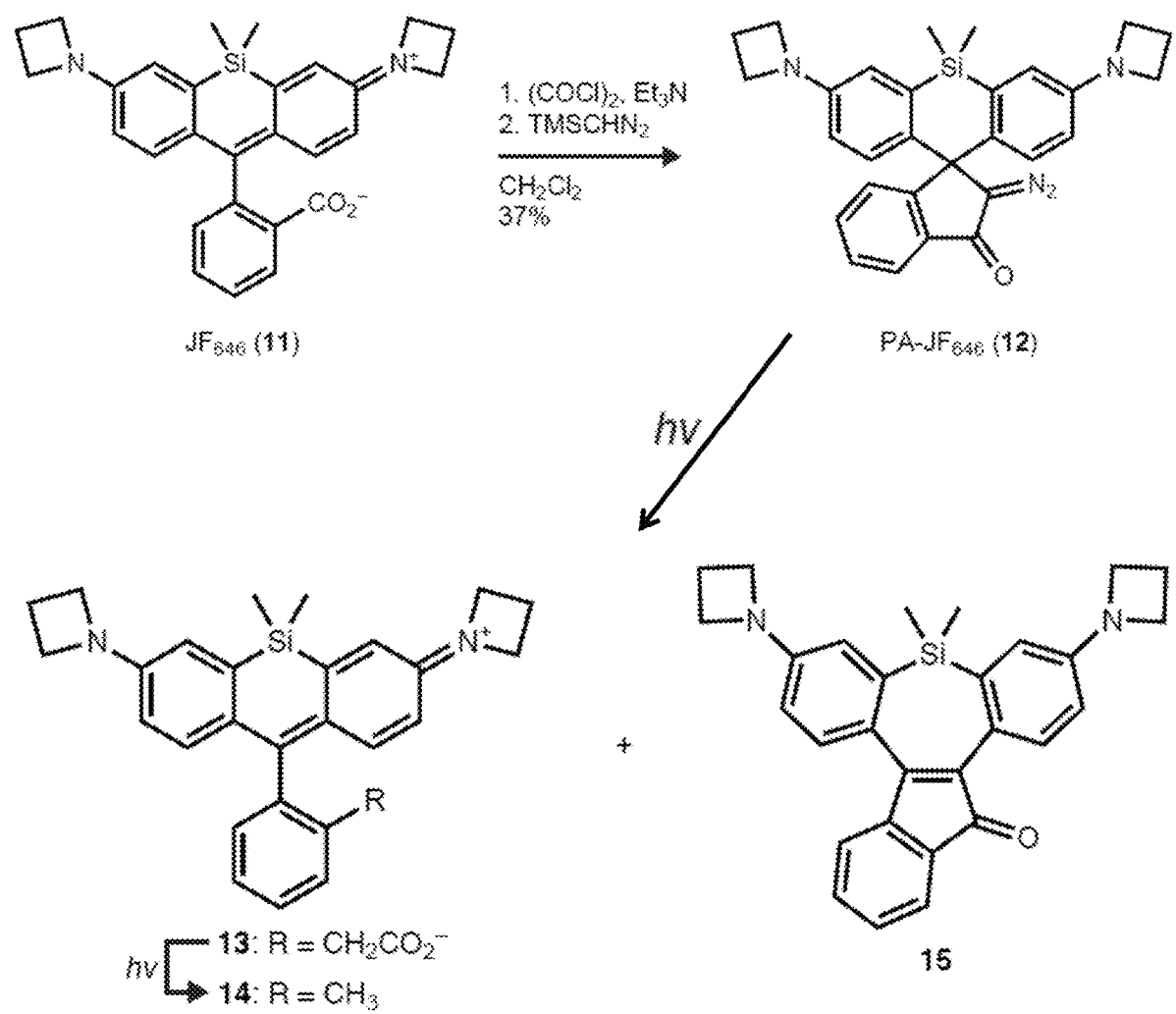
FIGS. 4A-N shows graphs and images illustrating synthesis, properties, and performance of photoactivatable Janelia Fluor 646 (PA-JF$_{646}$). (A) Synthesis and photochemistry of PA-JF$_{646}$. Treatment of JF$_{646}$ (11) with oxalyl chloride and TMS diazomethane yields PA-JF$_{646}$ (12). Photoactivation (365 nm) yields only a trace amount of both the phenylacetic derivative (13; <1%) and methyl-substituted JF$_{549}$ (14; 4%); the major product is the indanone 15 (24%; isolated yields). (B) Structure of JF$_{646}$-HaloTag ligand 18 and JF$_{646}$-SNAP-tag ligand 19. (C) Absolute absorbance spectrum of PA-JF$_{646}$-HaloTag ligand (16) bound to HaloTag protein before (-hv, black line) and after photoactivation (365 nm; +hv, magenta lines). (D) Comparison of the absolute absorbance spectrum of 18 (5 µM) incubated with HaloTag protein (black) with the absorbance spectrum of 16 (5 µM) incubated with (magenta) or without (dashed magenta) HaloTag protein and then exhaustively photoactivated with 365 nm light. (E) Comparison of the absolute absorbance spectrum of 19 (5 µM) incubated with SNAP-tag protein (black) with the absorbance spectrum of 17 (5 µM) incubated with (magenta) or without (dashed magenta) SNAP-tag protein and then exhaustively photoactivated with 365 nm light. (F) Activation rate of histone H2B-HaloTag labeled with PA-JF$_{646}$-HaloTag ligand (6) in live U2OS cells (identical photoactivation conditions and equivalent excitation power to FIG. 3G; n=5, shading shows±s.e.m.) overlaid with exponential fit (black). (G) Plot comparing the spontaneous activation of TOMM20-HaloTag labeled with PA-JF$_{646}$-HaloTag ligand (16; magenta) or TOMM20-mEos3.2 (black) in fixed U2OS cells in the absence of 405 nm activation light; solid lines show linear fits. (H-I) Evaluation of background staining of HaloTag ligands 6 and 16. COST cells expressing no fusion protein (left panels) or a histone H2B-HaloTag fusion (right panels) were fixed, stained with HaloTag ligand (100 nM; 30 min) and Hoechst 33342 (5 µg/mL), photoactivated (405 nm), and then imaged using the same settings. Scale bars: 50 µm. (H) PA-JF$_{549}$-HaloTag ligand 6. (I) PA-JF$_{646}$-HaloTag ligand 16. (J-K) Two live ES cells expressing histone H2B-SNAP-tag labeled with PA-JF$_{646}$-SNAP-tag ligand (17) and HaloTag-Sox2 labeled with PA-JF$_{549}$-HaloTag ligand (6). Upper images show localization microscopy image (PALM), center images show cumulative single-particle trajectories, and lower images show apparent diffusion coefficient map. Scale bar: 5 µm. (J) Images from histone H2B-SNAP-tag labeled with 17. (K) Images from HaloTag-Sox2 labeled with 6. (L) PALM image of U2OS cell expressing vimentin-HaloTag fusions and labeled with ligand 16. The image is composed of 151,808 localizations with a median calculated localization error of 20.4 nm. Scale-bar: 5 µm. (M) PALM image of U2OS cell expressing TOMM20-HaloTag fusions and labeled with ligand 16. The PALM image is composed of 203,015 detected molecules. The median calculated localization error was 13.8 nm. Scale-bar: 2 µm. (N) Histogram of calculated localization precision when performing PALM of TOMM20 using the 16-HaloTag fusion (magenta, median=13.8 nm) or mEos3.2 fusion (black, median=20.2 nm).
Figure 4B:
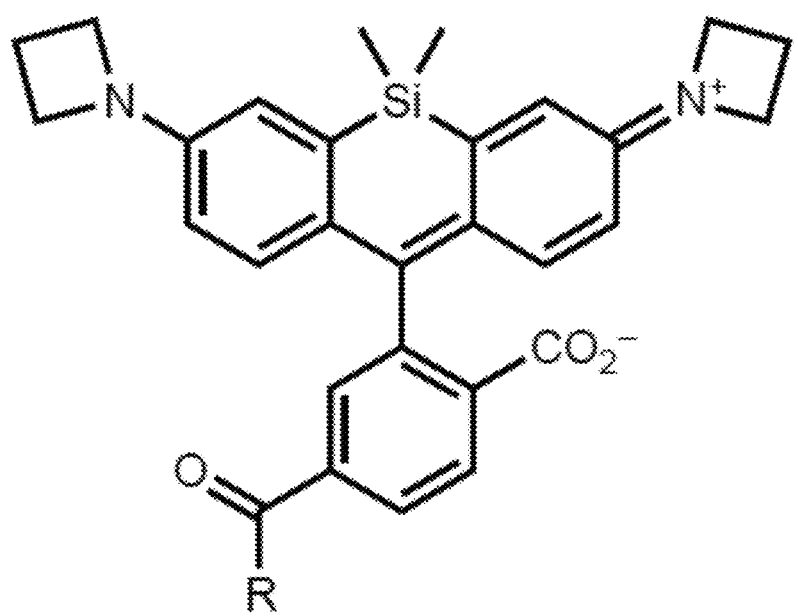
Figure 4C:
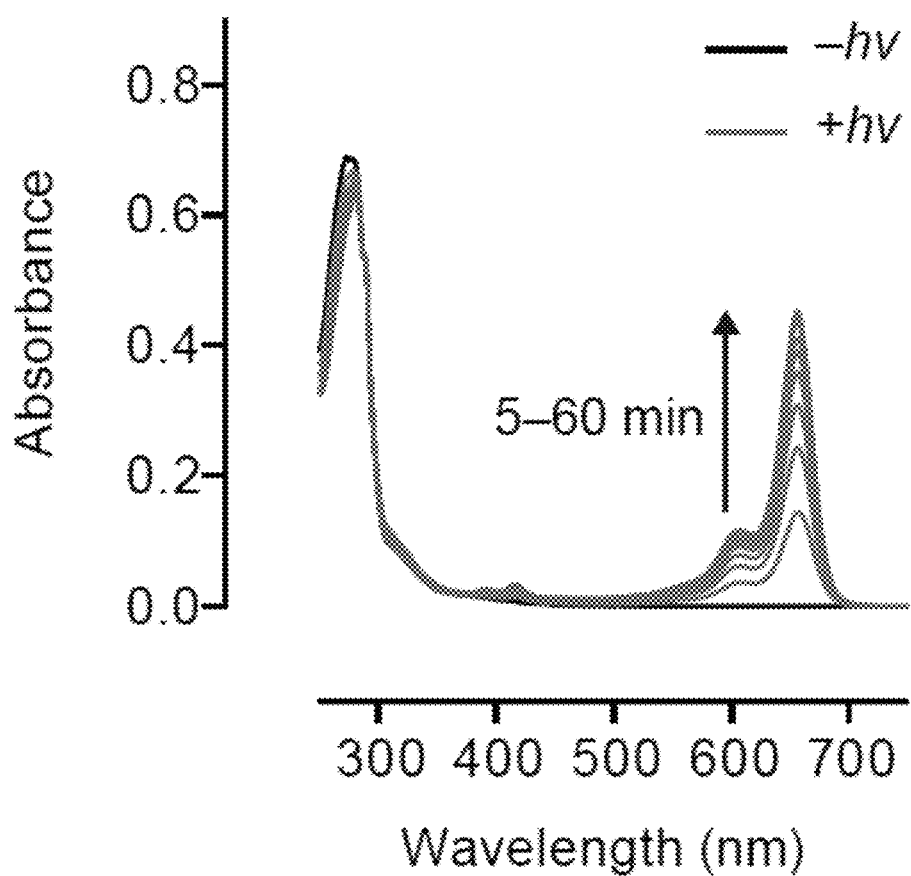
Figure 4D:
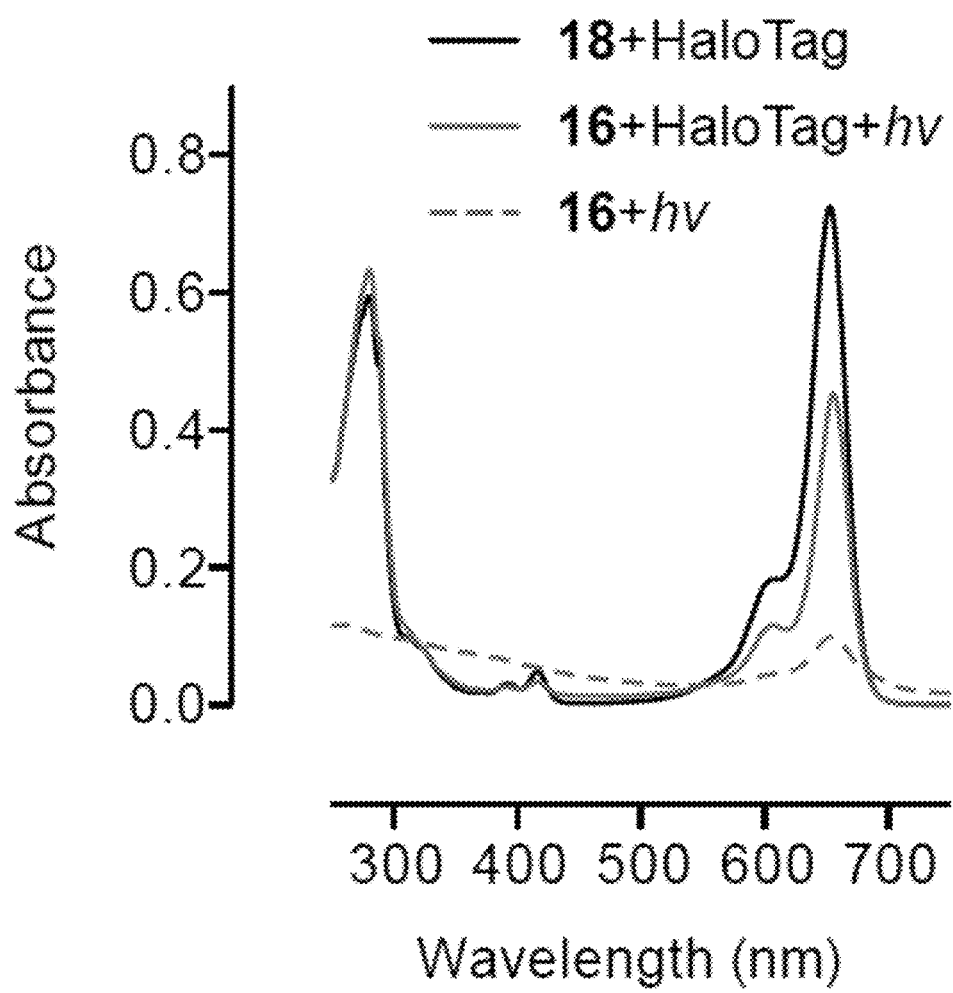
Figure 4E:
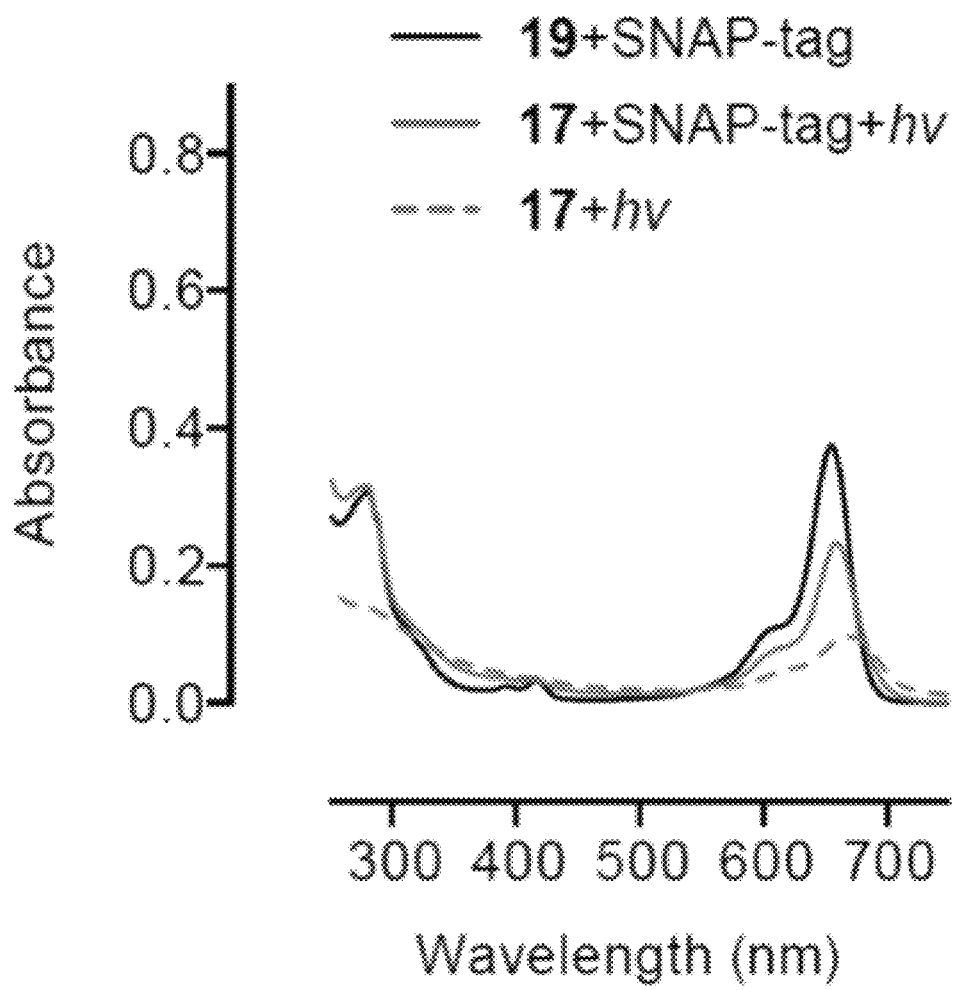
Figure 4F:
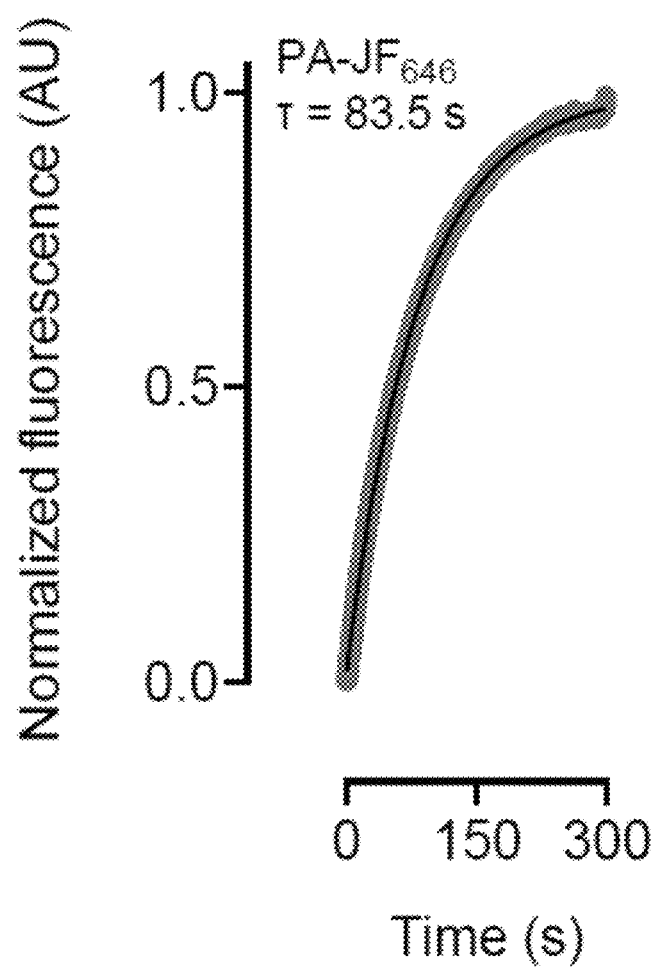
Figure 4G:
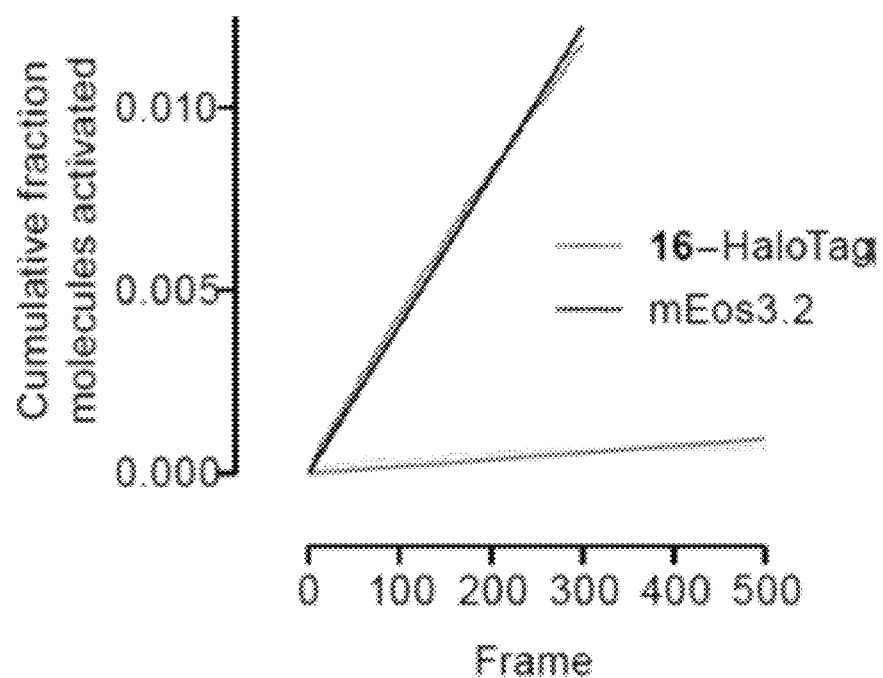
Figure 4H:
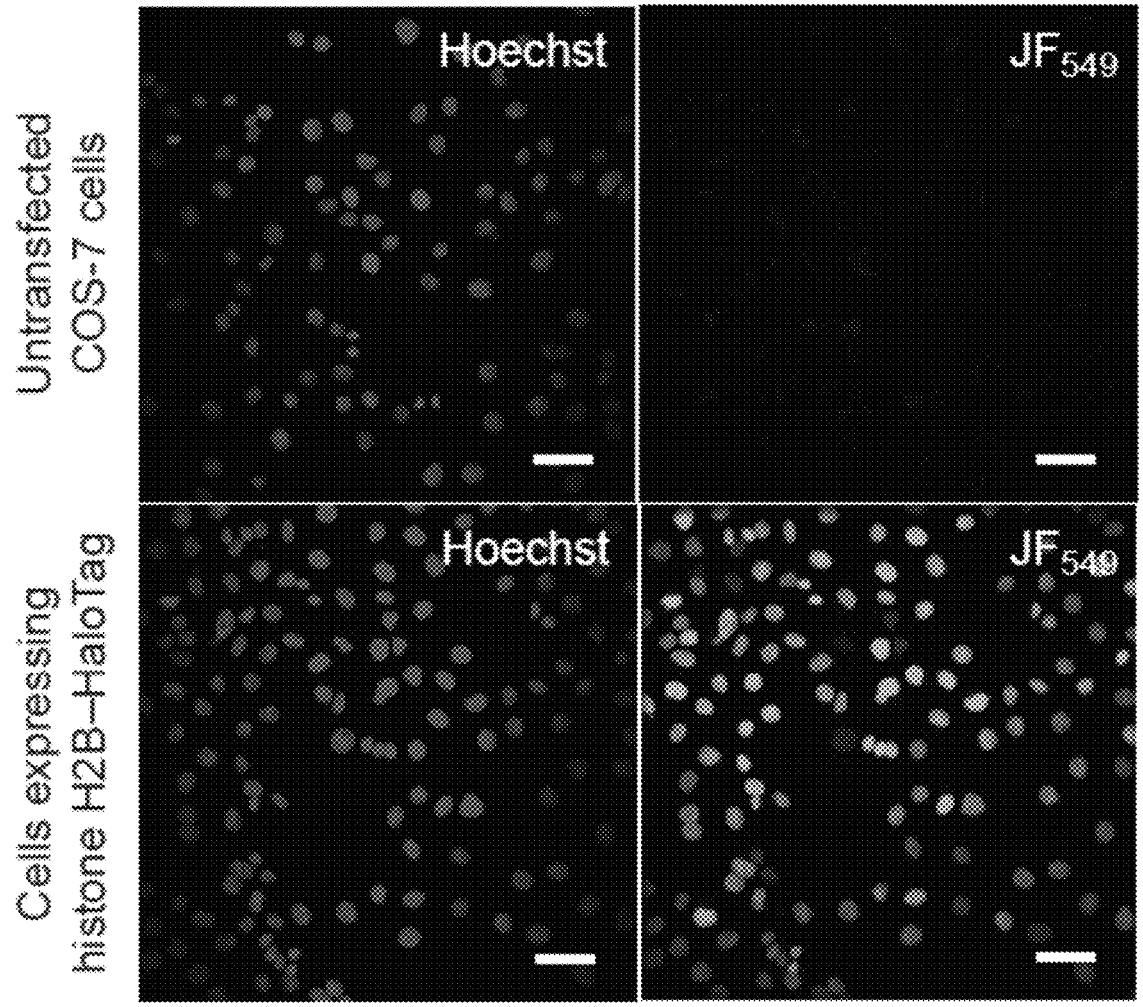
Figure 4I:
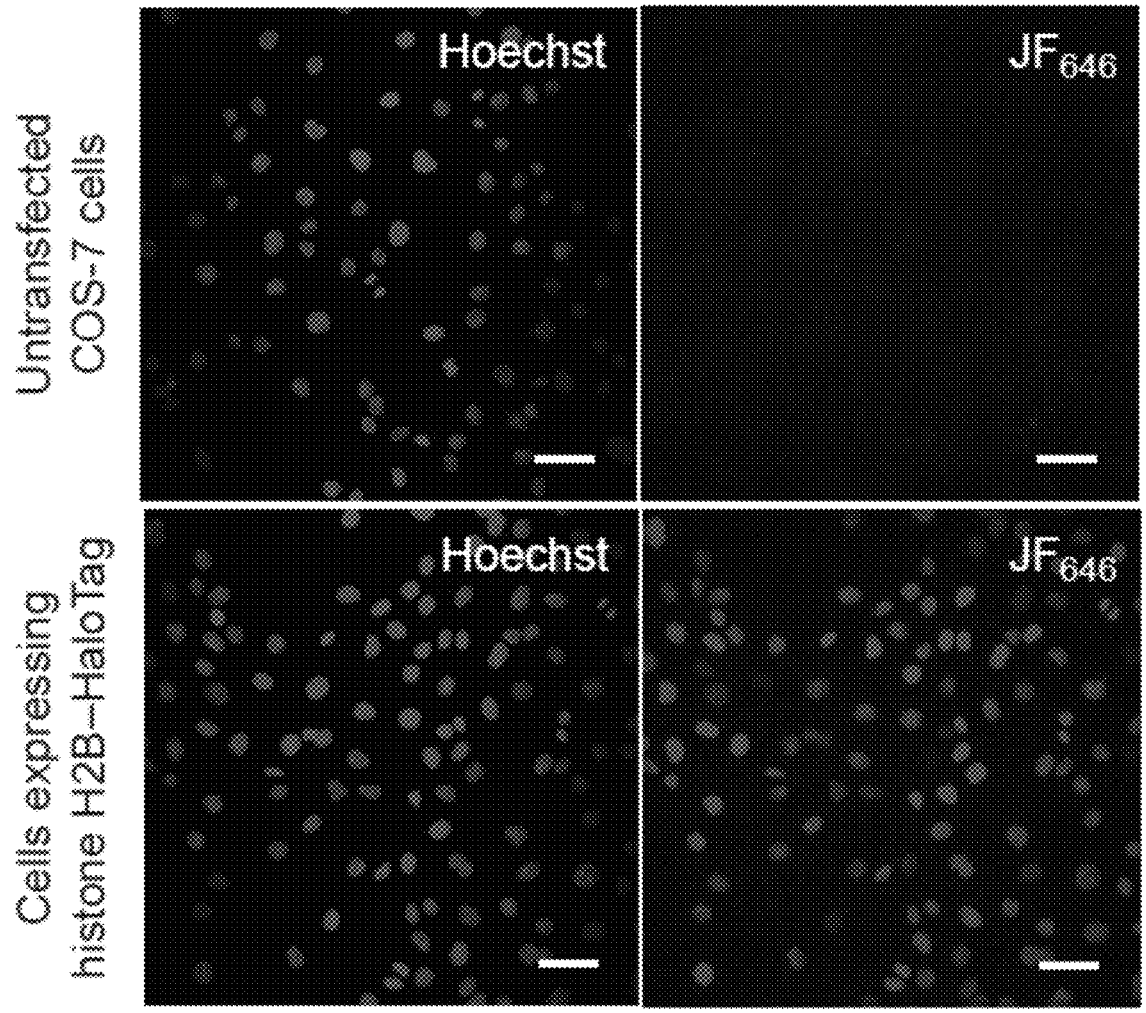

Two-color single-particle tracking PALM was then performed, an experiment that had been stymied by the scarcity of two spectrally distinct photoactivatable fluorophores. It was reasoned that use of the same diazoketone caging strategy on different Janelia Fluor dyes could allow sparse photoactivation of both labels with similar efficiency, thus facilitating two-color experiments. Accordingly, as illustrated in FIG. 4A, $JF_{646}$ (11) was first converted into the photoactivatable Janelia Fluor 646 (PA-$JF_{646}$) (12) to test whether this caging strategy would be compatible with the Si-rhodamine scaffold. Interestingly, photolysis of the free PA-$JF_{646}$ 12 gave only small amounts (<5%) of the expected fluorophores 13 and 14, with the major product being the nonfluorescent 15 (FIG. 4A). Nevertheless, based on the "on-protein" improvement in photochemistry observed for the PA-$JF_{549}$ compounds (FIGS. 3A-F), it was predicted that PA-$JF_{646}$ would show better performance as a photoactivatable fluorophore when conjugated. Accordingly, the HaloTag ligand of PA-$JF_{646}$ (16) and the SNAP-tag ligand of PA-$JF_{646}$ (17), which are illustrated in FIG. 2A, were synthesized. These compounds showed substantial improvements in photochemical outcome upon binding to their cognate protein (FIGS. 4B-E) and a high activation rate ($\tau$=83.5) in live cells (FIG. 4F). The on-off ratio was substantially higher (~$10^{-6}$) due to the lower rate of spontaneous activation under the red excitation light (FIG. 4G, Table 1). The low background staining exhibited with PA-$JF_{549}$ ligand 6 was also observed with the PA-$JF_{646}$-HaloTag ligand 16 (FIGS. 4H-I) allowing sptPALM in live cells (FIG. 2B).

Figure 2C:
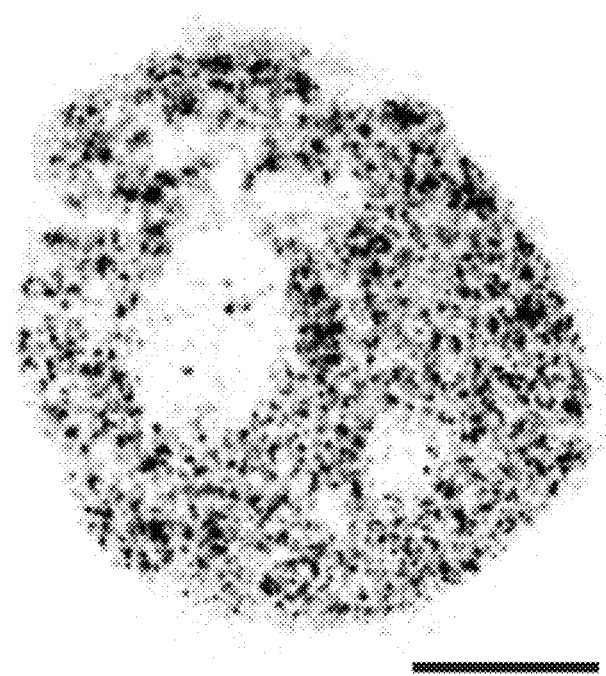
Figure 2D:
Figure 2E:
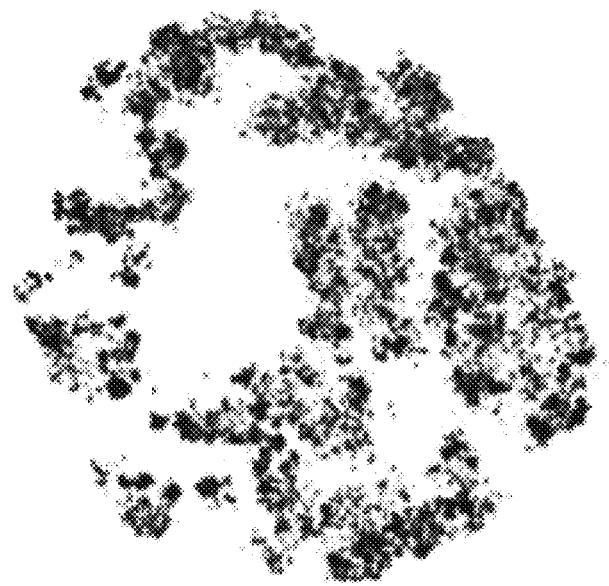
Figure 2F:
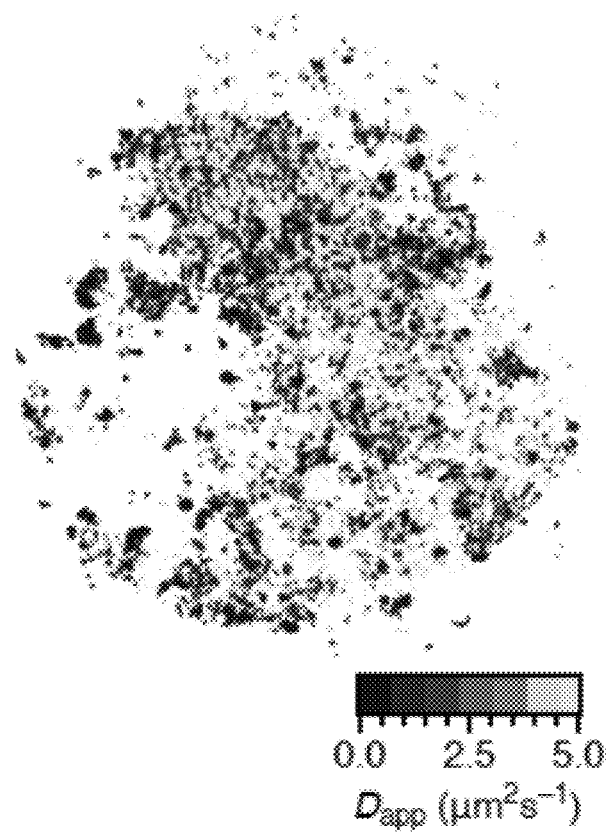
Figure 2G:
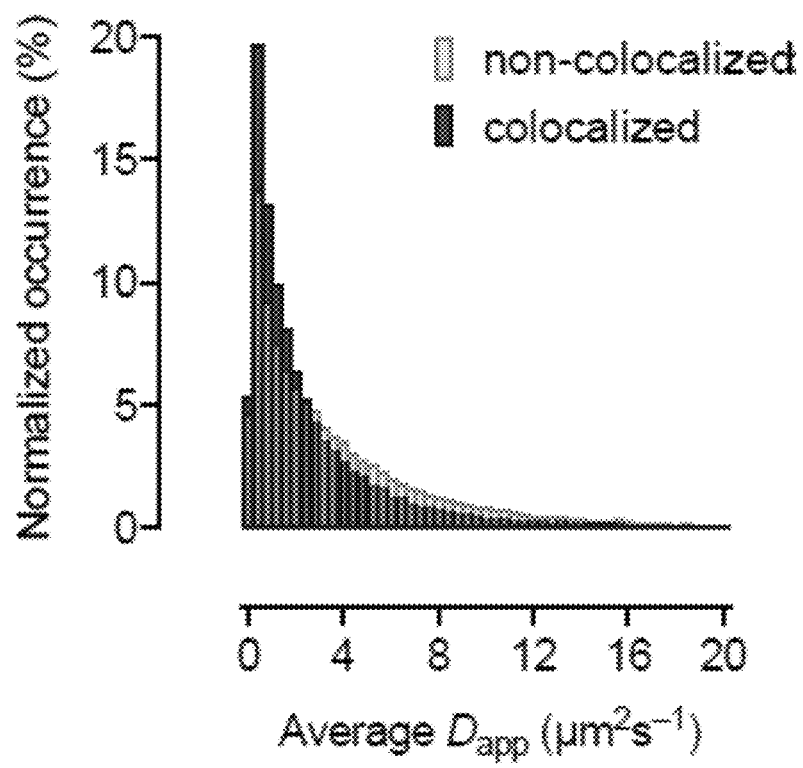

To further validate the PA-$JF_{646}$ pair for two-color spt-PALM, the transcription factor Sox2 was expressed as a fusion with HaloTag protein and labeled with PA-$JF_{549}$-HaloTag ligand 6. Histone H2B was coexpressed as a fusion with the SNAP-tag and this population was labeled with PA-$JF_{646}$-SNAP-tag ligand (17). These photoactivatable dyes allowed simultaneous tracking of both H2B and Sox2 by photoactivation with 405 nm light. A map of histone H2B location was generated using a standard PALM analysis (FIG. 2C) and used to define Sox2 trajectories that were either colocalized or not colocalized with the areas of high density in the chromatin PALM map (FIG. 2D). As illustrated in FIGS. 2E-G and 4J-K, the molecules of Sox2 that were colocalized with histone H2B exhibited slower diffusion coefficients than the non-colocalized fraction.

Finally, the PA-$JF_{646}$ label was investigated for multicolor localization microscopy. Although a few self-labeling tag ligands have been used for PALM imaging, previously reported molecules exhibit relatively short emission maxima, and are thus incompatible with other localization microscopy labels such as photoconvertible fluorescent proteins. Based on the instant inventors previous work with another caged Si-rhodamine with similar wavelengths, it was reasoned that PA-$JF_{646}$ would be red-shifted enough to be useful for two-color PALM with mEos3.2. As illustrated in FIGS. 4L-M, it was first shown that PA-$JF_{646}$-HaloTag ligand 16 may be used for one-color PALM in cells expressing HaloTag-vimentin or HaloTag-TOMM20 fusions. The calculated localization precision in the TOMM20 image using PA-$JF_{646}$ ligand 16 was similar to PA-$JF_{549}$ (median $\sigma$=13.8 nm) (FIGS. 1I and 4N). For a two-color experiment, the mutant Huntingtin protein Htt-94Q was expressed as a fusion protein with mEos3.2 and histone H2B as a fusion with the HaloTag, labeling with PA-$JF_{646}$-HaloTag ligand 16. After labeling, fixation, and two-color PALM (FIG. 2H), it was observed that histone H2B (magenta) and Htt-94Q aggregates (green) only rarely overlap (i.e., few white spots), which supports the hypothesis that the aggregates formed by expanded polyglutamine domains displace chromatin structures in the nucleus.

In conclusion, the methods described above provide photoactivatable versions of the bright, photostable Janelia Fluor dyes. These fluorophores retain the superior photon yields and utility in live cells exhibited by the fluorescent JF dyes but have the added benefit of photoactivation, facilitating sophisticated single-particle tracking PALM experiments. These dyes also constitute a useful addition to the expanding palette of PALM labels for fixed cells. In particular, PA-$JF_{646}$ is the first far-red photoactivatable fluorophore compatible with live-cell labeling using the HaloTag or SNAP-tag systems, allowing multicolor single-particle tracking experiments and super-resolution microscopy.

Without wishing to be bound by theory, these small and bright photoactivatable labels are believed to be compatible with many different labeling strategies, therefore extending the boundaries of single-molecule imaging in live and fixed cells. Beyond localization microscopy, these versatile, membrane-permeable labels should provide a favorable alternative to photoconvertible fluorescent proteins in any live imaging experiment where photoactivation is used to highlight a specific cell or cellular region.

Methods

Chemical Synthesis and Photochemistry. Experimental details and characterization for all novel compounds and subsequent spectroscopy and photochemistry experiments can be found in Example 2.

UV-Vis and Fluorescence Spectroscopy. Spectroscopy was performed using 1-cm path length quartz cuvettes. All measurements were taken at ambient temperature (22±2° C.). Absorption spectra were recorded on a Cary Model 100 spectrometer (Agilent). Fluorescence spectra were recorded on a Cary Eclipse fluorometer (Varian). Absolute fluorescence quantum yields ($\Phi_F$) for all fluorophores were measured using a Quantaurus-QY spectrometer (model C11374, Hamamatsu).

General Microscopy Methods. A comprehensive listing of instrument parameters for all imaging experiments can be found in Table 2. Additional information is given below.

TABLE 2

Comprehensive Listing of Instrumental Properties

| Figure panel | Label | Ligand | Objective type | Magnification | Pixel size (nm) | Excitation wavelength (nm) |
| --- | --- | --- | --- | --- | --- | --- |
| FIGS. 1D-F | HaloTag-Sox2 | PA-$JF_{549}$ | Olympus 60× NA 1.49 TIRF | 100× | 160 | 555 |
| FIGS. 1E-F | mEos3.2-Sox2 | none | Olympus 60× NA 1.49 TIRF | 100× | 160 | 555 |

TABLE 2-continued

Comprehensive Listing of Instrumental Properties

Figure 1G:
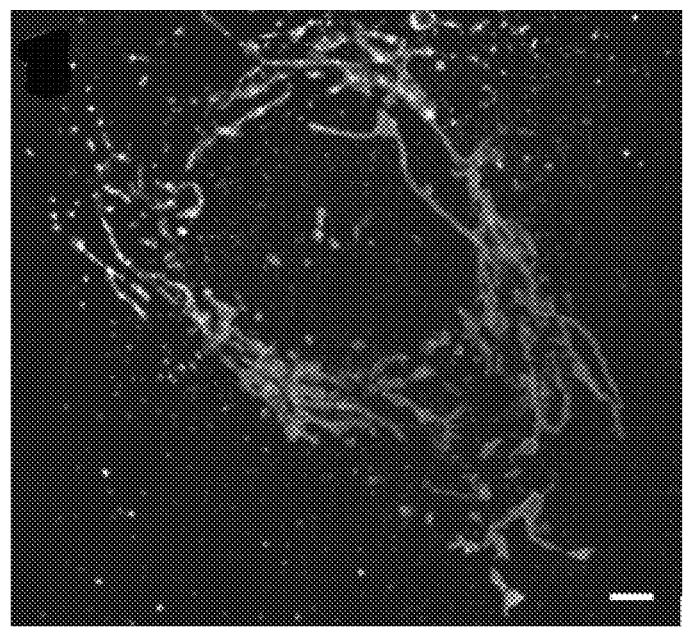
Figure 1H:
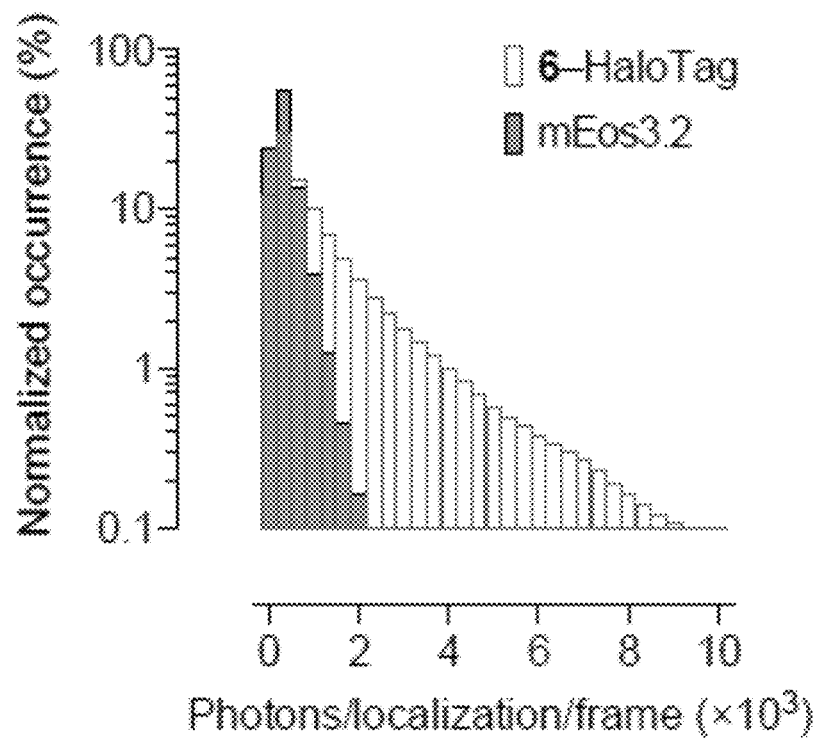
Figure 1I:
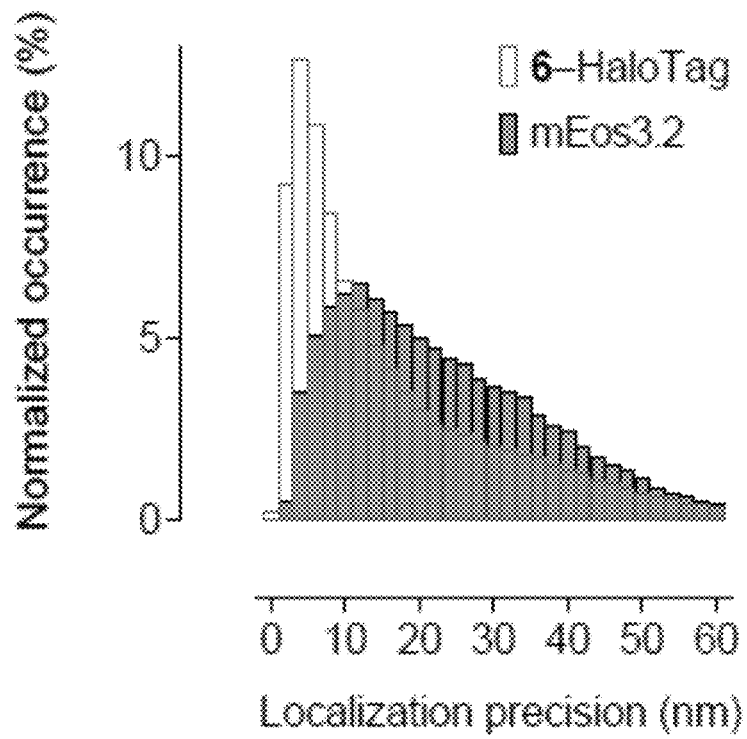
Figure 2H:
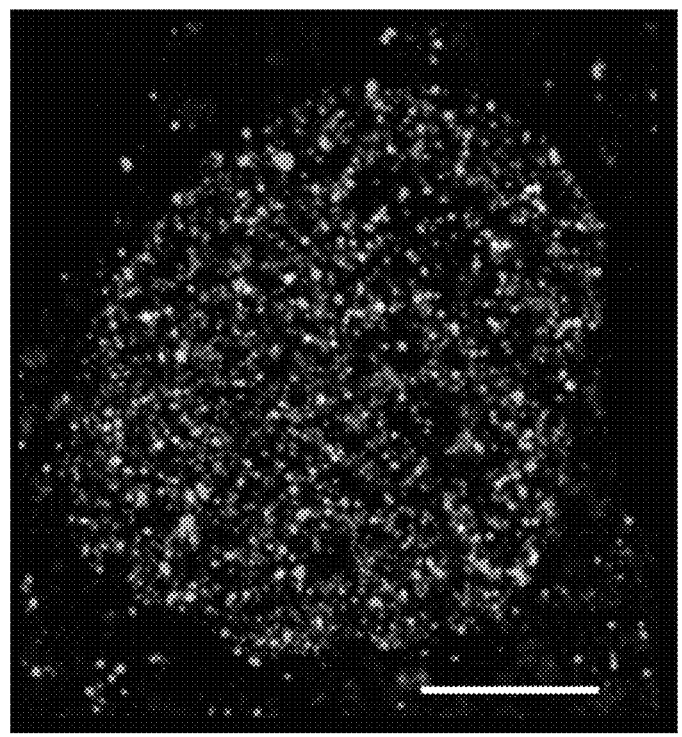
Figure 3I:
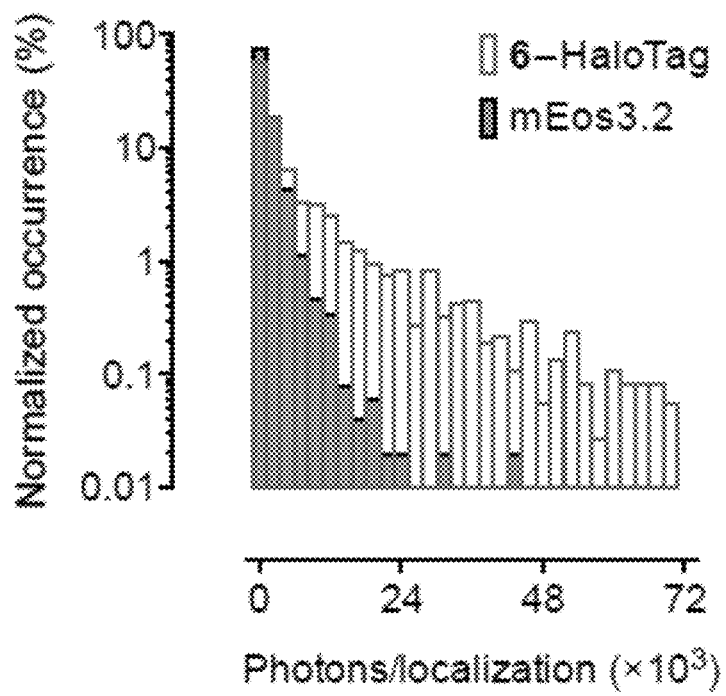
Figure 3J:
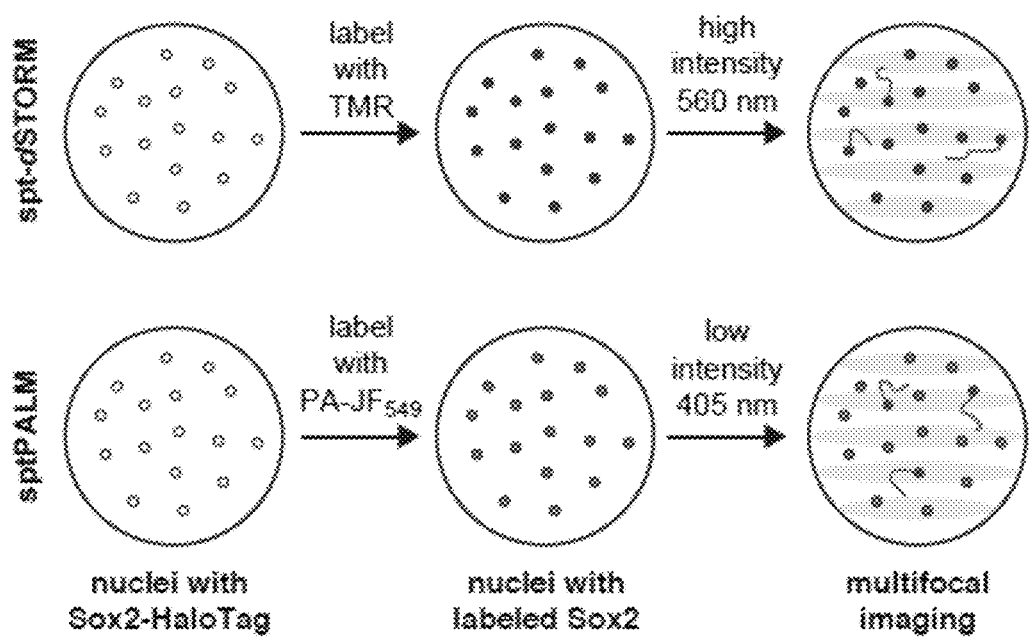
Figure 3K:
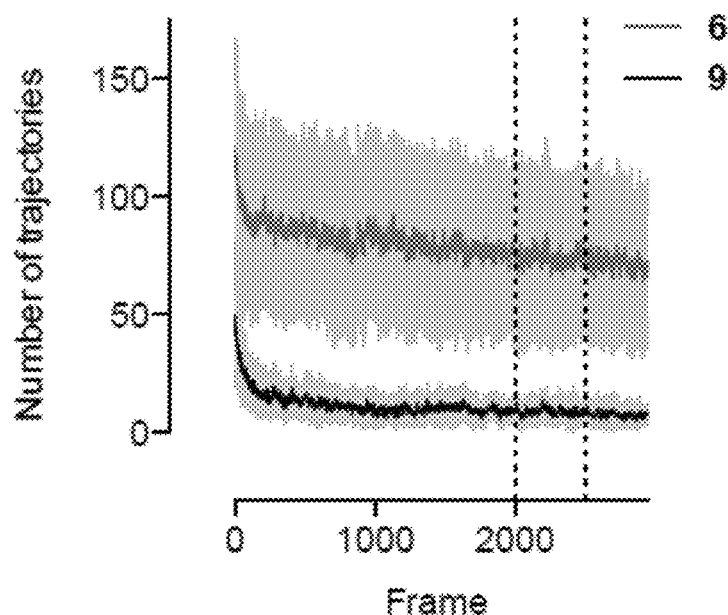
Figure 3L:
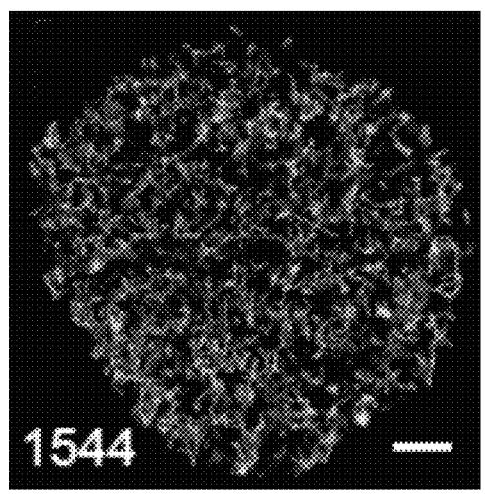
Figure 3M:
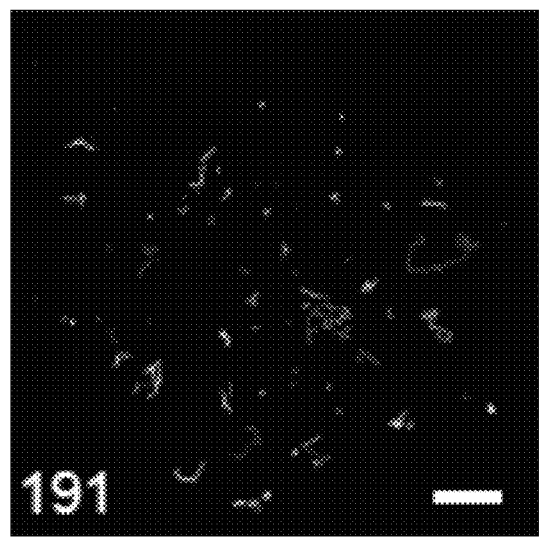
Figure 3N:
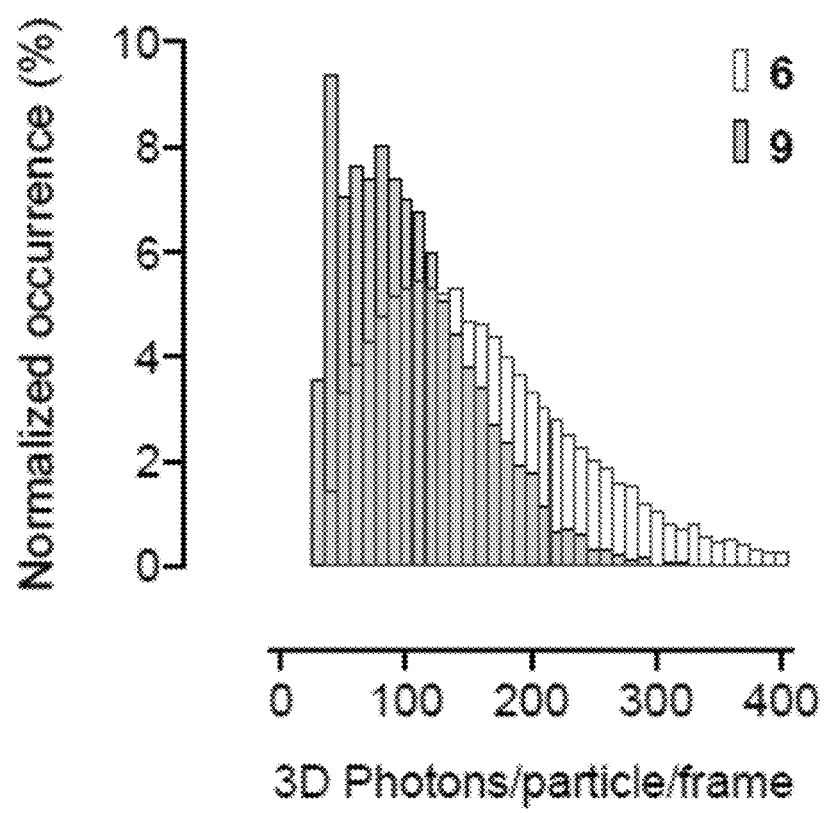
Figure 3O:
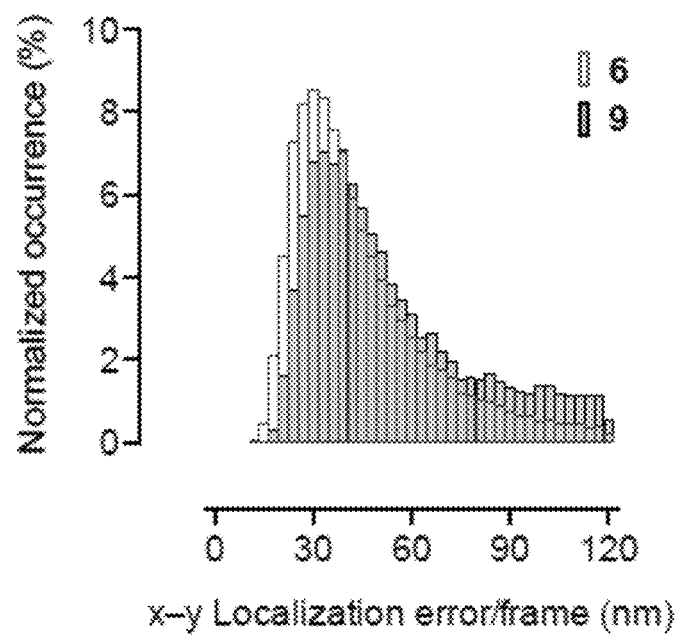
Figure 3P:
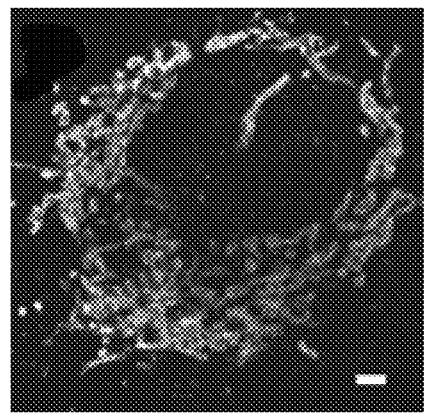
Figure 3Q:
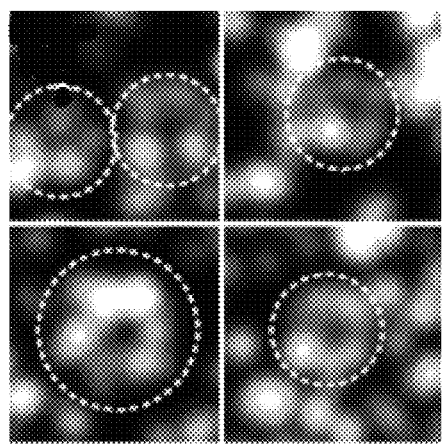
Figure 3R:
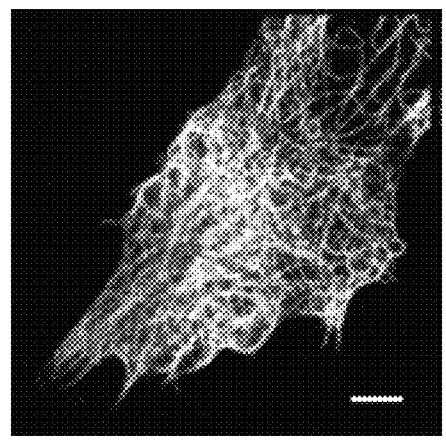
Figure 3S:
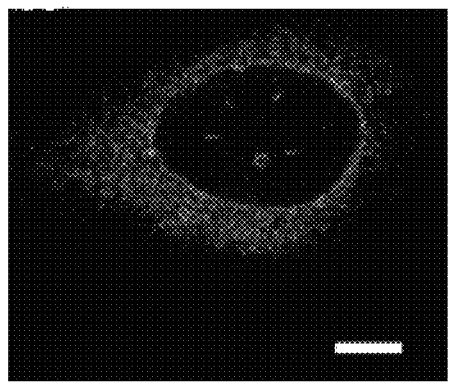
Figure 3T:
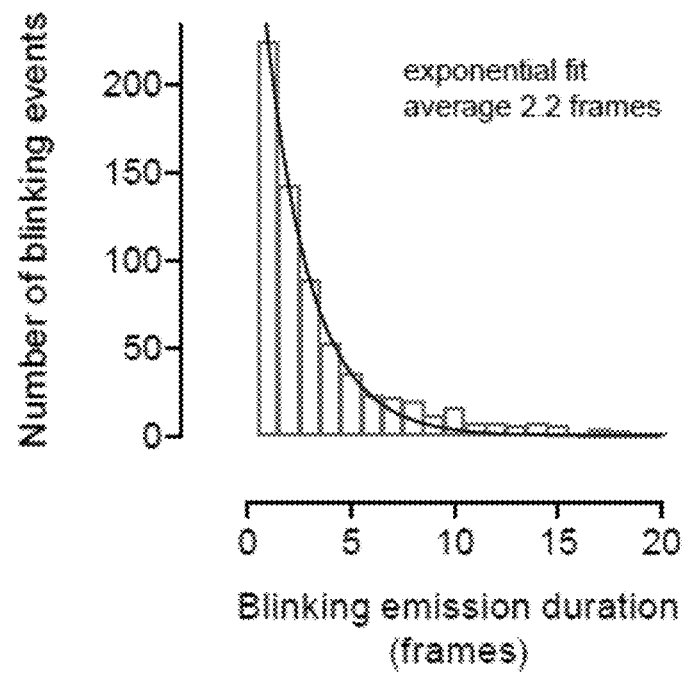
Figure 3U:
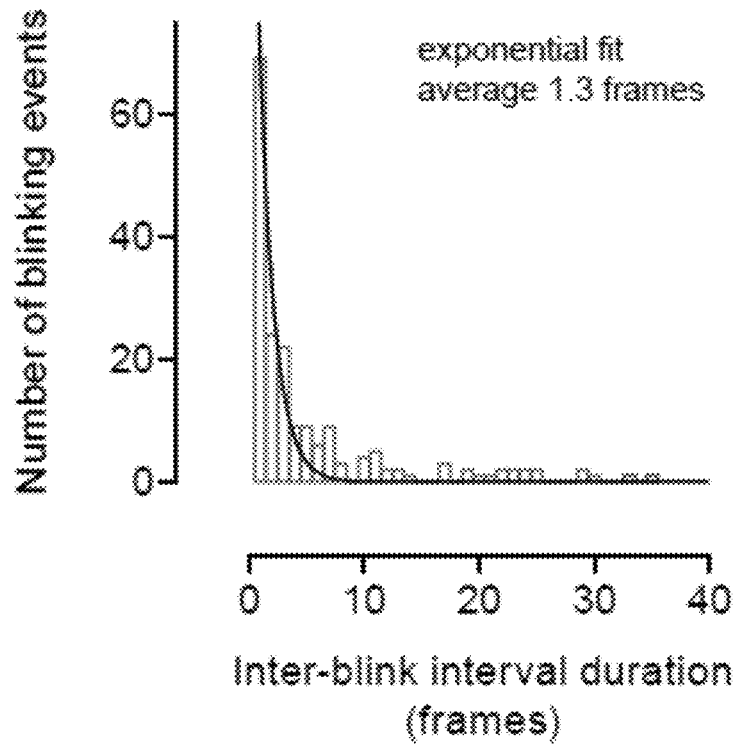
Figure 3V:
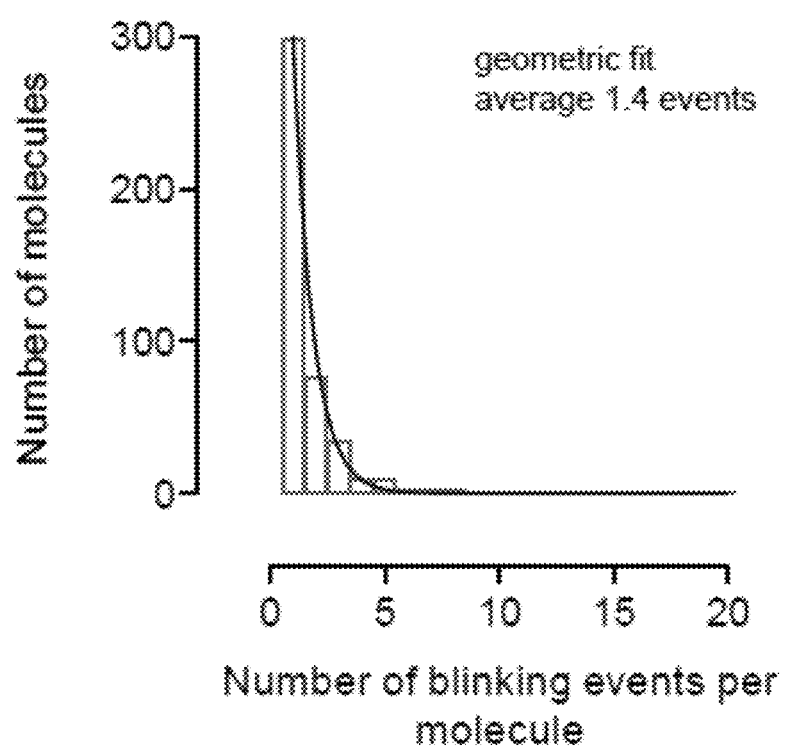
Figure 4J:
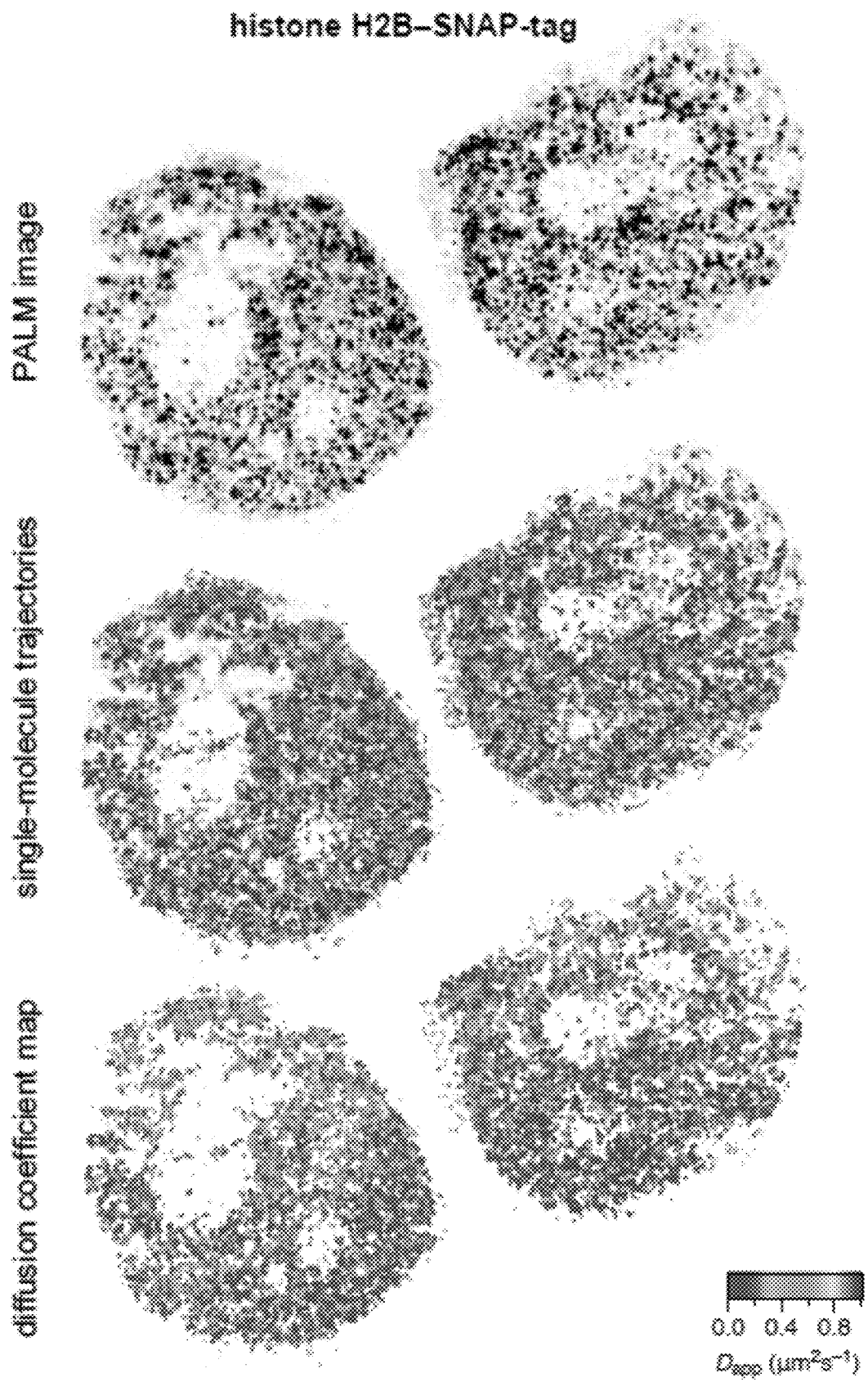
Figure 4K:
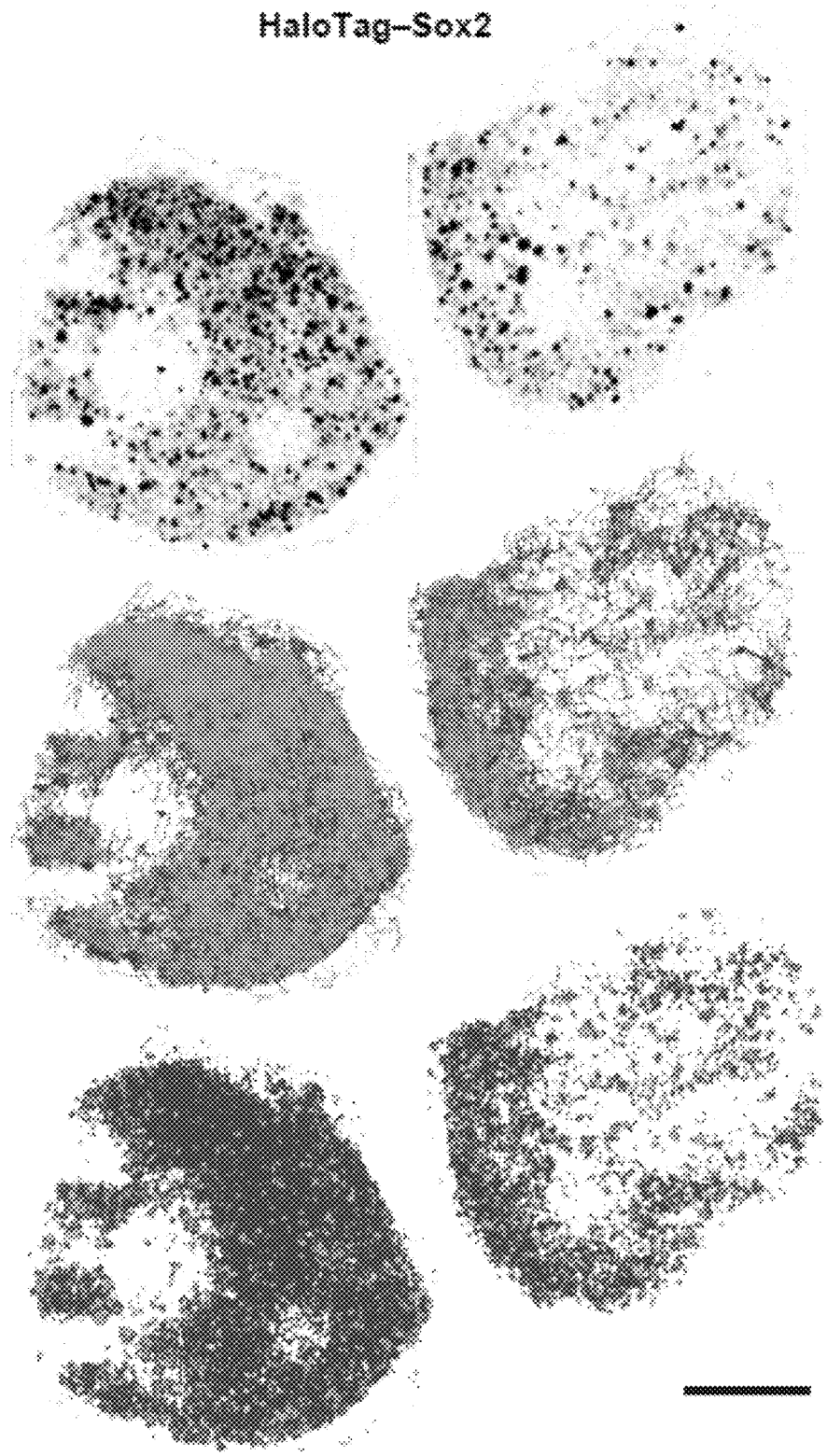
Figure 4L:
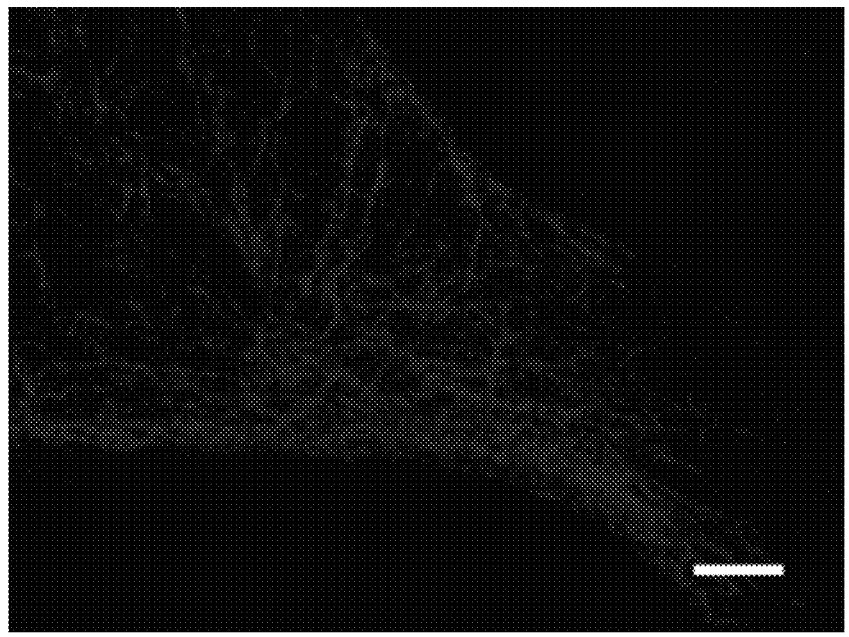
Figure 4M:
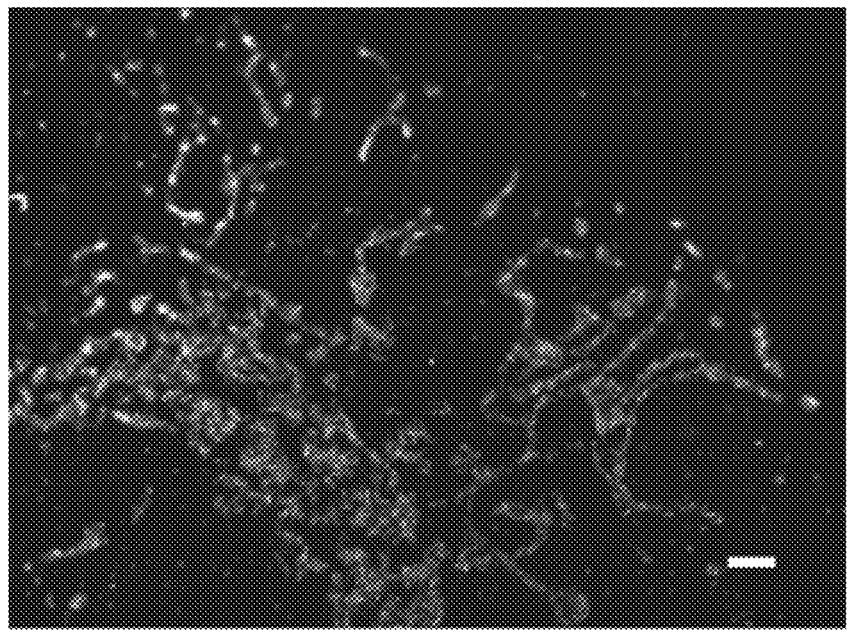
Figure 4N:
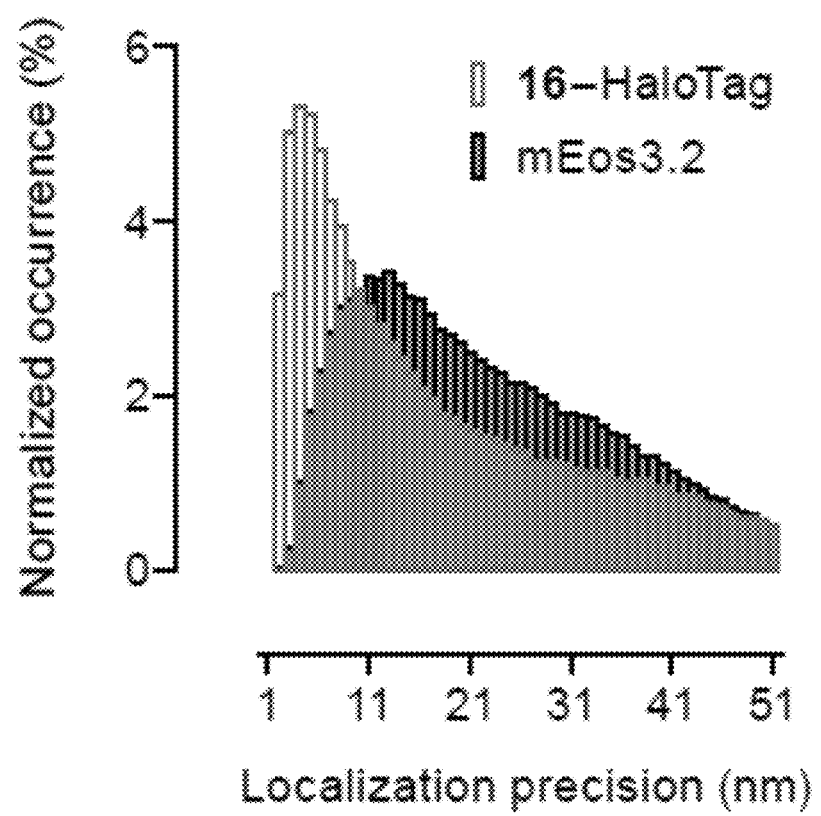

| Figure panel | | | | | | |
|---|---|---|---|---|---|---|
| FIGS. 1G-I | TOMM20-HaloTag | PA-JF$_{549}$ | Olympus 100x NA 1.4 | 166.67x | 96 | 555 |
| FIGS. 1H-I | TOMM20-mEos3.2 | none | Olympus 100x NA 1.4 | 166.67x | 96 | 555 |
| FIG. 2B | TOMM20-HaloTag | PA-JF$_{549}$ | Olympus 60x NA 1.49 TIRF | 100x | 160 | 555 |
| FIG. 2B | TOMM20-HaloTag | PA-JF$_{646}$ | Olympus 60x NA 1.49 TIRF | 100x | 160 | 555 |
| FIGS. 2C-G | histone H2B-SNAP-tag | PA-JF$_{646}$ | Olympus 60x NA 1.49 TIRF | 100x | 160 | 639 |
| FIGS. 2C-G | HaloTag-Sox2 | PA-JF$_{549}$ | Olympus 60x NA 1.49 TIRF | 100x | 160 | 555 |
| FIG. 2H | histone H2B-SNAP-tag | PA-JF$_{646}$ | Olympus 60x NA 1.49 TIRF | 100x | 160 | 639 |
| FIG. 2H | Htt94Q-mEos3.2 | none | Olympus 60x NA 1.49 TIRF | 100x | 160 | 555 |
| FIG. 3G | histone H2B-HaloTag | PA-JF$_{549}$ | Olympus 60x NA 1.49 TIRF | 100x | 160 | 561 |
| FIG. 3G | histone H2B-mEos3.2 | none | Olympus 60x NA 1.49 TIRF | 100x | 160 | 561 |
| FIG. 3H | TOMM20-HaloTag | PA-JF$_{549}$ | Olympus 60x NA 1.49 TIRF | 100x | 160 | 561 |
| FIG. 3H | TOMM20-mEos3.2 | none | Olympus 60x NA 1.49 TIRF | 100x | 160 | 561 |
| FIG. 3I | TOMM20-mEos3.2 | none | Olympus 60x NA 1.49 TIRF | 100x | 160 | 561 |
| FIG. 3I | TOMM20-HaloTag | PA-JF$_{549}$ | Olympus 60x NA 1.49 TIRF | 100x | 160 | 561 |
| FIG. 3J-O | HaloTag-Sox2 | PA-JF$_{549}$ | Nikon 100x NA 1.41 | 100x | 160 | 561 |
| FIG. 3J-O | HaloTag-Sox2 | TMR | Nikon 100x NA 1.41 | 100x | 160 | 561 |
| FIG. 3P | TOMM20-mEos3.2 | none | Olympus 100x NA 1.4 | 166.67x | 96 | 555 |
| FIG. 3Q | clathrin-HaloTag | PA-JF$_{549}$ | Zeiss 100x NA 1.46 | 160x | 100 | 561 |
| FIG. 3R | enconsin-HaloTag | PA-JF$_{549}$ | Zeiss 100x NA 1.46 | 160x | 100 | 561 |
| FIG. 3S | Sec61β-HaloTag | PA-JF$_{549}$ | Zeiss 100x NA 1.46 | 160x | 100 | 561 |
| FIG. 4F | histone H2B-HaloTag | PA-JF$_{646}$ | Olympus 60x NA 1.49 TIRF | 100x | 160 | 639 |
| FIG. 4G | TOMM20-HaloTag | PA-JF$_{646}$ | Olympus 60x NA 1.49 TIRF | 100x | 160 | 639 |
| FIG. 4J | histone H2B-SNAP-tag | PA-JF$_{646}$ | Olympus 60x NA 1.49 TIRF | 100x | 160 | 639 |
| FIG. 4K | HaloTag-Sox2 | PA-JF$_{549}$ | Olympus 60x NA 1.49 TIRF | 100x | 160 | 555 |
| FIG. 4L | vimentin-HaloTag | PA-JF$_{646}$ | Zeiss 100x NA 1.46 | 160x | 100 | 642 |
| FIG. 4M | TOMM20-HaloTag | PA-JF$_{646}$ | Olympus 100x NA 1.4 | 166.67x | 96 | 639 |

| Figure panel | Excitation intensity* (kW/cm$^2$) | Imaging geometry | Live vs. fixed | Microscope Type | Exposure time (ms) | Emission filter |
|---|---|---|---|---|---|---|
| FIGS. 1D-F | 1.7 | HILO | live | custom (English et. al. SPIE 2015) | 20 | English et. al. SPIE 2015 |

TABLE 2-continued

Comprehensive Listing of Instrumental Properties

| FIGS. 1E-F | 1.7 | HILO | live | custom (English et. al.SPIE 2015) | 20 | English et. al.SPIE 2015 |
| --- | --- | --- | --- | --- | --- | --- |
| FIGS. 1G-I | 4 | epi | fixed | custom (English et. al.SPIE 2015) | 50 | English et. al.SPIE 2015 |
| FIGS. 1H-I | 4 | epi | fixed | custom (English et. al.SPIE 2015) | 50 | English et. al.SPIE 2015 |
| FIG. 2B | 1.7 | HILO | live | custom (English et. al.SPIE 2015) | 20 | English et. al.SPIE 2015 |
| FIG. 2B | 1.7 | HILO | live | custom (English et. al.SPIE 2015) | 20 | English et. al.SPIE 2015 |
| FIGS. 2C-G | 1.7 | HILO | live | custom (English et. al.SPIE 2015) | 10 | English et. al. SPIE 2015 |
| FIGS. 2C-G | 1.7 | HILO | live | custom (English et. al.SPIE 2015) | 10 | English et. al.SPIE 2015 |
| FIG. 2H | 1.7 | HILO | fixed | custom (English et. al.SPIE 2015) | 50 | English et. al.SPIE 2015 |
| FIG. 2H | 1.7 | HILO | fixed | custom (English et. al.SPIE 2015) | 50 | English et. al.SPIE 2015 |
| FIG. 3G | 0.17 | epi | live | custom (English et. al.SPIE 2015) | 300 | English et. al.SPIE 2015 |
| FIG. 3G | 0.17 | epi | live | custom (English et. al.SPIE 2015) | 300 | English et. al.SPIE 2015 |
| FIG. 3H | 4 | HILO | fixed | custom (English et. al.SPIE 2015) | 300 | English et. al.SPIE 2015 |
| FIG. 3H | 4 | HILO | fixed | custom (English et. al.SPIE 2015) | 300 | English et. al.SPIE 2015 |
| FIG. 3I | 4 | TIRF | fixed | custom (English et. al.SPIE 2015) | 50 | English et. al.SPIE 2015 |
| FIG. 3I | 4 | TIRF | fixed | custom (English et. al.SPIE 2015) | 50 | English et. al.SPIE 2015 |
| FIG. 3J-O | 1.5 | Multifocal + HILO | live | custom (Abrahamsson et. al.2016) | 30 | Abrahamsson et. al. Biomed Opt Express 2016 |
| FIG. 3J-O | 1.5 | Multifocal + HILO | live | custom (Abrahamsson et. al.2016) | 30 | Abrahamsson et. al. Biomed Opt Express 2016 |
| FIG. 3P | 4 | epi | fixed | custom (English et. al.SPIE 2015) | 50 | English et. al.SPIE 2015 |
| FIG. 3Q | 2.5 | TIRF | fixed | Zeiss Elyra | 100 | LBF-561/642 |
| FIG. 3R | 2.5 | HiLo | fixed | Zeiss Elyra | 100 | LBF-561/642 |
| FIG. 3S | 2.5 | HiLo | fixed | Zeiss Elyra | 100 | LBF-561/642 |
| FIG. 4F | 0.17 | epi | live | custom (English et. al.SPIE 2015) | 300 | English et. al.SPIE 2015 |
| FIG. 4G | 4 | HILO | fixed | custom (English et. al.SPIE 2015) | 300 | English et. al.SPIE 2015 |
| FIG. 4J | 1.7 | HILO | live | custom (English et. al.SPIE 2015) | 10 | English et. al.SPIE 2015 |
| FIG. 4K | 1.7 | HILO | live | custom (English et. al.SPIE 2015) | 10 | English et. al.SPIE 2015 |
| FIG. 4L | 2 | HiLo | fixed | Zeiss Elyra | 100 | LBF-561/642 |
| FIG. 4M | 4 | epi | fixed | custom (English et. al.SPIE 2015) | 50 | English et. al.SPIE 2015 |

TABLE 2-continued

Comprehensive Listing of Instrumental Properties

| Figure panel | Camera type | EM gain | Preamp setting | Counts/photon | Camera pixel noise | Number of frames |
|---|---|---|---|---|---|---|
| FIGS. 1D-F | Andor Ultra 897 (DU-897-CS0-BV) | 400 | 3 | 83.16 | 81.9 | 20,000 |
| FIGS. 1E-F | Andor Ultra 897 (DU-897-CS0-BV) | 400 | 3 | 83.16 | 81.9 | 20,000 |
| FIGS. 1G-I | Andor Ultra 897 (DU-897-CS0-BV) | 400 | 3 | 83.16 | 81.9 | 20,000 |
| FIGS. 1H-I | Andor Ultra 897 (DU-897-CS0-BV) | 400 | 3 | 83.16 | 81.9 | 20,000 |
| FIG. 2B | Andor Ultra 897 (DU-897-CS0-BV) | 400 | 3 | 83.16 | 81.9 | 10,000 |
| FIG. 2B | Andor Ultra 897 (DU-897UCS0-EXF) | 400 | 3 | 78.43 | 76.64 | 10,000 |
| FIGS. 2C-G | Andor Ultra (DU-897UCS0-EXF) | 400 | 3 | 78.43 | 76.64 | 15,000 |
| FIGS. 2C-G | Andor Ultra (DU-897-CS0-BV) | 400 | 3 | 83.16 | 81.9 | 15,000 |
| FIG. 2H | Andor Ultra (DU-897UCS0-EXF) | 400 | 3 | 78.43 | 76.64 | 10,000 |
| FIG. 2H | Andor Ultra (DU-897-CS0-BV) | 400 | 3 | 83.16 | 81.9 | 10,000 |
| FIG. 3G | Andor Ultra (DU-897-CS0-BV) | 25 | 3 | 5.2 | 81.9 | 1000 |
| FIG. 3G | Andor Ultra (DU-897-CS0-BV) | 25 | 3 | 5.2 | 81.9 | 1000 |
| FIG. 3H | Andor Ultra (DU-897-CS0-BV) | 25 | 3 | 5.2 | 81.9 | 10,000 |
| FIG. 3H | Andor Ultra (DU-897-CS0-BV) | 25 | 3 | 5.2 | 81.9 | 10,000 |
| FIG. 3I | Andor Ultra (DU-897-CS0-BV) | 400 | 3 | 83.16 | 81.9 | 2,000 |
| FIG. 3I | Andor Ultra (DU-897-CS0-BV) | 400 | 3 | 83.16 | 81.9 | 2,000 |
| FIG. 3J-O | Andor Ultra (DU-897-CS0-BV) | 300 | 1 | 20.17 | 235.52 | 4,000 |
| FIG. 3J-O | Andor Ultra (DU-897-CS0-BV) | 300 | 1 | 20.17 | 235.52 | 4,000 |

TABLE 2-continued

Comprehensive Listing of Instrumental Properties

| FIG. | Camera | | | | | |
|---|---|---|---|---|---|---|
| FIG. 3P | Andor Ultra (DU-897-CS0-BV) | 400 | 3 | 83.16 | 81.9 | 20,000 |
| FIG. 3Q | Andor Ultra 897 | 300 | n/a | n/a | n/a | 7,000 |
| FIG. 3R | Andor Ultra 897 | 300 | n/a | n/a | n/a | 10,000 |
| FIG. 3S | Andor Ultra 897 | 300 | n/a | n/a | n/a | 16,400 |
| FIG. 4F | Andor Ultra (DU-897UCS0-EXF) | 25 | 3 | 4.9 | 76.64 | 1000 |
| FIG. 4G | Andor Ultra (DU-897UCS0-EXF) | 25 | 3 | 4.9 | 76.64 | 10,000 |
| FIG. 4J | Andor Ultra (DU-897UCS0-EXF) | 400 | 3 | 78.43 | 76.64 | 15,000 |
| FIG. 4K | Andor Ultra (DU-897-CS0-BV) | 400 | 3 | 83.16 | 81.9 | 15,000 |
| FIG. 4L | Andor Ultra 897 | 300 | n/a | n/a | n/a | 2,800 |
| FIG. 4M | Andor Ultra (DU-897UCS0-EXF) | 400 | 3 | 78.43 | 76.64 | 20,000 |

Cell Culture. Mouse D3 ES cells (ATCC) were maintained on 0.1% w/v gelatin coated plates in the absence of feeder cells. The ES cell medium was prepared by supplementing knockout Dulbecco's modified eagles media (DMEM, Invitrogen) with 15% v/v fetal bovine serum (FBS), 1 mM glutamax, 0.1 mM nonessential amino acids, 1 mM sodium pyruvate, 0.1 mM 2-mercaptoethanol, and 1000 units of leukemia inhibitory factor (LIF; Millipore). U2OS (ATCC) and COS-7 (ATCC) cells were cultured in DMEM (Corning) with 10% v/v fetal bovine serum (FBS) supplemented with 2 mM L-glutamine or 2 mM GlutaMAX. Cells were regularly tested for mycoplasma contamination by the Janelia Cell Culture Facility.

Plasmid Construction. Sox2 and histone H2B cDNA were amplified from ES cell cDNA libraries. Htt-94Q cDNA was obtained from Addgene (Plasmid #23966). The full-length cDNAs were cloned into the Piggybac transposon vector (PB533A-2, System Biosciences) or a modified Piggybac transposon vector with PuroR. The sequence for HaloTag (Promega) or mEos3.2 (Addgene: Plasmid #54525) was ligated in-frame with the cDNA of the desired proteins at the N-terminus (HaloTag-Sox2) or C-terminus (histone H2B-HaloTag, histone H2B-SNAP-tag, and Htt-94Q-mEos3.2-NLS). The plasmids coding ensconsin-HaloTag, clathrin-HaloTag, TOMM20-HaloTag, Sec61β-HaloTag, and vimentin-HaloTag were constructed by substituting the sequence for the HaloTag for the sequence of mEmerald. Each plasmid was transiently transfected into U2OS cells using the Nucleofactor Kit (Lonza).

Stable Cell Line Generation. Stable cell lines were generated by co-transfection of Piggybac transposon vector with a helper plasmid that over-expresses Piggybac transposase (Super Piggybac Transposase, System Biosciences). At 48 h post-transfection, cells were subjected to neomycin or puromycin (Invitrogen) selection. Transfection was conducted by using the Nucleofector system (Lonza).

ES Cell Labeling Strategy and Preparation for Imaging. One day before imaging, ES cells were plated onto a cover slip pre-coated with IMatrix-511 (Clontech). Imaging was performed in the ES cell imaging medium, which was prepared by supplementing FluoroBrite medium (Invitrogen) with 10% v/v FBS, 1 mM glutamax, 0.1 mM nonessential amino acids, 1 mM sodium pyruvate, 10 mM HEPES (pH 7.2-7.5), 0.1 mM 2-mercaptoethanol, and 1000 units of LIF (Millipore). For PA-JF$_{549}$ or PA-JF$_{646}$ labeling, cells were incubated with PA-JF$_{549}$-HaloTag ligand (6) or PA-JF$_{646}$-HaloTag ligand (16) at a final concentration of 100 nM for 1 h. For the 2-color sptPALM live-cell tracking experiments, labeled cells were washed with ES cell imaging medium (3×) before imaging. For the 2-color fixed-cell PALM imaging experiments, labeled cells were washed with PBS (4×), fixed in 4% w/v paraformaldehyde for 10 min and washed with PBS (3×). The final PALM imaging was performed in PBS solution.

3D spt-dSTORM and spt-PALM tracking experiments. Fluorescently tagged HaloTag-Sox2 molecules labeled either with PA-JF$_{549}$-HaloTag ligand (6) or with TMR-HaloTag ligand (9) were tracked in live ES cells in 3D using a custom-built multifocus microscope.[15] The fluorescence from nine focal planes was simultaneously recorded using an iXon Ultra EMCCD camera (DU-897U-CS0-#BV, 17 MHz EM amplifiers, pre-amp setting 1, Gain 300) at a frame time of 30 ms.

One-color PALM labeling and fixation. Cells were grown on pre-cleaned 25 mm diameter coverslips or pre-cleaned 25-mm diameter coverslips embedded with containing gold-nanorods as fiducial markers (generous gift of Gleb Shtengel, Janelia). Before fixation, cells were labeled with 10 nM of the HaloTag ligand for 30 min at 37° C., 5% CO$_2$. Cells were then washed three times with pre-warmed DMEM buffer containing 10% FBS. Before fixation, the coverslips were washed twice with pre-warmed PBS solution without magnesium chloride or calcium chloride. 1 mL of 8% formaldehyde solution in PBS was slowly added to a dish containing 1 mL of PBS, and the resulting 4% formaldehyde solution was incubated at room temperature for 10 min. The coverslips were washed twice with PBS and incubated in 0.1% v/v Triton X-100 in PBS solution for 4 min. The coverslips were washed twice in PBS, and then incubated in 1% w/v BSA in PBS for 1 h at ambient temperature. After washing twice more with PBS, the coverslips were mounted into metal cell chambers for PALM imaging.

Two-color sptPALM live-cell tracking experiments. ES cells expressing both HaloTag-Sox2 fusions labeled with PA-JF$_{549}$-HaloTag ligand (6) and SNAP-tag-histone H2B fusions labeled with PA-JF$_{646}$-SNAP-tag ligand (17) were tracked simultaneously using a custom-built 3-camera microscope.[21] Two iXon Ultra EMCCD cameras (DU-897-CSO-BV and DU-897U-CSO-EXF, both cooled to −80° C., 17 MHz EM amplifiers, pre-amp setting 3, gain 400) were synchronized using a National Instruments DAQ board (NI-DAQ-USB-6363) at a frame time of 10 ms. 5 ms stroboscopic excitations of a 555 nm laser (CL555-1000-O with TTL modulation, CrystaLaser) and a 639 nm laser (Stradus 637-140, Vortran) were synchronized to the frame times of the two respective cameras via LabVIEW 2012 (National Instruments). The two lasers stroboscopically illuminated the sample using peak power densities of ~1.7 kW/cm$^2$ using HiLo illumination of the nucleus. The PA-JF$_{549}$ and PA-JF$_{646}$ labels were photoconverted by 100 µs long excitation pulses of 407 nm light (50 W/cm$^2$) every second. During the course of image acquisition, the pulse length was increased to 200 µs long pulses. During imaging, cells were maintained at 37° C. and 5% CO$_2$ using a Tokai-hit stage top incubator and objective heater. We determined colocalized Sox2 and histone H2B trajectories in our live cell experiment using an analysis published previously. Briefly, we localized particles and build trajectories in both channels separately. We then assigned as colocalized trajectories that dwelled within 320 nm of one another for at least 10 ms. We then calculated diffusion coefficients maps and histograms as described in Grimm, English et al.

Determination of Background Staining. COS-7 cells were stably transfected with a plasmid expressing a human histone H2B-HaloTag protein fusion. Untransfected COS-7 cells and the stable histone H2B-HaloTag expressing cells were plated into 35 mm MatTek glass bottom dishes at 2×10$^5$ cells per plate in phenol red-free DMEM with 10% FBS and GlutaMAX. After 24 h, cells were rinsed with PBS and fixed with 2 mL of fresh 4% w/v paraformaldehyde in 0.1 M phosphate buffer, pH 7.4 for 30 min, followed by two washes with PBS. The histone H2B-HaloTag protein was stained with 100 nM of either PA-JF$_{549}$-HaloTag ligand (6) or PA-JF$_{646}$-HaloTag ligand (16) for 30 min, along with 5 µg/mL Hoechst 33342 (Invitrogen) in PBS. The cells were then washed twice with PBS, washed for 20 min with PBS containing 0.1% v/v Triton X-100 and 3% w/v BSA, followed by two more washes with PBS. Cells were imaged using a Zeiss 710 LSM. Z-dimension stack boundaries were set using the Hoechst 33342 nuclear reference stain, which was imaged using 405 nm excitation and 410-485 nm emission. Partial photoactivation of PA-JF$_{549}$ and PA-JF$_{646}$ was accomplished with 60 iterations of 405 nm set at 75% laser power. Images for activated JF$_{549}$ were collected using 561 nm excitation and 566-685 nm emission. Images for JF$_{646}$ were collected using 633 nm excitation and 638-759 nm emission. The Hoechst 33342 and JF-dye tracks were collected separately. Image analysis was done using Fiji. Confocal stacks are displayed as maximum projection images. The experimental and control images were set to the same brightness/contrast scales.

Two-color fixed-cell PALM imaging acquisition. ES cells expressing both Htt94Q-mEos3.2 and histone H2B-HaloTag labeled with PA-JF$_{646}$-HaloTag ligand (16) were imaged using the previously described custom-built 3-camera microscope at a frame time of 50 ms and a constant illumination power density of around 4 kW/cm$^2$ for both 555 nm and 639 nm excitation lasers. mEos3.2 and PA-JF$_{646}$ were photoconverted by 100 µs long excitation pulses of 407 nm light (100 W/cm$^2$) every second. The mEos3.2 emitted 115.6 detected photons/localization/frame and molecules emit on average for 4 frames, as determined by tracking using stringent displacement parameters to select immobile particles. Thus, each mEos3.2 emits approximately 460 detected photons, consistent with literature reports. The 1.7-fold higher resolution enhancement afforded by JF$_{646}$ is smaller than expected based on the 6.5-fold more detected photons/localization/frame (757.6) and the red-shifted spectra of JF$_{646}$. This is primarily due to the camera pixel size being optimized for the dimmer protein fluorophore and the increased fluorescence background generated by bright out-of-focus JF$_{646}$ molecules.

PALM and sptPALM tracking image analysis. For simultaneous 2-camera imaging and tracking, the two 16-bit TIFF stacks were registered using the similarity (2d) transformation model using a descriptor-based Fiji plugin. Super-resolution images were rendered using the software package Localizer by Dedecker et al. with 8-way adjacency particle detection, 20 GLRT sensitivity, and a PSF of 1.3 pixels. The following settings were chosen for particle track linking: 5 pixel maximum jump distance, 3-frame minimum track length, and 15 GLRT sensitivity. Resulting tracks were then exported as text files, and diffusion mapping was performed with code written in Igor Pro 6.36 (WaveMetrics). The code calculates local apparent diffusion coefficients evaluated in 20 nm by 20 nm grids from the mean square displacements over the frame-time timescale. Zeiss Zen 2.1 software was used to analyze images taken from Zeiss Elyra microscope.

Multifocus image processing. We assembled 3D stacks by aligning the nine simultaneously obtained focal planes on top of one another using bead calibration data as described previously. For 3D particle tracking we imported the 16-bit TIFF stack into DiaTrack 3.04 Pro, which identifies and fits the intensity spots with 3D Gaussian function matched to a pre-determined PSF. The following settings were chosen for 3D particle tracking: Subtract background, Filter data of 1.05, PSF of 1.3 pixels, remove dim of 15, and remove blurred of 0.05. Resulting 3D tracks were exported with code written in Igor Pro 6.36 as one text file containing frame numbers, as well as x, y, and z-coordinates of all detected points. We plotted a map of all detected particle locations in the x-y plane, color-coded for height (z), and calculated histograms of detected number of particles over the course of 3D sptPALM data acquisitions. Integrated fluorescence intensities from particles detected in the central two focal planes (multifocal plane 4 and 5) were calculated and converted to photon counts using analysis routines written in Igor Pro version 6.36. Localization errors were calculated using equation (6) in Mortensen et al.

Activation rate measurement. Live U2OS cells expressing either histone H2B-mEos3.2 or histone H2B-HaloTag labeled with ligands 6 and 16 (n=5 cells for each fluorophore) were imaged under concurrent excitation light (561 nm for PA-JF$_{549}$ and mEos3.2; 637 nm for PA-JF$_{646}$) and activation light (405 nm) for 300 s (300 ms per frame). The time constants (τ) were determined by an exponential fit of fluorescence vs. time (FIGS. 3G and 4F).

On-off ratio and photon count estimate. The on-off ratio was determined using the method of Wang et al. and a summary of the data given in Table 1. Briefly, U2OS cells expressing either TOMM20-mEos3.2 or TOMM20-HaloTag labeled with ligands 6 and 16 were fixed in 4% PFA for 10 minutes and then washed as described above. The cells were then imaged in PBS with the excitation laser only (561 nm for PA-JF$_{549}$ and mEos3.2; 637 nm for PA-JF$_{646}$; 300 ms per frame) (FIGS. 3H and 4G). After ~300 frames, the photoactivation laser (405 nm) was turned on, and the intensity was gradually increased until exhaustion of the photoactivation process. Fluorescent spots were counted using custom software (Airlocalize).

The on-rate was computed as the average number of photoactivated spots per frame during the pre-photoactivation phase, divided by the total number of fluorescent spots detected over the entire movie. To measure the off-rate, the spots from the pre-photoactivation phase were first isolated. Within these, spots separated by less than 1 pixel were assembled in a trajectory corresponding to an individual molecule. The 1 pixel threshold value was determined based on the width of the pair-correlation function computed over all spots in the photoactivation phase. To obtain μ, the average fluorophore lifetime in frames (the inverse of the off-rate), the distribution of the number of frames n per molecule was then fitted to an integrated exponential (equation 1):

$$p(n) = \int_{n-1}^{n} \frac{1}{\mu} \exp\left(-\frac{u}{\mu}\right) du. \quad (1)$$

Finally the on-off ratio was computed as the product of the on-rate by the average fluorophore lifetime. Each value is the average of 2-4 separate cells. In this regard, it is noted that the estimate of the on-off ratio mEos3.2 fixed cells was higher than a previous live-cell measurement. This difference in photophysics likely stems from difference in experimental conditions (PBS vs. living cell). From these experiments the total number of detected photons/molecule was also computed by summing the spot intensities for each molecule, and adjusting the result for the gain conversion factor of the EM-CCD (FIG. 3I).

Characterization of blinking kinetics of PA-JF$_{549}$-HaloTag ligand during PALM imaging. A section of the PALM imaging movie was selected from the ensconsin-HaloTag-PA-JF$_{549}$ experiment (FIG. 3R) that featured a low density of emitters. Their positions were determined using a 2-dimensional Gaussian mask localization algorithm on the maximum intensity projection of the movie section. Subsequently, the same localization software was run on the individual frames of the movie and a time trajectory for each spot identified in the maximum intensity projection was generated: if a spot was detected on a given frame within 1 pixel of the spot identified in the maximum projection, they were assumed to represent the same particle and the corresponding position, intensity and frame number were included in the time trajectory. A threshold of 1 pixel was chosen to account for drift; based on a cross-correlation analysis, the drift was estimated to contribute less ~0.25 pixel displacement in each dimension over the duration of the movie. It is noted that the conservative choice of the threshold might result in a small fraction of false positive blinking events, and therefore the measurements likely slightly overestimate the dyes propensity to blink. Using the time trajectory of each particle, individual blinking events were isolated and quantified. The resulting statistics demonstrate that PA-JF$_{549}$ fluorophores exhibit little blinking (on average 1.4 blinking event, FIGS. 3T-V).

Example 2

General Experimental Information for Synthesis

Commercial reagents were obtained from reputable suppliers and used as received. All solvents were purchased in septum-sealed bottles stored under an inert atmosphere. All reactions were sealed with septa through which a nitrogen atmosphere was introduced unless otherwise noted. Reactions were conducted in round-bottomed flasks or septum-capped crimp-top vials containing Teflon-coated magnetic stir bars. Heating of reactions was accomplished with a silicon oil bath or an aluminum reaction block on top of a stirring hotplate equipped with an electronic contact thermometer to maintain the indicated temperatures.

Reactions were monitored by thin layer chromatography (TLC) on precoated TLC glass plates (silica gel 60 F$_{254}$, 250 μm thickness) or by LC/MS (Phenomenex Kinetex 2.1 mm×30 mm 2.6 μm C18 column; 5 μL injection; 5-98% MeCN/H$_2$O, linear gradient, with constant 0.1% v/v HCO$_2$H additive; 6 min run; 0.5 mL/min flow; ESI; positive ion mode). TLC chromatograms were visualized by UV illumination or developed with p-anisaldehyde, ceric ammonium molybdate, or KMnO$_4$ stain. Reaction products were purified by flash chromatography on an automated purification system using pre-packed silica gel columns or by preparative HPLC (Phenomenex Gemini-NX 30×150 mm 5 μm C18 column). Analytical HPLC analysis was performed with an Agilent Eclipse XDB 4.6×150 mm 5 μm C18 column under the indicated conditions. High-resolution mass spectrometry was obtained by the High Resolution Mass Spectrometry Facility at the University of Iowa.

NMR spectra were recorded on a 400 MHz spectrometer. $^1$H and $^{13}$C chemical shifts (δ) were referenced to TMS or residual solvent peaks, and $^{19}$F chemical shifts (δ) were referenced to CFCl$_3$. Data for $^1$H NMR spectra are reported as follows: chemical shift (δ ppm), multiplicity (s=singlet, d=doublet, t=triplet, q=quartet, dd=doublet of doublets, m=multiplet), coupling constant (Hz), integration. Data for $^{13}$C NMR spectra are reported by chemical shift (δ ppm) with hydrogen multiplicity (C, CH, CH$_2$, CH$_3$) information obtained from DEPT spectra.

Synthesis of PA-JF Probes

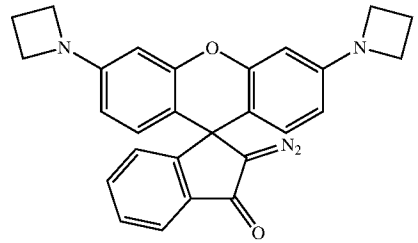

PA-JF$_{549}$ (2) (FIGS. 1A, 8, and 10A): To a solution of Janelia Fluor 549[1] (JF$_{549}$) (1) (450 mg, 1.10 mmol) in CH$_2$Cl$_2$ (30 mL) was added oxalyl chloride (111 μL, 1.32 mmol, 1.2 eq). After stirring the reaction at room temperature for 30 min, triethylamine (229 µL, 1.64 mmol, 1.5 eq) and (trimethylsilyl)diazomethane (2.0 M in Et$_2$O, 3.29 mL, 6.58 mmol, 6 eq) were added in succession. The reaction was stirred at room temperature for 1 h, concentrated in vacuo, and purified by flash chromatography on silica gel (0-20% EtOAc/toluene, linear gradient) to afford 333 mg (70%) of 2 as a yellow solid. $^1$H NMR (CDCl$_3$, 400 MHz) δ 7.83-7.79 (m, 1H), 7.46 (td, J=7.5, 1.3 Hz, 1H), 7.39 (td, J=7.4, 1.0 Hz, 1H), 7.07-7.03 (m, 1H), 6.69 (d, J=8.5 Hz, 2H), 6.16 (d, J=2.3 Hz, 2H), 6.07 (dd, J=8.5, 2.3 Hz, 2H), 3.88 (t, J=7.5 Hz, 8H), 2.36 (p, J=7.2 Hz, 4H); $^{13}$C NMR (CDCl$_3$, 101 MHz) δ 187.4 (C), 156.4 (C), 152.7 (C), 152.1 (C), 134.69 (CH), 134.66 (C), 128.8 (CH), 128.4 (CH), 125.5 (CH), 122.3 (CH), 109.7 (C), 107.9 (CH), 98.3 (CH), 77.4 (C), 52.3 (CH$_2$), 49.4 (C), 16.9 (CH$_2$); HRMS (ESI) calcd for C$_{27}$H$_{23}$N$_4$O$_2$ [M+H]$^+$ 435.1816, found 435.1820.

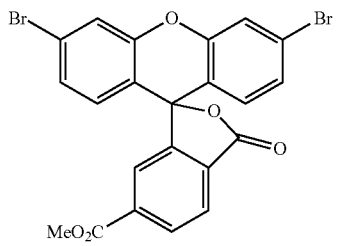 [SMILES: COC(=O)c1ccc2c(c1)C1(OC2=O)c2ccc(Br)cc2Oc2cc(Br)ccc21]

3',6'-Dibromo-6-methoxycarbonylfluoran (S2) (FIG. 5): 3',6'-Dibromo-6-carboxyfluoran[2] (S1) (1.50 g, 2.99 mmol) was suspended in MeOH (50 mL), and H$_2$SO$_4$ (293 mg, 2.99 mmol, 1 eq) was added. The reaction was stirred at reflux for 72 h. It was subsequently concentrated in vacuo, and the resulting residue was diluted with saturated NaHCO$_3$ and extracted with 15% i-PrOH/CHCl$_3$ (2×). The combined organic extracts were dried over anhydrous MgSO$_4$, filtered, and evaporated. Silica gel chromatography (0-10% EtOAc/hexanes, linear gradient, with constant 40% v/v CH$_2$Cl$_2$) yielded 1.49 g (97%) of S2 as a white solid. $^1$H NMR (CDCl$_3$, 400 MHz) δ 8.31 (dd, J=8.0, 1.3 Hz, 1H), 8.10 (dd, J=8.0, 0.7 Hz, 1H), 7.76 (dd, J=1.2, 0.8 Hz, 1H), 7.52 (d, J=1.9 Hz, 2H), 7.20 (dd, J=8.5, 1.9 Hz, 2H), 6.68 (d, J=8.5 Hz, 2H), 3.89 (s, 3H); $^{13}$C NMR (CDCl$_3$, 101 MHz) δ 168.1 (C), 165.3 (C), 153.1 (C), 151.2 (C), 137.0 (C), 131.6 (CH), 129.24 (C), 129.21 (CH), 127.8 (CH), 125.7 (CH), 125.1 (CH), 124.6 (C), 120.7 (CH), 117.4 (C), 81.5 (C), 53.0 (CH$_3$); HRMS (ESI) calcd for C$_{22}$H$_{13}$Br$_2$O$_5$ [M+H]$^+$ 514.9124, found 514.9141.

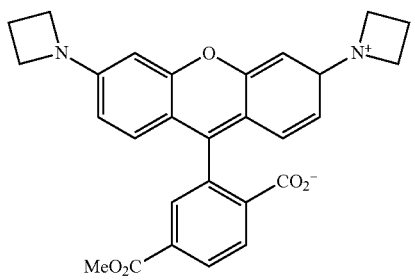

6-Methoxycarbonyl-JF$_{549}$ (S3) (FIG. 5): A vial was charged with S2 (400 mg, 775 µmol), Pd$_2$dba$_3$ (71 mg, 77.5 µmol, 0.1 eq), XPhos (111 mg, 232 µmol, 0.3 eq), and Cs$_2$CO$_3$ (707 mg, 2.17 mmol, 2.8 eq). The vial was sealed and evacuated/backfilled with nitrogen (3×). Dioxane (6 mL) was added, and the reaction was flushed again with nitrogen (3×). Following the addition of azetidine (115 µL, 1.70 mmol, 2.2 eq), the reaction was stirred at 100° C. for 3 h. It was then cooled to room temperature, diluted with MeOH, deposited onto Celite, and concentrated to dryness. Purification by silica gel chromatography (0-10% MeOH (2 M NH$_3$)/CH$_2$Cl$_2$, linear gradient; dry load with Celite) afforded S3 (312 mg, 86%) as a purple solid. $^1$H NMR (MeOD, 400 MHz) δ 8.24 (dd, J=8.1, 1.7 Hz, 1H), 8.12 (dd, J=8.1, 0.4 Hz, 1H), 7.83-7.80 (m, 1H), 7.16 (d, J=9.2 Hz, 2H), 6.56 (dd, J=9.2, 2.2 Hz, 2H), 6.48 (d, J=2.2 Hz, 2H), 4.32-4.22 (m, 8H), 3.90 (s, 3H), 2.54 (p, J=7.6 Hz, 4H); Analytical HPLC: t$_R$=12.7 min, >99% purity (5 µL injection; 10-95% MeCN/H$_2$O, linear gradient, with constant 0.1% v/v TFA additive; 20 min run; 1 mL/min flow; ESI; positive ion mode; UV detection at 550 nm); HRMS (ESI) calcd for C$_{28}$H$_{25}$N$_2$O$_5$ [M+H]$^+$ 469.1758, found 469.1766.

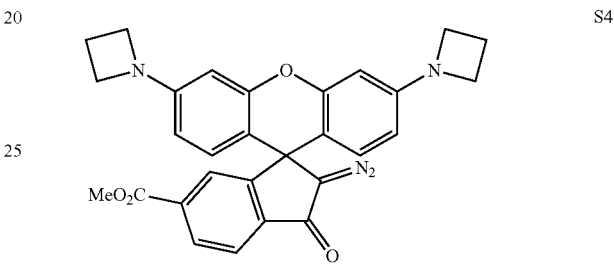

6-Methoxycarbonyl-PA-JF$_{549}$ (S4) (FIG. 5): The procedure described for 2 was used to convert S3 into the title compound (38%, yellow solid). $^1$H NMR (CDCl$_3$, 400 MHz) δ 8.07 (dd, J=8.0, 1.4 Hz, 1H), 7.87 (dd, J=8.0, 0.6 Hz, 1H), 7.68 (dd, J=1.4, 0.6 Hz, 1H), 6.66 (d, J=8.5 Hz, 2H), 6.18 (d, J=2.3 Hz, 2H), 6.07 (dd, J=8.5, 2.4 Hz, 2H), 3.96-3.84 (m, 8H), 3.82 (s, 3H), 2.37 (p, J=7.2 Hz, 4H); $^{13}$C NMR (CDCl$_3$, 101 MHz) δ 186.2 (C), 166.2 (C), 156.3 (C), 152.8 (C), 152.2 (C), 138.4 (C), 135.8 (C), 129.8 (CH), 128.7 (CH), 126.9 (CH), 122.3 (CH), 108.8 (C), 108.0 (CH), 98.5 (CH), 78.4 (C), 52.5 (CH$_3$), 52.3 (CH$_2$), 49.5 (C), 16.9 (CH$_2$); HRMS (ESI) calcd for C$_{29}$H$_{25}$N$_4$O$_4$ [M+H]$^+$ 493.1870, found 493.1877.

PA-JF$_{549}$-NHS (S5) (FIG. 5): To a solution of S4 (53 mg, 108 µmol) in 2:1 MeOH/THF (7.5 mL) under nitrogen was added 1 M NaOH (538 µL, 538 µmol, 5 eq). The reaction was stirred at room temperature for 24 h. It was subsequently acidified with 1 M HCl (575 µL), diluted with water, and extracted with CH$_2$Cl$_2$ (2×). The organic extracts were dried over anhydrous MgSO$_4$, filtered, and concentrated in vacuo to provide the carboxylic acid as a yellow solid (47 mg, 91%).

The acid (47 mg, 98.2 µmol) was combined with TSTU (44 mg, 147 µmol, 1.5 eq) in DMF (3 mL), and DIEA (51 µL, 295 µmol, 3 eq) was added. After stirring the reaction at room temperature for 1 h, it was concentrated to dryness and deposited onto Celite. Flash chromatography on silica gel (10-100% EtOAc/hexanes, linear gradient; dry load with Celite) afforded S5 as a yellow solid (40 mg, 71%). $^1$H NMR (CDCl$_3$, 400 MHz) δ 8.16 (dd, J=8.0, 1.5 Hz, 1H), 7.93 (dd, J=8.0, 0.6 Hz, 1H), 7.75 (dd, J=1.4, 0.6 Hz, 1H), 6.66 (d, J=8.5 Hz, 2H), 6.16 (d, J=2.3 Hz, 2H), 6.09 (dd, J=8.5, 2.4 Hz, 2H), 3.90 (t, J=7.3 Hz, 8H), 2.86 (s, 4H), 2.37 (p, J=7.2 Hz, 4H); $^{13}$C NMR (CDCl$_3$, 101 MHz) δ 185.5 (C), 169.0 (C), 161.2 (C), 156.4 (C), 153.0 (C), 152.1 (C), 140.0 (C), 130.6 (CH), 130.4 (C), 128.5 (CH), 127.9 (CH), 122.8 (CH), 108.3 (CH), 108.1 (C), 98.5 (CH), 78.7 (C), 52.3 (CH$_2$), 49.7 (C), 25.8 (CH$_2$), 16.9 (CH$_2$); HRMS (ESI) calcd for C$_{32}$H$_{26}$N$_5$O$_6$ [M+H]$^+$ 576.1878, found 576.1890.

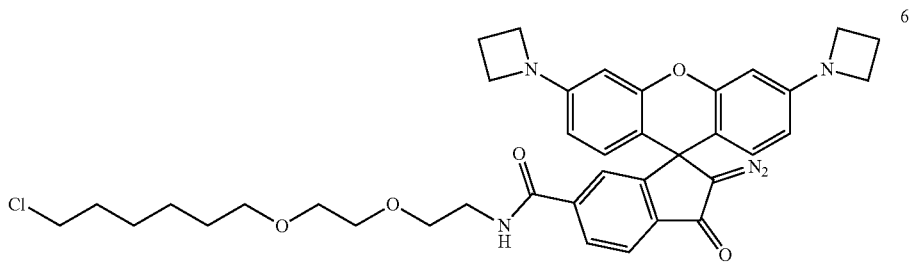

6

PA-JF$_{549}$-HaloTag ligand (6) (FIGS. 1C and 5): NHS ester S5 (15 mg, 26.1 µmol) was dissolved in DMF (1 mL). A solution of HaloTag(O2)amine (S6, 11.7 mg, 52.1 µmol, 2 eq) in DMF (250 µL) was added, followed by DIEA (22.7 µL, 130 µmol, 5 eq). After stirring the reaction at room temperature for 2 h, it was concentrated to dryness and purified by silica gel chromatography (0-100% EtOAc/toluene, linear gradient) to provide 6 as a yellow foam (15.9 mg, 89%). $^1$H NMR (CDCl$_3$, 400 MHz) δ 7.86 (dd, J=7.9, 0.6 Hz, 1H), 7.79 (dd, J=8.0, 1.5 Hz, 1H), 7.43 (dd, J=1.4, 0.6 Hz, 1H), 6.66 (d, J=8.5 Hz, 2H), 6.59 (t, J=5.1 Hz, 1H), 6.16 (d, J=2.3 Hz, 2H), 6.07 (dd, J=8.5, 2.4 Hz, 2H), 3.95-3.83 (m, 8H), 3.64-3.48 (m, 10H), 3.39 (t, J=6.6 Hz, 2H), 2.37 (p, J=7.2 Hz, 4H), 1.78-1.69 (m, 2H), 1.55-1.48 (m, 2H), 1.46-1.36 (m, 2H), 1.36-1.27 (m, 2H); Analytical HPLC: t$_R$=17.1 min, >99% purity (5 µL injection; 10-95% MeCN/H$_2$O, linear gradient, with constant 0.1% v/v TFA additive; 20 min run; 1 mL/min flow; ESI; positive ion mode; UV detection at 254 nm); HRMS (ESI) calcd for C$_{38}$H$_{43}$ClN$_5$O$_5$ [M+H]$^+$ 684.2947, found 684.2952.

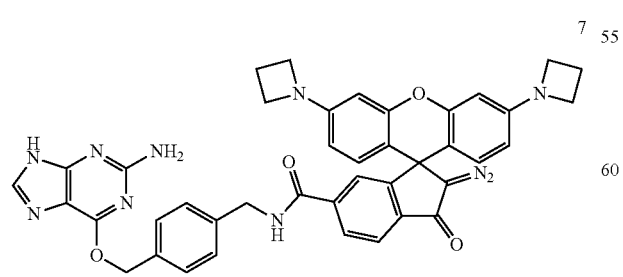

7

PA-JF$_{549}$-SNAP-tag ligand (7) (FIGS. 1C and 5): NHS ester S5 (10 mg, 17.4 µmol) and BG-NH$_2$ (S7, 7.0 mg, 26.1 µmol, 1.5 eq) were combined in DMF (1 mL), and DIEA (15.1 µL, 86.9 µmol, 5 eq) was added. After stirring the reaction at room temperature for 1 h, it was concentrated to dryness, deposited onto Celite, and purified by silica gel chromatography (0-10% MeOH/EtOAc, linear gradient; dry load with Celite) to provide 7 as a yellow solid (11.2 mg, 88%). $^1$H NMR (CD$_3$OD, 400 MHz) δ 7.94 (dd, J=8.0, 1.5 Hz, 1H), 7.85 (dd, J=8.0, 0.6 Hz, 1H), 7.80 (s, 1H), 7.53 (dd, J=1.4, 0.5 Hz, 1H), 7.37 (d, J=8.1 Hz, 2H), 7.22 (d, J=8.1 Hz, 2H), 6.64 (d, J=8.5 Hz, 2H), 6.16 (d, J=2.3 Hz, 2H), 6.12 (dd, J=8.5, 2.3 Hz, 2H), 5.46 (s, 2H), 4.43 (s, 2H), 3.90-3.77 (m, 8H), 2.34 (p, J=7.2 Hz, 4H); Analytical HPLC: t$_R$=13.0 min, >99% purity (5 µL injection; 10-95% MeCN/H$_2$O, linear gradient, with constant 0.1% v/v TFA additive; 20 min run; 1 mL/min flow; ESI; positive ion mode; UV detection at 254 nm); HRMS (ESI) calcd for C$_{41}$H$_{35}$N$_{10}$O$_4$ [M+H]$^+$ 731.2837, found 731.2852.

Figure 9:
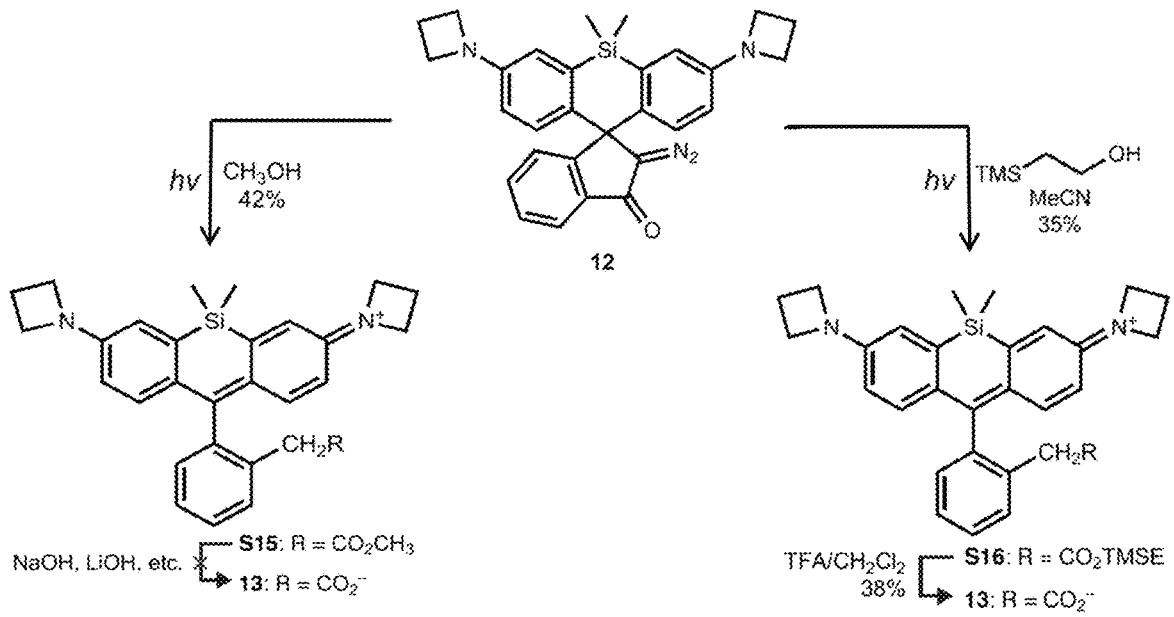
FIG. 9 shows a schematic view of the synthesis of PA-JF$_{646}$ photoproducts.

PA-JF$_{646}$ (12) (FIGS. 4A, 9, and 10B): The procedure described for 2 was used to convert Janelia Fluor 646 (JF$_{646}$) (11) into the title compound (37%, yellow solid). $^1$H NMR (CDCl$_3$, 400 MHz) δ 7.87-7.82 (m, 1H), 7.42 (td, J=7.4, 1.5 Hz, 1H), 7.37 (td, J=7.4, 1.2 Hz, 1H), 6.93-6.89 (m, 1H), 6.78 (d, J=8.8 Hz, 2H), 6.56 (d, J=2.7 Hz, 2H), 6.33 (dd, J=8.8, 2.7 Hz, 2H), 3.89 (t, J=7.4 Hz, 8H), 2.36 (p, J=7.2 Hz, 4H), 0.57 (s, 3H), 0.46 (s, 3H); $^{13}$C NMR (CDCl$_3$, 101 MHz) δ 188.4 (C), 157.8 (C), 149.9 (C), 135.2 (C), 134.6 (CH), 134.4 (C), 134.0 (C), 130.1 (CH), 127.9 (CH), 125.5 (CH), 122.6 (CH), 114.4 (CH), 114.1 (CH), 79.1 (C), 57.5 (C), 52.3 (CH$_2$), 17.0 (CH$_2$), 1.0 (CH$_3$), 0.2 (CH$_3$); HRMS (ESI) calcd for C$_{29}$H$_{29}$N$_4$OSi [M+H]$^+$ 477.2105, found 477.2104.

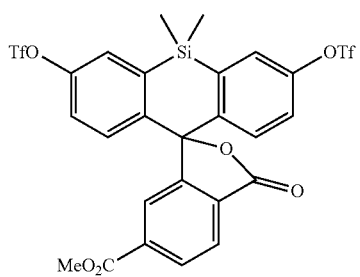 [SMILES: COC(=O)c1ccc2c(c1)C1(OC2=O)c2ccc(OS(=O)(=O)C(F)(F)F)cc2[Si](C)(C)c2cc(OS(=O)(=O)C(F)(F)F)ccc21]

6-Methoxycarbonylsilafluorescein ditriflate (S9) (FIG. 6): 6-tert-Butoxycarbonylsilafluorescein ditriflate[1] (S8; 400 mg, 541 µmol) was taken up in CH$_2$Cl$_2$ (20 mL), and trifluoroacetic acid (4 mL) was added. The reaction was stirred at room temperature for 5 h. Toluene (20 mL) was added; the reaction was concentrated to dryness and then azeotroped with MeOH three times. The resulting carboxylic acid was dissolved in 4:1 THF/MeOH (10 mL). (Trimethylsilyl)diazomethane (2.0 M in Et$_2$O, 406 µL, 812 µmol, 1.5 eq) was added, and the reaction was stirred for 15 min at room temperature. The yellow solution was then concentrated in vacuo and purified by silica gel chromatography (0-25% EtOAc/hexanes, linear gradient) to yield 344 mg (91%) of S9 as a white foam. $^1$H NMR (CDCl$_3$, 400 MHz) δ 8.28 (dd, J=8.0, 1.3 Hz, 1H), 8.08 (dd, J=8.0, 0.7 Hz, 1H), 8.03 (dd, J=1.2, 0.8 Hz, 1H), 7.58 (d, J=2.5 Hz, 2H), 7.24 (d, J=8.8 Hz, 2H), 7.20 (dd, J=8.9, 2.6 Hz, 2H), 3.95 (s, 3H), 0.81 (s, 3H), 0.71 (s, 3H); $^{19}$F NMR (CDCl$_3$, 376 MHz) δ −73.27 (s); $^{13}$C NMR (CDCl$_3$, 101 MHz) δ 168.5 (C), 165.3 (C), 152.6 (C), 149.6 (C), 144.0 (C), 138.7 (C), 136.2 (C), 131.3 (CH), 128.81 (CH), 128.75 (C), 127.0 (CH), 126.7 (CH), 125.4 (CH), 123.1 (CH), 118.9 (q, $^1J_{CF}$=320.7 Hz, C), 88.7 (C), 53.1 (CH$_3$), 0.0 (CH$_3$), −1.3 (CH$_3$); HRMS (ESI) calcd for C$_{26}$H$_{19}$F$_6$O$_{10}$S$_2$Si [M+H]$^+$ 697.0088, found 697.0097.

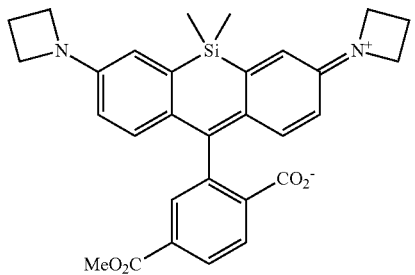

6-Methoxycarbonyl-JF$_{646}$ (S10) (FIG. 6): The procedure described for S3 was used to convert ditriflate S9 into the title compound (86%, yellow solid). $^1$H NMR (CDCl$_3$, 400 MHz) δ 8.18 (dd, J=8.0, 1.3 Hz, 1H), 7.99 (dd, J=8.0, 0.7 Hz, 1H), 7.94 (dd, J=1.2, 0.8 Hz, 1H), 6.75 (d, J=8.7 Hz, 2H), 6.66 (d, J=2.6 Hz, 2H), 6.26 (dd, J=8.7, 2.7 Hz, 2H), 3.894 (t, J=7.3 Hz, 8H), 3.892 (s, 3H), 3.95-3.83 (m, 11H), 2.36 (p, J=7.2 Hz, 4H), 0.64 (s, 3H), 0.58 (s, 3H); $^{13}$C NMR (CDCl$_3$, 101 MHz) δ 169.9 (C), 166.0 (C), 155.0 (C), 151.1 (C), 136.7 (C), 135.2 (C), 132.2 (C), 130.2 (C), 130.0 (CH), 127.8 (CH), 125.9 (CH), 125.8 (CH), 115.7 (CH), 112.5 (CH), 92.2 (C), 52.7 (CH$_3$), 52.4 (CH$_2$), 17.0 (CH$_2$), 0.4 (CH$_3$), −1.2 (CH$_3$); HRMS (ESI) calcd for C$_{34}$H$_{31}$N$_2$O$_4$Si [M+H]$^+$ 511.2048 found 511.2057.

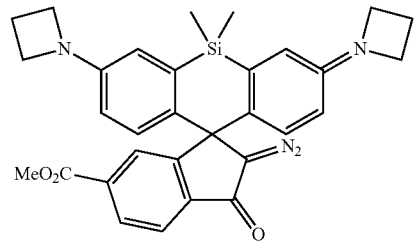

6-Methoxycarbonyl-PA-JF$_{549}$ (S11) (FIG. 6): The procedure described for 2 was used to convert S10 into the title compound (39%, yellow solid). $^1$H NMR (CDCl$_3$, 400 MHz) δ 8.03 (dd, J=8.0, 1.4 Hz, 1H), 7.88 (dd, J=8.0, 0.6 Hz, 1H), 7.58 (dd, J=1.4, 0.6 Hz, 1H), 6.80 (d, J=8.8 Hz, 2H), 6.58 (d, J=2.7 Hz, 2H), 6.33 (dd, J=8.8, 2.7 Hz, 2H), 3.94-3.85 (m, 8H), 3.80 (s, 3H), 2.36 (p, J=7.2 Hz, 4H), 0.63 (s, 3H), 0.48 (s, 3H); $^{13}$C NMR (CDCl$_3$, 101 MHz) δ 187.3 (C), 166.2 (C), 157.6 (C), 150.1 (C), 138.6 (C), 135.5 (C), 134.7 (C), 133.3 (C), 129.7 (CH), 129.2 (CH), 126.9 (CH), 122.7 (CH), 114.8 (CH), 114.1 (CH), 79.7 (C), 57.8 (C), 52.4 (CH$_3$), 52.3 (CH$_2$), 17.1 (CH$_2$), 0.9 (CH$_3$), 0.2 (CH$_3$); HRMS (ESI) calcd for C$_{31}$H$_{13}$N$_4$O$_3$Si [M+H]$^+$ 535.2160, found 535.2172.

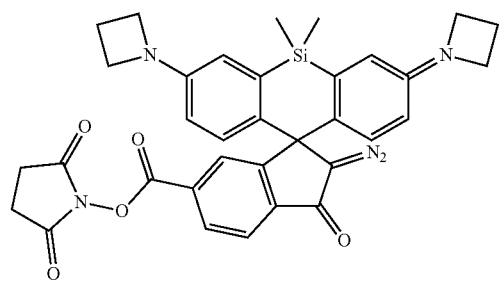

PA-JF$_{646}$-NHS (S12) (FIG. 6): The procedure described for S5 was used to convert S11 into the title compound (69% for 2 steps, yellow-orange solid). $^1$H NMR (CDCl$_3$, 400 MHz) δ 8.13 (dd, J=8.0, 1.4 Hz, 1H), 7.94 (dd, J=8.0, 0.5 Hz, 1H), 7.66-7.62 (m, 1H), 6.80 (d, J=8.8 Hz, 2H), 6.58 (d, J=2.7 Hz, 2H), 6.35 (dd, J=8.8, 2.7 Hz, 2H), 3.91 (t, J=7.4 Hz, 8H), 2.93-2.78 (m, 4H), 2.37 (p, J=7.2 Hz, 4H), 0.60 (s, 3H), 0.47 (s, 3H); $^{13}$C NMR (CDCl$_3$, 101 MHz) δ 186.6 (C), 169.1 (C), 161.2 (C), 157.7 (C), 150.3 (C), 140.2 (C), 134.6 (C), 132.5 (C), 130.1 (C), 129.9 (CH), 129.6 (CH), 127.8 (CH), 123.1 (CH), 115.0 (CH), 114.4 (CH), 80.2 (C), 57.9 (C), 52.4 (CH$_2$), 25.7 (CH$_2$), 17.0 (CH$_2$), 0.8 (CH$_3$), 0.3 (CH$_3$); HRMS (ESI) calcd for C$_{34}$H$_{32}$N$_5$O$_5$Si [M+H]$^+$ 618.2167, found 618.2179.

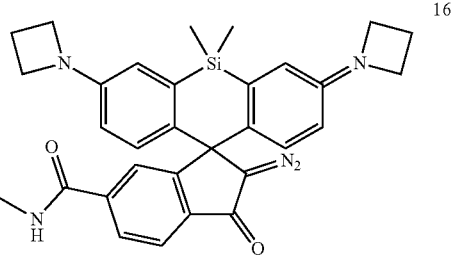

PA-JF$_{646}$-HaloTag ligand (16) (FIG. 6): The procedure described for 5 was used to convert S12 into the title compound (74%, yellow solid). $^1$H NMR (CDCl$_3$, 400 MHz) δ 7.87 (dd, J=8.0, 0.5 Hz, 1H), 7.76 (dd, J=8.0, 1.5 Hz, 1H), 7.32 (dd, J=1.4, 0.6 Hz, 1H), 6.77 (d, J=8.8 Hz, 2H), 6.57 (d, J=2.6 Hz, 2H), 6.52 (t, J=5.0 Hz, 1H), 6.32 (dd, J=8.8, 2.7 Hz, 2H), 3.90 (t, J=7.6 Hz, 8H), 3.62-3.49 (m, 10H), 3.39 (t, J=6.6 Hz, 2H), 2.37 (p, J=7.2 Hz, 4H), 1.79-1.69 (m, 2H), 1.55-1.48 (m, 2H), 1.47-1.37 (m, 2H), 1.36-1.27 (m, 2H), 0.62 (s, 3H), 0.46 (s, 3H); Analytical HPLC: t$_R$=16.2 min, >99% purity (5 μL injection; 10-95% MeCN/H$_2$O, linear gradient, with constant 0.1% v/v TFA additive; 20 min run; 1 mL/min flow; ESI; positive ion mode; UV detection at 254 nm); HRMS (ESI) calcd for C$_{40}$H$_{49}$ClN$_5$O$_4$Si [M+H]$^+$ 726.3237, found 726.3253.

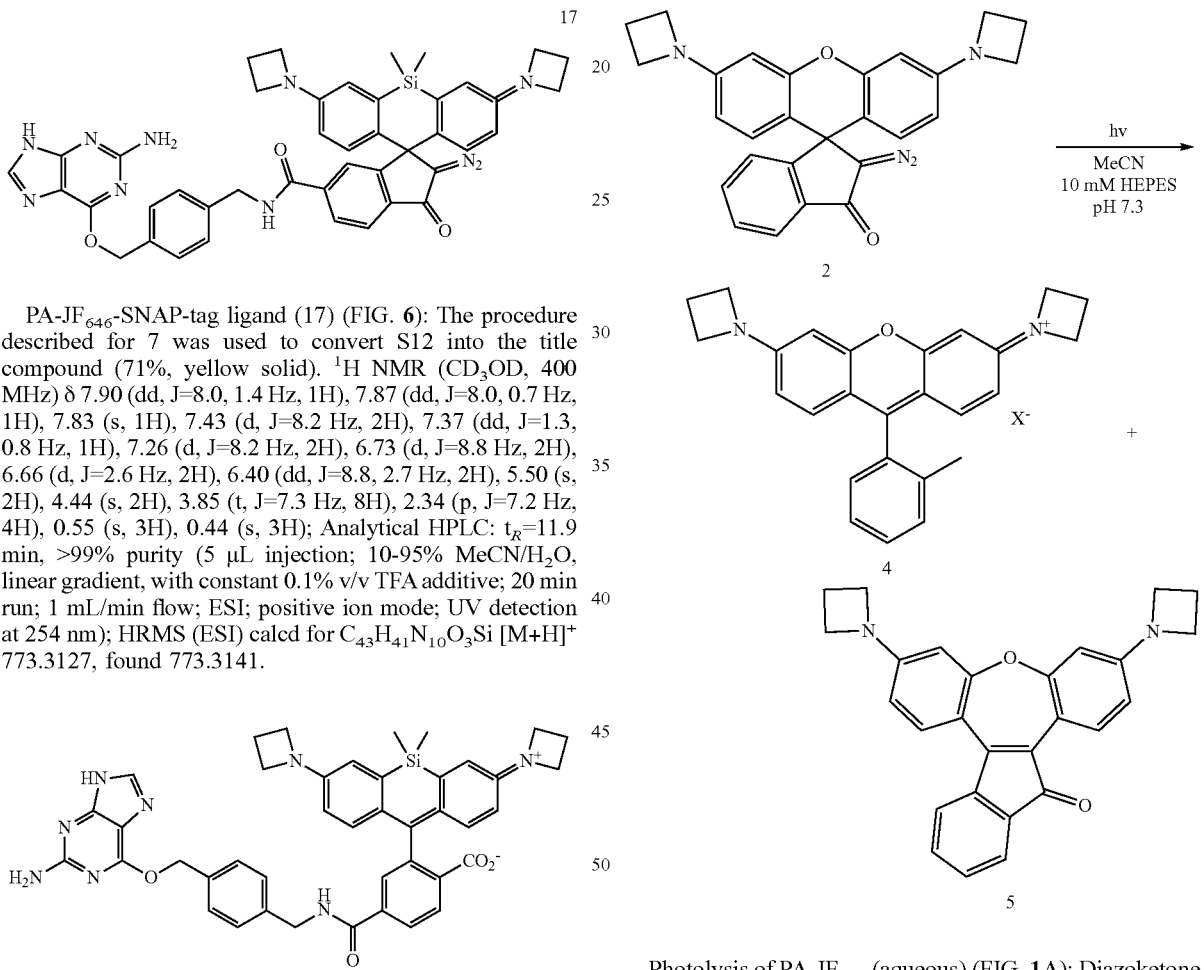

PA-JF$_{646}$-SNAP-tag ligand (17) (FIG. 6): The procedure described for 7 was used to convert S12 into the title compound (71%, yellow solid). $^1$H NMR (CD$_3$OD, 400 MHz) δ 7.90 (dd, J=8.0, 1.4 Hz, 1H), 7.87 (dd, J=8.0, 0.7 Hz, 1H), 7.83 (s, 1H), 7.43 (d, J=8.2 Hz, 2H), 7.37 (dd, J=1.3, 0.8 Hz, 1H), 7.26 (d, J=8.2 Hz, 2H), 6.73 (d, J=8.8 Hz, 2H), 6.66 (d, J=2.6 Hz, 2H), 6.40 (dd, J=8.8, 2.7 Hz, 2H), 5.50 (s, 2H), 4.44 (s, 2H), 3.85 (t, J=7.3 Hz, 8H), 2.34 (p, J=7.2 Hz, 4H), 0.55 (s, 3H), 0.44 (s, 3H); Analytical HPLC: t$_R$=11.9 min, >99% purity (5 μL injection; 10-95% MeCN/H$_2$O, linear gradient, with constant 0.1% v/v TFA additive; 20 min run; 1 mL/min flow; ESI; positive ion mode; UV detection at 254 nm); HRMS (ESI) calcd for C$_{43}$H$_{41}$N$_{10}$O$_3$Si [M+H]$^+$ 773.3127, found 773.3141.

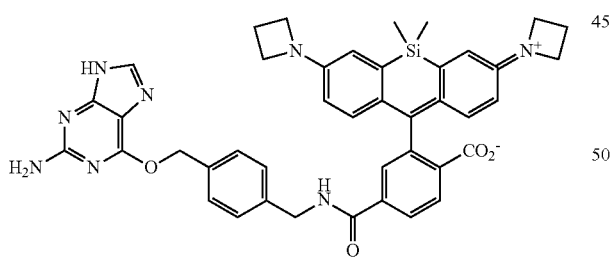

Figure 7:
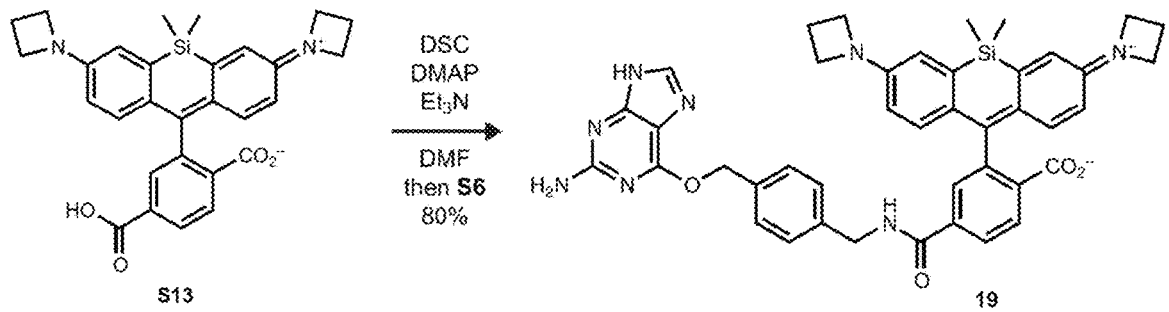
FIG. 7 shows a schematic view of the synthesis of JF$_{646}$-SNAP-tag ligand.

JF$_{646}$-SNAP-tag ligand (19) (FIG. 7): 6-Carboxy-JF$_{646}$ (S13, trifluoroacetate salt; 25 mg, 40.9 μmol) was combined with DSC (23.1 mg, 90.1 μmol, 2.2 eq) in DMF (2 mL). After adding Et$_3$N (34 μL, 246 μmol, 6 eq) and DMAP (0.5 mg, 4.09 μmol, 0.1 eq), the reaction was stirred at room temperature for 1 h while shielded from light. BG-NH$_2$ (S7, 28 mg, 102 μmol, 2.5 eq) was then added. The reaction was stirred an additional 2 h at room temperature. It was subsequently diluted with saturated NaHCO$_3$ and extracted with CH$_2$Cl$_2$ (2×). The combined organic extracts were dried over anhydrous MgSO$_4$, filtered, and concentrated in vacuo. Silica gel chromatography (0-10% MeOH/EtOAc, linear gradient) afforded 24.7 mg (80%) of 19 as a blue solid. $^1$H NMR (MeOD, 400 MHz) δ 8.02 (dd, J=8.0, 1.3 Hz, 1H), 7.99 (dd, J=8.0, 0.7 Hz, 1H), 7.82 (s, 1H), 7.67-7.64 (m, 1H), 7.46 (d, J=8.1 Hz, 2H), 7.32 (d, J=8.2 Hz, 2H), 6.73 (d, J=2.6 Hz, 2H), 6.70 (d, J=8.7 Hz, 2H), 6.32 (dd, J=8.7, 2.6 Hz, 2H), 5.51 (s, 2H), 4.52 (s, 2H), 3.87 (t, J=7.3 Hz, 8H), 2.35 (p, J=7.1 Hz, 4H), 0.58 (s, 3H), 0.51 (s, 3H); Analytical HPLC: >99% purity (4.6 mm×150 mm 5 μm C18 column; 5 μL injection; 10-95% CH$_3$CN/H$_2$O, linear gradient, with constant 0.1% v/v TFA additive; 20 min run; 1 mL/min flow; ESI; positive ion mode; UV detection at 650 nm); HRMS (ESI) calcd for C$_{42}$H$_{41}$N$_8$O$_4$Si [M+H]$^+$ 749.3015, found 749.2971.

Synthesis of Photoproducts: Preparative Photoactivation of PA-JF Probes.

Photolysis of PA-JF$_{549}$ (aqueous) (FIG. 1A): Diazoketone 2 (50 mg, 115 μmol) was taken up in MeCN (120 mL) in a quartz flask under nitrogen. Buffer (10 mM HEPES pH 7.3, 120 mL) was added, and the resulting yellow solution was sparged with nitrogen for 30 min. The reaction mixture was irradiated at room temperature with stirring for 8 h (Luzchem LZC 4V photoreactor, 365 nm lamps). It was then concentrated to dryness and deposited onto Celite. Silica gel chromatography (dry load with Celite) was performed by first eluting with 0-50% EtOAc/hexanes (linear gradient) to isolate dark product 5. Further elution with 0-15% MeOH/CH$_2$Cl$_2$ (linear gradient, with constant 1% v/v AcOH) afforded fluorescent product 4 as a dark purple solid (acetate salt, 25.3 mg, 50%). The dark product was purified again by flash chromatography (0-10% EtOAc/toluene, linear gradient) to afford 4.6 mg (9.8%) of 5 as a black solid. An analytically pure sample of 4 for spectroscopic characterization was obtained by reverse phase HPLC (10-75% MeCN/H$_2$O, linear gradient, with constant 0.1% v/v TFA).

Fluorescent product 4: (50%, dark purple solid) $^1$H NMR (CD$_3$OD, 400 MHz) δ 7.55 (td, J=7.5, 1.3 Hz, 2H), 7.51-7.42 (m, 2H), 7.22 (dd, J=7.5, 1.2 Hz, 1H), 7.11 (d, J=9.2 Hz, 2H), 6.64 (dd, J=9.2, 2.2 Hz, 2H), 6.56 (d, J=2.2 Hz, 2H), 4.38-4.27 (m, 8H), 2.57 (p, J=7.6 Hz, 4H), 2.04 (s, 3H), 1.90 (s, 3H); $^{13}$C NMR (CD$_3$OD, 101 MHz) δ 159.4 (C), 159.0 (C), 158.2 (C), 137.2 (C), 133.4 (C), 132.5 (CH), 131.8 (CH), 131.2 (CH), 130.1 (CH), 127.3 (CH), 114.7 (C), 113.8 (CH), 95.2 (CH), 52.9 (CH$_2$), 19.6 (CH$_3$), 16.8 (CH$_2$); HRMS (ESI) calcd for C$_{26}$H$_{25}$N$_2$O [M]$^+$ 381.1961, found 381.1973.

Dark product 5: (9.8%, black solid) $^1$H NMR (CDCl$_3$, 400 MHz) δ 7.78 (d, J=8.4 Hz, 1H), 7.59 (d, J=8.5 Hz, 1H), 7.55-7.50 (m, 1H), 7.41-7.37 (m, 1H), 7.34 (td, J=7.4, 1.2 Hz, 1H), 7.22 (td, J=7.3, 1.2 Hz, 1H), 6.33-6.26 (m, 4H), 3.99 (t, J=7.3 Hz, 4H), 3.92 (t, J=7.3 Hz, 4H), 2.43 (p, J=7.3 Hz, 2H), 2.38 (p, J=7.3 Hz, 2H); $^{13}$C NMR (CDCl$_3$, 101 MHz) δ 195.8 (C), 159.5 (C), 158.2 (C), 155.3 (C), 153.9 (C), 150.4 (C), 144.2 (C), 132.9 (CH), 132.8 (C), 129.8 (CH), 128.3 (CH), 127.5 (C), 122.6 (CH), 121.1 (CH), 115.7 (C), 114.8 (C), 108.5 (CH), 107.5 (CH), 104.2 (CH), 103.6 (CH), 52.4 (CH$_2$), 52.1 (CH$_2$), 16.9 (CH$_2$), 16.8 (CH$_2$); HRMS (ESI) calcd for C$_{27}$H$_{23}$N$_2$O$_2$ [M+H]$^+$ 407.1754, found 407.1772.

Photolysis of PA-JF$_{549}$ (methanol) (FIG. 8): Diazoketone 2 (75 mg, 173 μmol) was taken up in MeOH (300 mL) in a quartz flask under nitrogen, and the resulting yellow solution was sparged with nitrogen for 30 min. The reaction mixture was irradiated at room temperature with stirring for 8 h (Luzchem LZC 4V photoreactor, 365 nm lamps). It was then concentrated to dryness. Silica gel chromatography was performed by first eluting with 0-50% EtOAc/hexanes (linear gradient) to isolate dark product 5 as a black solid (14 mg, 20%). Further elution with 0-15% MeOH/CH$_2$Cl$_2$ (linear gradient, with constant 1% v/v AcOH) afforded fluorescent product S14 as a dark red-purple solid (acetate salt, 56 mg, 65%). An analytically pure sample of S14 for spectroscopic characterization was obtained by reverse phase HPLC (10-75% MeCN/H$_2$O, linear gradient, with constant 0.1% v/v TFA).

Fluorescent product S14: (65%, dark purple solid) $^1$H NMR (CD$_3$OD, 400 MHz) δ 7.68-7.52 (m, 3H), 7.29 (d, J=7.1 Hz, 1H), 7.08 (d, J=9.2 Hz, 2H), 6.63 (dd, J=9.2, 2.1 Hz, 2H), 6.54 (d, J=2.1 Hz, 2H), 4.32 (t, J=7.7 Hz, 8H), 3.42 (s, 2H), 3.35 (s, 3H), 2.57 (p, J=7.7 Hz, 4H); $^{13}$C NMR (CD$_3$OD, 101 MHz) δ 172.5 (C), 158.9 (C), 158.2 (C), 157.9 (C), 134.3 (C), 133.8 (C), 132.7 (CH), 131.4 (CH), 130.6 (CH), 128.8 (CH), 114.9 (C), 113.7 (CH), 95.2 (CH), 52.9 (CH$_2$), 52.4 (CH$_3$), 39.5 (CH$_2$), 16.8 (CH$_2$); HRMS (ESI) calcd for C$_{28}$H$_{27}$N$_2$O$_3$ [M]$^+$ 439.2016, found 439.2017.

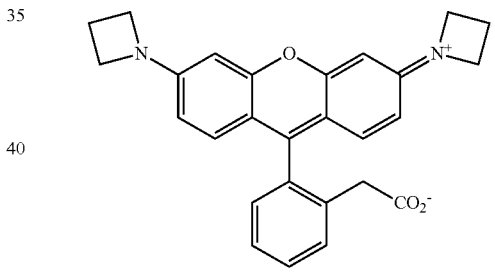

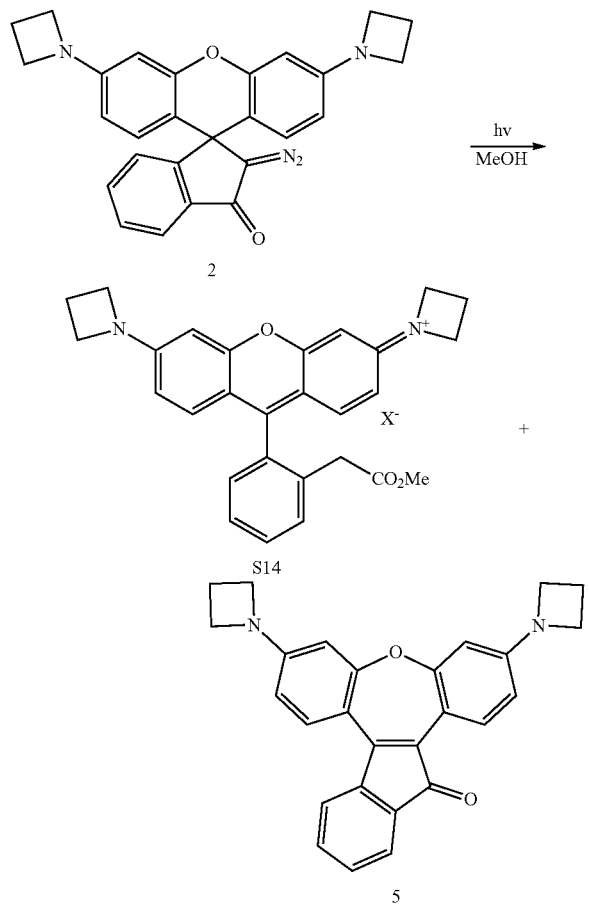

JF$_{549}$-phenylacetic acid (initial photolysis product) (3) (FIGS. 1A, 8, and 10A): Rhodamine S14 (50 mg, 100 μmol) was dissolved in MeOH (5 mL), and 1 M NaOH (1.00 mL, 1.00 mmol, 10 eq) was added. The reaction was stirred at room temperature for 18 h; it was then acidified with 2 M HCl (510 μL) and directly purified by reverse phase HPLC (10-75% MeCN/H$_2$O, linear gradient, with constant 0.1% v/v TFA) to isolate 22 mg (TFA salt, 41%) of 3 as a dark red solid. $^1$H NMR (CD$_3$OD, 400 MHz) δ 7.66-7.58 (m, 2H), 7.54 (td, J=7.3, 1.7 Hz, 1H), 7.27 (d, J=7.4 Hz, 1H), 7.11 (d, J=9.2 Hz, 2H), 6.61 (dd, J=9.2, 2.2 Hz, 2H), 6.54 (d, J=2.1 Hz, 2H), 4.32 (t, J=7.7 Hz, 8H), 3.37 (s, 2H), 2.57 (p, J=7.6 Hz, 4H); $^{13}$C NMR (CD$_3$OD, 101 MHz) δ 173.8 (C), 159.0 (C), 158.21 (C), 158.20 (C), 134.7 (C), 133.8 (C), 132.8 (CH), 132.7 (CH), 131.3 (CH), 130.5 (CH), 128.6 (CH), 115.0 (C), 113.6 (CH), 95.2 (CH), 52.9 (CH$_2$), 39.5 (CH$_2$), 16.8 (CH$_2$); HRMS (ESI) calcd for C$_{27}$H$_{25}$N$_2$O$_3$ [M+H]$^+$ 425.1860, found 425.1865.

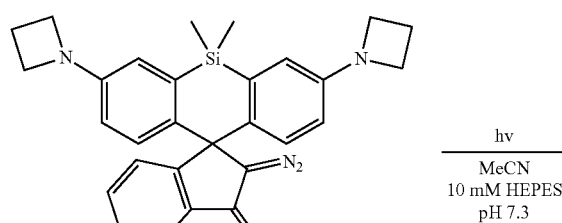

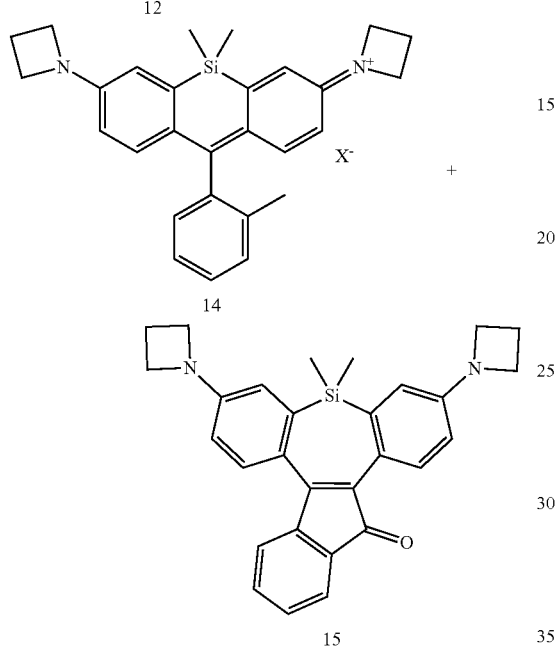

Photolysis of PA-JF$_{646}$ (aqueous) (FIG. 4A): Diazoketone 12 (25 mg, 52.5 µmol) was taken up in MeCN (60 mL) in a quartz flask under nitrogen. Buffer (10 mM HEPES pH 7.3, 60 mL) was added, and the resulting yellow solution was sparged with nitrogen for 30 min. The reaction mixture was irradiated at room temperature with stirring for 8 h (Luzchem LZC 4V photoreactor, 365 nm lamps). It was then concentrated to dryness and deposited onto Celite. Silica gel chromatography (dry load with Celite) was performed by first eluting with 0-50% EtOAc/hexanes (linear gradient) to isolate dark product 15 as a black solid (9 mg, 24%). Further elution with 0-15% MeOH/CH$_2$Cl$_2$ (linear gradient, with constant 1% v/v AcOH) afforded a small amount of fluorescent product 14 as a dark blue solid (acetate salt, 1.1 mg, 4.3%). An analytically pure sample of 14 for spectroscopic characterization was obtained by reverse phase HPLC (10-75% MeCN/H$_2$O, linear gradient, with constant 0.1% v/v TFA).

Fluorescent product 14: (4.3%, dark blue solid) $^1$H NMR (CD$_3$OD, 400 MHz) δ 7.45 (td, J=7.6, 1.2 Hz, 1H), 7.42-7.33 (m, 2H), 7.09 (d, J=7.5 Hz, 1H), 7.02 (d, J=9.4 Hz, 2H), 6.94 (d, J=2.6 Hz, 2H), 6.35 (dd, J=9.4, 2.6 Hz, 2H), 4.37 (t, J=7.5 Hz, 8H), 2.55 (p, J=7.7 Hz, 4H), 2.01 (s, 3H), 0.56 (s, 3H), 0.55 (s, 3H); $^{13}$C NMR (CD$_3$OD, 101 MHz) δ 170.3 (C), 154.6 (C), 149.0 (C), 141.9 (CH), 140.3 (C), 136.9 (C), 131.3 (CH), 130.1 (CH), 130.0 (CH), 128.4 (C), 126.8 (CH), 120.1 (CH), 113.0 (CH), 53.0 (CH$_2$), 19.4 (CH$_3$), 16.9 (CH$_2$), −1.2 (CH$_3$), −1.4 (CH$_3$); HRMS (ESI) calcd for C$_{28}$H$_{31}$N$_2$Si [M]$^+$ 423.2251, found 423.2260.

Dark product 15: (24%, black solid) $^1$H NMR (CDCl$_3$, 400 MHz) δ 7.58 (d, J=8.5 Hz, 1H), 7.56 (d, J=7.0 Hz, 1H), 7.51 (d, J=8.3 Hz, 1H), 7.34 (td, J=7.5, 1.1 Hz, 1H), 7.27-7.20 (m, 2H), 6.60 (d, J=2.5 Hz, 1H), 6.54 (d, J=2.3 Hz, 1H), 6.52 (dd, J=8.4, 2.6 Hz, 1H), 6.49 (dd, J=8.5, 2.5 Hz, 1H), 3.96 (t, J=7.3 Hz, 4H), 3.90 (t, J=7.4 Hz, 4H), 2.40 (p, J=7.3 Hz, 2H), 2.38 (p, J=7.2 Hz, 2H), 0.74 (s, 3H), 0.15 (s, 3H); $^{13}$C NMR (CDCl$_3$, 101 MHz) δ 197.4 (C), 154.0 (C), 152.5 (C), 151.6 (C), 146.5 (C), 141.4 (C), 139.7 (C), 133.1 (CH), 132.4 (C), 131.4 (CH), 131.3 (C), 128.7 (CH), 128.2 (CH), 126.1 (C), 125.3 (C), 122.7 (CH), 122.0 (CH), 114.3 (CH), 114.2 (CH), 112.2 (CH), 111.2 (CH), 52.5 (CH$_2$), 52.2 (CH$_2$), 17.1 (CH$_2$), 17.0 (CH$_2$), −3.6 (CH$_3$), −5.2 (CH$_3$); HRMS (ESI) calcd for C$_{29}$H$_{29}$N$_2$OSi [M+H]$^+$ 449.2044, found 449.2046.

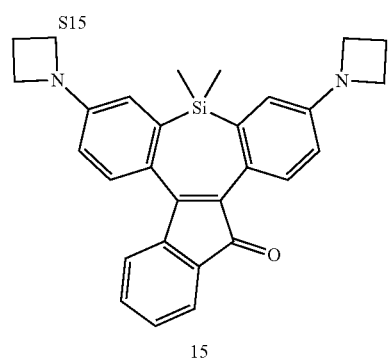

Photolysis of PA-JF$_{646}$ (methanol) (FIG. 9): Diazoketone 12 (75 mg, 157 µmol) was taken up in MeOH (300 mL) in a quartz flask under nitrogen, and the resulting yellow solution was sparged with nitrogen for 30 min. The reaction mixture was irradiated at room temperature with stirring for 3 h (Luzchem LZC 4V photoreactor, 365 nm lamps). It was then concentrated to dryness. Silica gel chromatography was performed by first eluting with 0-50% EtOAc/hexanes (linear gradient) to isolate dark product 15 as a black solid (16 mg, 23%). Further elution with 0-15% MeOH/CH$_2$Cl$_2$ (linear gradient, with constant 1% v/v AcOH) afforded fluorescent product S15 as a dark blue solid (acetate salt, 36 mg, 42%). An analytically pure sample of S15 for spectroscopic characterization was obtained by reverse phase HPLC (10-75% MeCN/H$_2$O, linear gradient, with constant 0.1% v/v TFA).

Fluorescent product S15: (42%, dark blue solid) $^1$H NMR (CD$_3$OD, 400 MHz) δ 7.57-7.45 (m, 3H), 7.17-7.13 (m, 1H), 6.97 (d, J=9.4 Hz, 2H), 6.94 (d, J=2.5 Hz, 2H), 6.33 (dd, J=9.4, 2.6 Hz, 2H), 4.37 (t, J=7.4 Hz, 8H), 3.39 (s, 2H), 3.32 (s, 3H), 2.55 (p, J=7.7 Hz, 4H), 0.58 (s, 3H), 0.54 (s, 3H); $^{13}$C NMR (CD$_3$OD, 101 MHz) δ 172.6 (C), 168.3 (C), 154.5 (C), 149.0 (C), 142.2 (CH), 140.6 (C), 133.9 (C), 132.5 (CH), 130.7 (CH), 130.2 (CH), 128.5 (C), 128.2 (CH), 120.2 (CH), 112.8 (CH), 53.1 (CH$_2$), 52.3 (CH$_3$), 39.6 (CH$_2$), 16.8 (CH$_2$), −0.9 (CH$_3$), −1.9 (CH$_3$); HRMS (ESI) calcd for C$_{30}$H$_{33}$N$_2$O$_2$Si [M]$^+$ 481.2306, found 481.2305.

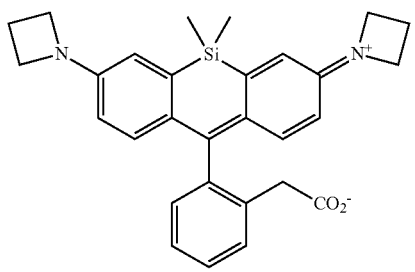

JF$_{646}$-phenylacetic acid (initial photolysis product) (13) (FIGS. 4A, 9, and 10B): Diazoketone 12 (75 mg, 157 μmol) was taken up in MeCN (294 mL) in a quartz flask under nitrogen; 2-(trimethylsilyl)ethanol (6 mL) was added, and the resulting yellow solution was sparged with nitrogen for 30 min. The reaction mixture was irradiated at room temperature with stirring for 4 h (Luzchem LZC 4V photoreactor, 365 nm lamps). It was then concentrated to dryness. Silica gel chromatography was performed by first eluting with 0-50% EtOAc/hexanes (linear gradient) to isolate dark product 15 as a black solid (16 mg, 23%). Further elution with 0-15% MeOH/CH$_2$Cl$_2$ (linear gradient, with constant 1% v/v AcOH) afforded the 2-(trimethylsilyl)ethyl ester fluorescent photoproduct S16 as a dark blue solid (acetate salt, 35 mg, 35%).

Ester photoproduct S16 (35 mg, 55.8 μmol) was dissolved in CH$_2$Cl$_2$ (3 mL), and TFA (1.5 mL) was added. After stirring the reaction at room temperature for 8 h, it was diluted with toluene (5 mL) and concentrated to dryness. The resulting residue was diluted with saturated NaHCO$_3$ and extracted with 15% i-PrOH/CHCl$_3$ (2×). The combined organic extracts with dried over anhydrous MgSO$_4$, filtered, and concentrated in vacuo. The crude product was purified by reverse phase HPLC (30-70% MeCN/H$_2$O, linear gradient, with constant 0.1% v/v TFA). Product fractions were combined, partially concentrated to remove MeCN, neutralized with saturated NaHCO$_3$, and extracted with CH$_2$Cl$_2$ (2×). The organic extracts were dried over anhydrous MgSO$_4$, filtered, and evaporated to give 10 mg (38%) of 13 as a blue solid. $^1$H NMR (CD$_3$OD, 400 MHz) δ 7.54 (d, J=7.4 Hz, 1H), 7.48 (td, J=7.6, 1.2 Hz, 1H), 7.34 (td, J=7.5, 1.1 Hz, 1H), 7.10 (d, J=9.4 Hz, 2H), 7.06-7.02 (m, 1H), 6.89 (d, J=2.5 Hz, 2H), 6.31 (dd, J=9.4, 2.5 Hz, 2H), 4.35 (t, J=7.6 Hz, 8H), 3.23 (s, 2H), 2.54 (p, J=7.7 Hz, 4H), 0.55 (s, 3H), 0.53 (s, 3H); $^{13}$C NMR (CD$_3$OD, 101 MHz) δ 170.1 (C), 154.6 (C), 148.9 (C), 142.9 (CH), 140.2 (C), 137.5 (C), 132.1 (CH), 130.0 (CH), 129.7 (CH), 129.0 (C), 126.8 (CH), 119.9 (CH), 112.8 (CH), 53.0 (CH$_2$), 43.0 (CH$_2$), 16.9 (CH$_2$), −1.2 (CH$_3$), −1.3 (CH$_3$); HRMS (ESI) calcd for C$_{29}$H$_{31}$N$_2$O$_2$Si [M+H]$^+$ 467.2149, found 467.2156.

General Experimental Information for Spectroscopy & Photochemistry

General. Fluorescent and fluorogenic molecules for spectroscopy were prepared as stock solutions in DMSO and diluted such that the DMSO concentration did not exceed 1% v/v. 10 mM HEPES buffer, pH 7.3 was prepared by dilution of a 1 M commercial stock (Fisher). Janelia Fluor 549 (JF$_{549}$) (1), JF$_{549}$-HaloTag ligand (6), JF$_{549}$-SNAP-tag ligand (10), Janelia Fluor 646 (JF$_{646}$) (11), and JF$_{646}$-HaloTag ligand (18) were available from previous work. The tetramethylrhodamine HaloTag ligand (9) was from Promega.

UV-Vis and Fluorescence Spectroscopy. Spectroscopy was performed using 1-cm path length, 3.5-mL quartz cuvettes from Starna Cells or 1-cm path length, 1.0-mL quartz microcuvettes from Hellma. All measurements were taken at ambient temperature (22±2° C.). Absorption spectra were recorded on a Cary Model 100 spectrometer (Agilent). Maximum absorption wavelength ($\lambda_{max}$) and extinction coefficient (ε) were taken in 10 mM HEPES, pH 7.3 buffer; reported values for ε are averages (n=3). Fluorescence spectra were recorded on a Cary Eclipse fluorometer (Varian); normalized spectra are shown for clarity.

Fluorescence Quantum Yield (FF) Determination. All reported quantum yield values were measured in our laboratory under identical conditions. Absolute quantum yields were measured using a Quantaurus-QY spectrometer (model C11374, Hamamatsu). This instrument uses an integrating sphere to determine photons absorbed and emitted by a sample. Measurements were carried out using dilute samples (A<0.1) and self-absorption corrections[3] were performed using the instrument software. Reported values are averages (n=3).

Figure 11A:
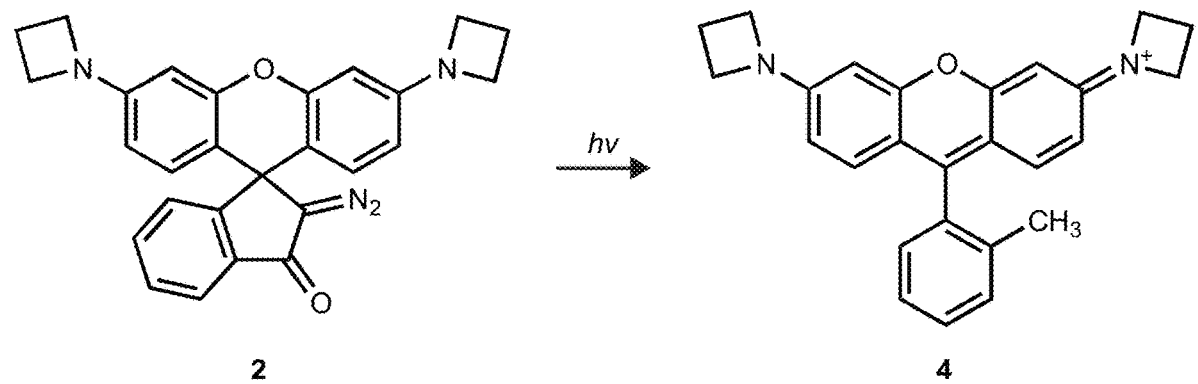
FIGS. 11A-D show photoconversion, absorbance, and HPLC peak area of various compounds. (A) Photoconversion of PA-JF$_{549}$ (2) to methyl-JF$_{549}$ (4) after photolysis (365 nm). (B) Plot of absorbance at 551 nm ($A_{551}$) vs. irradiation time (365 nm) of 2. (C) Photoconversion of JF$_{549}$-phenylacetic acid (3) to methyl-JF$_{549}$ (4) after photolysis (365 nm). (D) Plot of HPLC peak area of 4 (λ=555 nm) vs. irradiation time (365 nm) of 3.
Figure 11B:
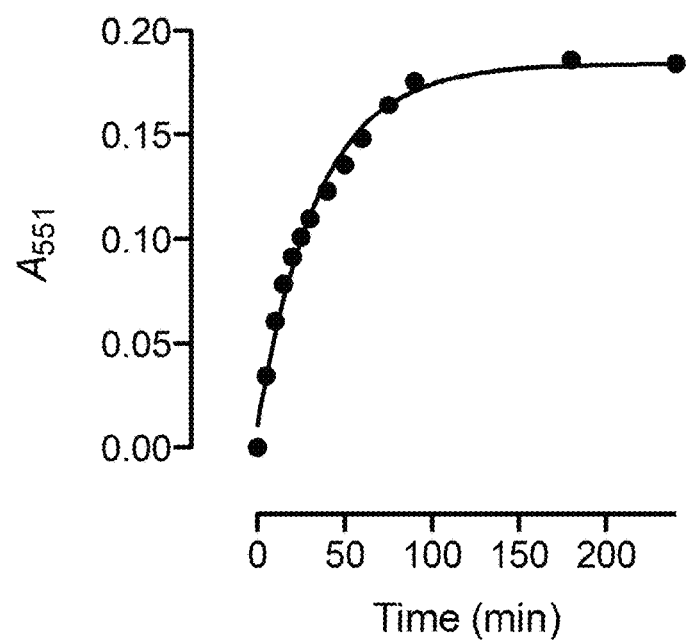
Figure 11C:
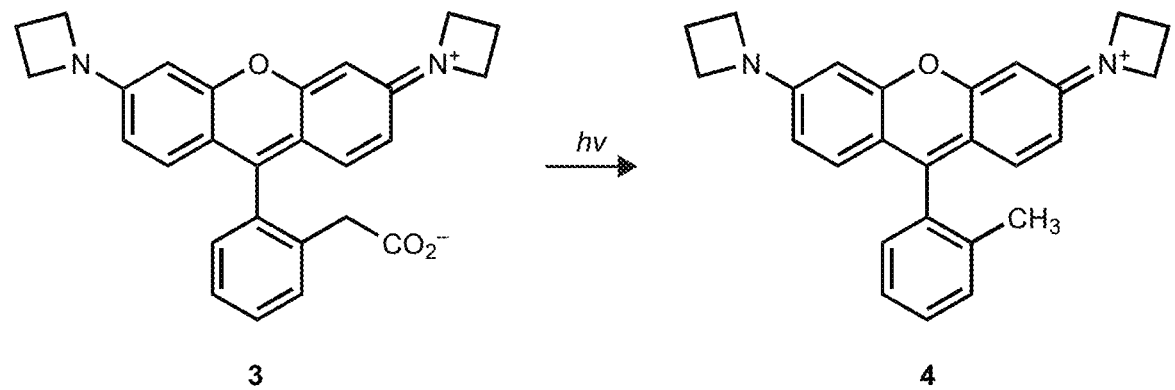
Figure 11D:
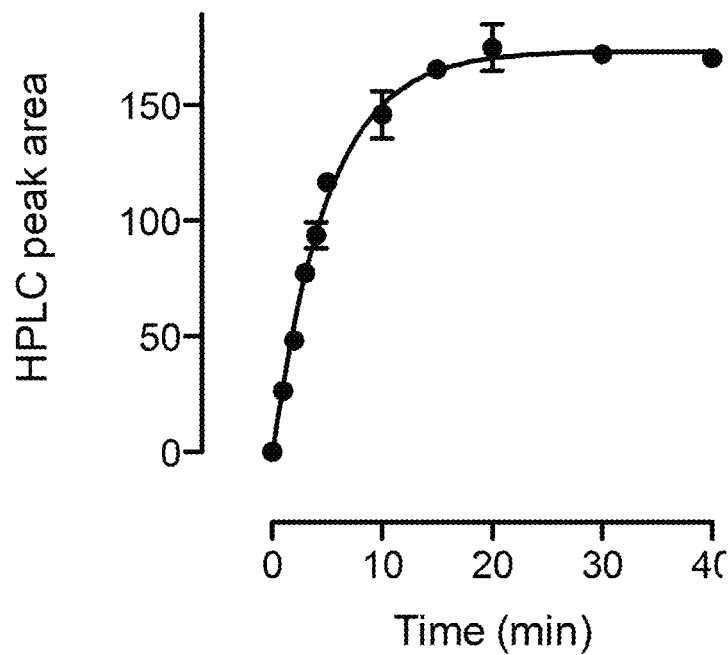

Photochemical Quantum Yield ($\Phi_{PC}$) Determination. Photochemistry was performed in 1-cm path length/3.5 mL quartz cuvettes (Starna) in a Luzchem LZC 4V photoreactor equipped with 365 nm UV lamps, a carousel, and a timer. The intensity was calibrated by potassium ferrioxalate actinometry.[4] A solution of 60 mM K$_3$Fe(C$_2$O$_4$)$_3$ was irradiated using the photoreactor setup and released Fe$^{2+}$ was determined by complexometry with 1,10 phenanthroline. Using the known photochemical quantum yield of this process ($\Phi_{PC}$=1.21), we determined the photon flux (I)=3.88×10$^{-7}$ ein/min·cm$^2$. For the conversion of PA-JF$_{549}$ (2) to methyl-JF$_{549}$ (4), samples (5 μM in 10 mM HEPES pH 7.3, 3.0 mL) were irradiated and the increase in absorbance at 551 nm was measured. For the conversion of phenylacetic acid-JF$_{549}$ (3) to methyl-JF$_{549}$ (4), the samples were irradiated and a small aliquot (50 μL) was placed in an amber glass high recovery HPLC vial. These samples were analyzed by HPLC (Agilent 1200 Analytical HPLC system equipped with autosampler and diode array detector ($\lambda_{abs}$=550 nm); Phenomenex 4.6×150 mm, 5 μm, Kinetex C18 column; 10-95% gradient of MeCN in H$_2$O containing 0.1% v/v TFA). The photochemical quantum yield ($\Phi_{PC}$, mol/ein) was determined by fitting a plot of absorbance increase or HPLC peak integral signal (5) vs. irradiation time to a one-phase association described by equation 2:

$$S_t = S_{max} - S_{max}(e^{-I\sigma\Phi_t}) \quad (2)$$

where $S_{max}$=maximal fluorescence, t=time (min), $S_t$=signal at time t, I=irradiation (ein/min·cm$^2$), and σ=decadic extinction coefficient (in units of cm$^2$/mol; 1000-fold higher than the ε value with units of M$^{-1}$ cm$^{-1}$ based on cuvette geometry). For the conversion of compound 2 to compound 4, it was determined that $\Phi_{PC}$=2.2% (FIGS. 11A-B). For the photoinduced decarboxylation of 3 to generate 4, it was found that $\Phi_{PC}=15\%$ (FIGS. 11C-D).

Photochemistry of HaloTag Ligands 6 and 16 in the presence and absence of HaloTag Protein. HaloTag protein was a generous gift from Adam Berro and Eric Schreiter (Janelia Research Campus, HHMI) and was used as a 100 μM solution in 75 mM NaCl, 50 mM TRIS·HCl, pH 7.4 with 20% v/v glycerol (TBS-glycerol). Absorbance measurements were performed in 1 mL quartz cuvettes. HaloTag ligands 6 and 16 (5 μM) were dissolved in 10 mM HEPES, pH 7.3 containing 0.1 mg·mL$^{-1}$ CHAPS. An aliquot of HaloTag protein (1.5 equiv) or an equivalent volume of TBS-glycerol blank was added and the resulting mixture was incubated for 1 h at room temperature while protected from light. The initial absorbance was recorded and the samples were irradiated at room temperature in a photoreactor (Luzchem LZC 4V, 365 nm lamps). Absorbance scans were taken at t=5, 10, 15, 20, 25, 30, 40, 50, and 60 min, after which additional irradiation elicited no additional absorbance increases.

Photochemistry of SNAP-tag Ligands 7 and 17 in the Presence and Absence of SNAP-tag protein. SNAP-tag protein (SNAPf-6×His) was a generous gift from Eric Schreiter (Janelia Research Campus, HEM) and was used as a 2.8 mg·mL$^{-1}$ (142 μM) solution in 1×PBS with 1 mM DTT. Absorbance measurements were performed in 1 mL quartz cuvettes. SNAP-tag ligands 7 and 17 (5 μM) were dissolved in 10 mM HEPES, pH 7.3 containing 0.1 mg·mL$^{-1}$ CHAPS. An aliquot of SNAP-tag protein (1.5 equiv) or an equivalent volume of buffer was added and the resulting mixture was incubated for 18 h at 4° C. while protected from light. The initial absorbance was recorded and the samples were irradiated at room temperature in a photoreactor (Luzchem LZC 4V, 365 nm lamps). Absorbance scans were taken at t=5, 10, 15, 20, 25, 30, and 60 min, after which additional irradiation elicited no additional absorbance increases.

Results and Discussion of PA-JF Dye Photochemistry

Figure 10A:
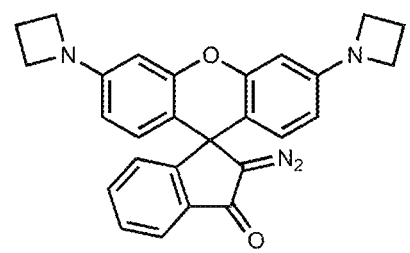
FIGS. 10A-B show chemical structures and absorbance spectra of PA-JF$_{549}$ and PA-JF$_{646}$. (A) Chemical structures and absolute absorbance spectra of PA-JF$_{549}$ (2) and photoproducts 3-5. (B) Chemical structures and absolute absorbance specta of PA-JF$_{646}$ (12) and photoproducts 13-15. All spectra were taken at 5 µM in 10 mM HEPES, pH 7.3.
Figure 10A:
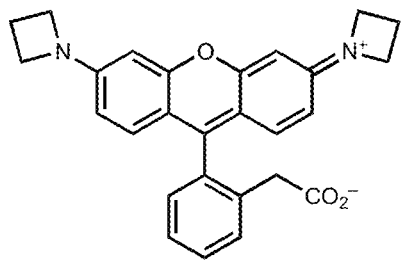
Figure 10A:
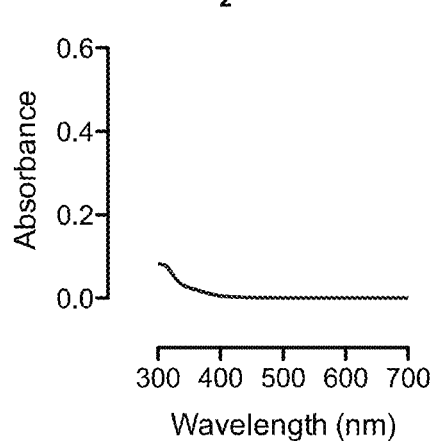
Figure 10A:
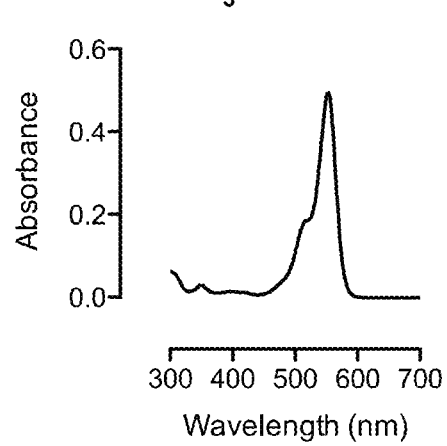
Figure 10A:
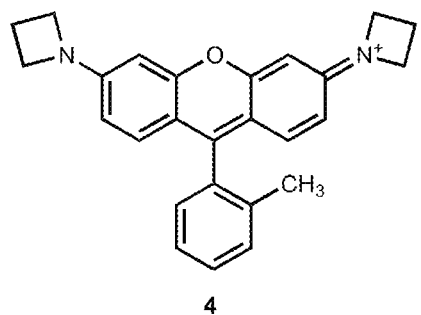
Figure 10A:
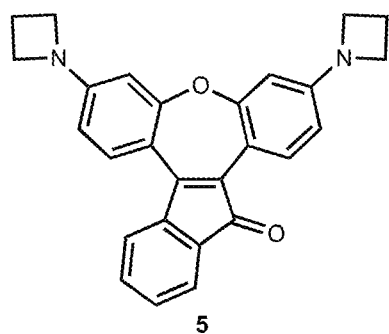
Figure 10A:
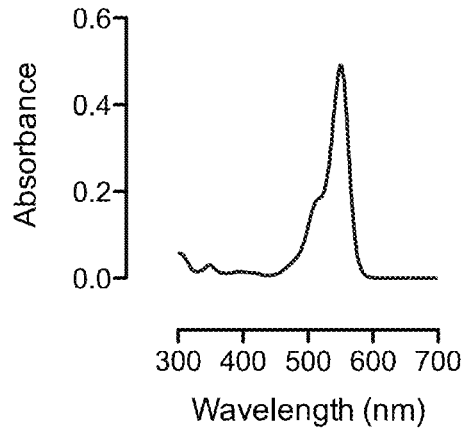
Figure 10A:
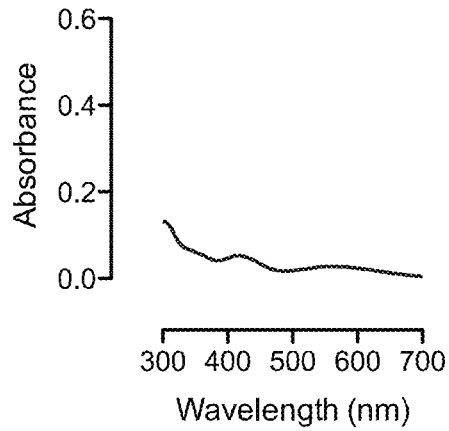

To test the compatibility of the diazoketone caging strategy with the bright, azetidine-containing Janelia Fluor dyes, JF$_{549}$ (1)[1] was first treated with oxalyl chloride, TEA, and then TMS-diazomethane to give the desired photoactivatable JF$_{549}$ (PA-JF$_{549}$) (2) in 70% yield (FIG. 1A). In contrast to the strong visible absorption of JF$_{549}$ (FIG. 1B), PA-JF$_{549}$ showed low absorption in the visible (FIG. 10A). The photochemistry of this molecule was then explored in the presence of water (1:1 v/v MeCN:10 mM HEPES pH 7.3); previous experiments had examined this photochemistry exclusively in methanol.[4,5] The addition of MeCN cosolvent was necessary to perform this reaction on a preparative scale due to the modest solubility of 2 in water. Based on previous reports two major products were expected, the phenylacetic acid derivative 3 and the indanone "dark product" 5. Surprisingly, the major photoproduct (50%) was not the expected phenylacetic acid derivative 3, but rather the methyl-JF$_{549}$ (4) (FIG. 1A), which also shows similar spectral properties to the parent 1 (FIG. 1B, FIG. 10A, and Table 3). This result was confirmed without the MeCN cosolvent in dilute aqueous samples (10 mM HEPES pH 7.3 containing 0.1% v/v DMSO) where the methyl-JF$_{549}$ (4) was also observed as the major product by LC-MS (data not shown). This compound results from photoinduced decarboxylation of the initial photochemical product 3. Only trace amounts of 3 were observed throughout the course of the photochemical reaction (data not shown), suggesting that the decarboxylation was faster than the initial photochemical rearrangement. A small (10%) amount of the "dark product" S16 was also isolated, which exhibits a low but broad absorption profile (FIG. 10A). The efficiency of uncaging for 2 was then quantified through determination of the photochemical quantum yield of this process (see Photochemical Quantum Yield $\Phi_{PC}$ Determination). For the conversion of 2 to 4, it was found that $\Phi_{PC}=2.2\%$ (FIG. 11A-B).

TABLE 3

Spectral properties of PA-JF$_{549}$ and PA-JF$_{646}$ photoproducts.

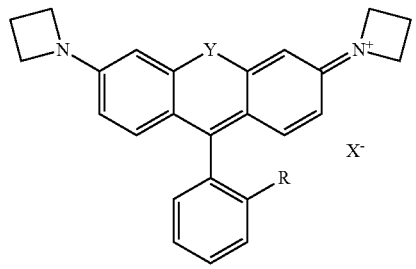

| compound | Y | R | X$^-$ | $\lambda_{max}$ (nm) | $\lambda_{ex}$ (nm) | $\lambda_{em}$ (nm) | ε (M$^{-1}$cm$^{-1}$) | Φ |
|---|---|---|---|---|---|---|---|---|
| JF$_{549}$ (1) | O | CO$_2^-$ | —[a] | 549 | 549 | 571 | 101,000 | 0.88 |
| S14 | O | CH$_2$CO$_2$CH$_3$ | CF$_3$CO$_2^-$ | 557 | 558 | 580 | 93,300 | 0.80 |
| 3 | O | CH$_2$CO$_2$H | CF$_3$CO$_2^-$ | 553 | 553 | 573 | 98,900 | 0.85 |
| 4 | O | CH$_3$ | CF$_3$CO$_2^-$ | 551 | 551 | 570 | 85,900 | 0.78 |
| JF$_{646}$ (11) | Si(CH$_3$)$_2$ | CO$_2^-$ | —[a] | 646 | 646 | 664 | (148,000)[b] | 0.54 |
| S15 | Si(CH$_3$)$_2$ | CH$_2$CO$_2$CH$_3$ | CF$_3$CO$_2^-$ | 655 (656)[b] | 655 (657) | 670 (670) | 120,000 (148,000) | 0.47 |
| 13 | Si(CH$_3$)$_2$ | CH$_2$CO$_2^-$ | —[a] | 651 (655) | 651 (655) | 665 (669) | 120,000 (162,000) | 0.53 |
| 14 | Si(CH$_3$)$_2$ | CH$_3$ | CF$_3$CO$_2^-$ | 649 (653) | 649 (653) | 663 (666) | 118,000 (154,000) | 0.47 |

[a]Compound isolated as the inner salt.
[b]Parentheses indicate properties in EtOH w/0.1% v/v TFA.

Figure 8:
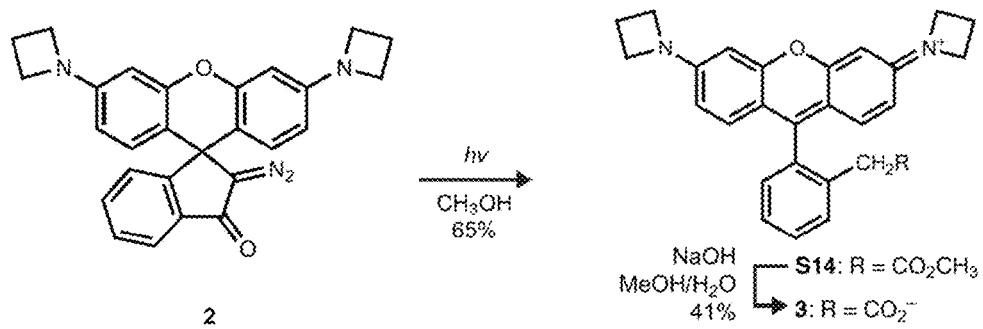
FIG. 8 shows a schematic view of the synthesis of PA-JF$_{549}$ photoproducts.

In order to confirm that the methyl-JF$_{549}$ product 4 results from photoinduced decarboxylation of the putative initial photochemical product 3, we independently synthesized 3 in a stepwise manner from 2 (FIG. 8). Photolysis of 2 in methanol generated the expected[5,6] methyl phenylacetate S14, which was then saponified to provide JF$_{549}$-phenylacetic acid 3. This fluorophore displays spectral properties similar to those of the parent JF$_{549}$ (FIG. 1B, Table 3). Irradiation of 3 with 365 nm light achieved rapid conversion to 4, the same product obtained from photolysis of 2 in aqueous solution (FIGS. 11C-D). Importantly, samples of 3 in the same buffer (10 mM HEPES pH 7.3) showed no appreciable conversion to 4 when aged in the dark. From the plot in FIG. 11D, it was determined that the photochemical quantum yield of the decarboxylation was $\Phi_{PC}$=15%. The nearly 7-fold higher photochemical quantum yield of the decarboxylation relative to the initial uncaging of 2 (2.2%) was consistent with the negligible amounts of 3 observed during the photolysis of 2.

Figure 10B:
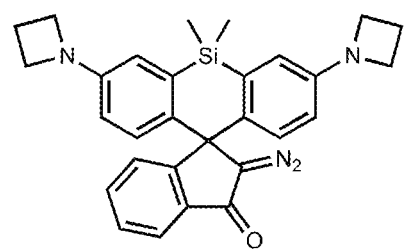
Figure 10B:
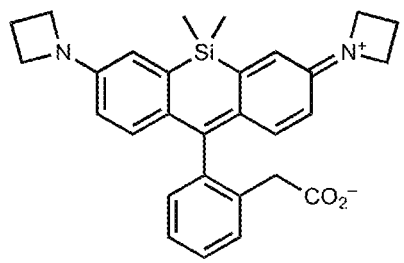
Figure 10B:
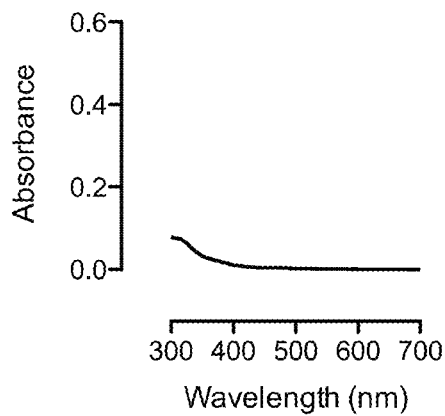
Figure 10B:
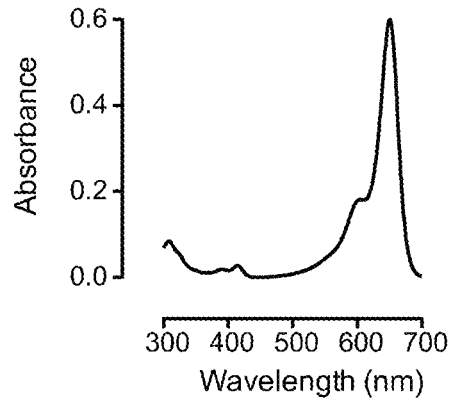
Figure 10B:
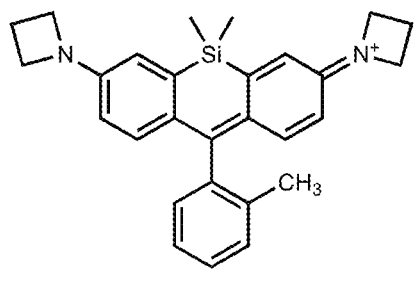
Figure 10B:
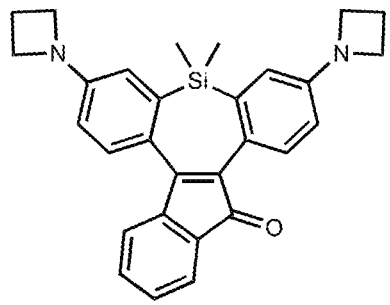
Figure 10B:
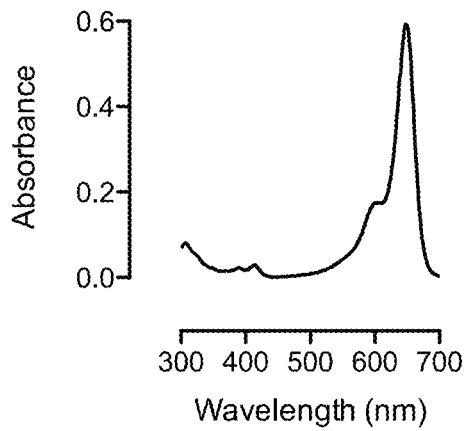
Figure 10B:
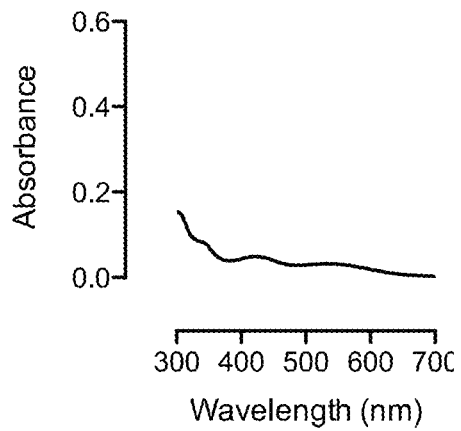

The same caging strategy was then applied to azetidinyl Si-rhodamine JF$_{646}$ (11). Rhodamine 11 was converted to diazoketone 12 (PA-JF$_{646}$) in reasonable yield (37%) through the same TMS-diazomethane protocol used previously (FIG. 4A). As was observed for PA-JF$_{549}$ (2), PA-JF$_{646}$ displayed minimal absorption in the visible region (FIG. 10B). When irradiated in aqueous solution (1:1 v/v MeCN: 10 mM HEPES pH 7.3), however, 12 provided only a small amount of fluorescent photoproduct 14 (~4%). We observed low levels of phenylacetic acid 13 during the reaction—which largely disappeared as the reaction was pushed to completion—and the most significant isolated product was indanone 15 (24%). Similar results were seen in the absence of MeCN (i.e., dilute aqueous samples analyzed by LC-MS).

Because the expected initial photoproduct 13 could not be isolated and characterized via photolysis of PA-JF$_{646}$, we sought to separately synthesize this compound via a route (FIG. 9) similar to the preparation of 3. Unlike the photolysis of 12 in aqueous solution, performing the same reaction in methanol provided methyl phenylacetate photoproduct S15 in moderate (42%) yield. However, attempts to hydrolyze the methyl ester under a variety of conditions (NaOH, LiOH, etc.) were unsuccessful, yielding only starting material or decomposition. Instead, we performed photolysis of 12 in MeCN containing 2% v/v 2-(trimethylsilyl)ethanol to generate the 2-(trimethylsilyl)ethyl ester photoproduct S16 (35% yield). This ester was successfully deprotected with TFA/CH$_2$Cl$_2$ to isolate the desired phenylacetic acid 13. As shown in Table 3, the PA-JF$_{646}$ photoproducts 14 and S15, as well as the expected initial photoproduct 13, all displayed excellent brightness and spectra similar to those of JF$_{646}$ (FIG. 10B). It was difficult to predict which photoproduct (13 or 14) would predominate under the finer illumination conditions of more complex imaging experiments like PALM, but the comparatively good spectral properties of both species confirmed that, in either case, a bright fluorophore would result. Although photolysis of free PA-JF$_{646}$ provided only a small amount of fluorescent photoproduct in aqueous solution, we anticipated (vide infra) that protein conjugates of this probe (e.g., HaloTag, SNAP-tag) would display improved photochemical behavior.

Figure 5:
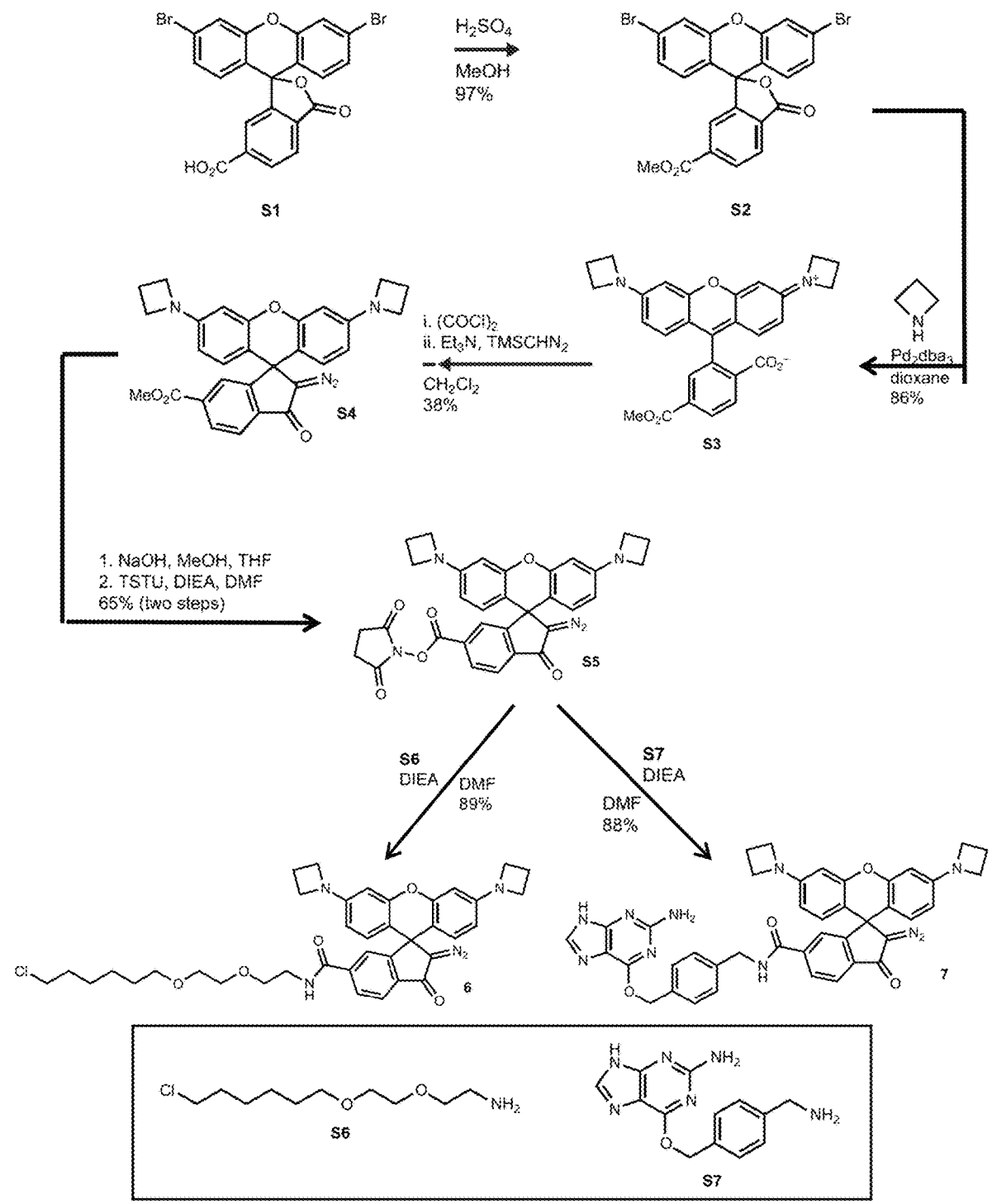
FIG. 5 shows a schematic view of the synthesis of PA-JF$_{549}$ derivatives.
Figure 6:
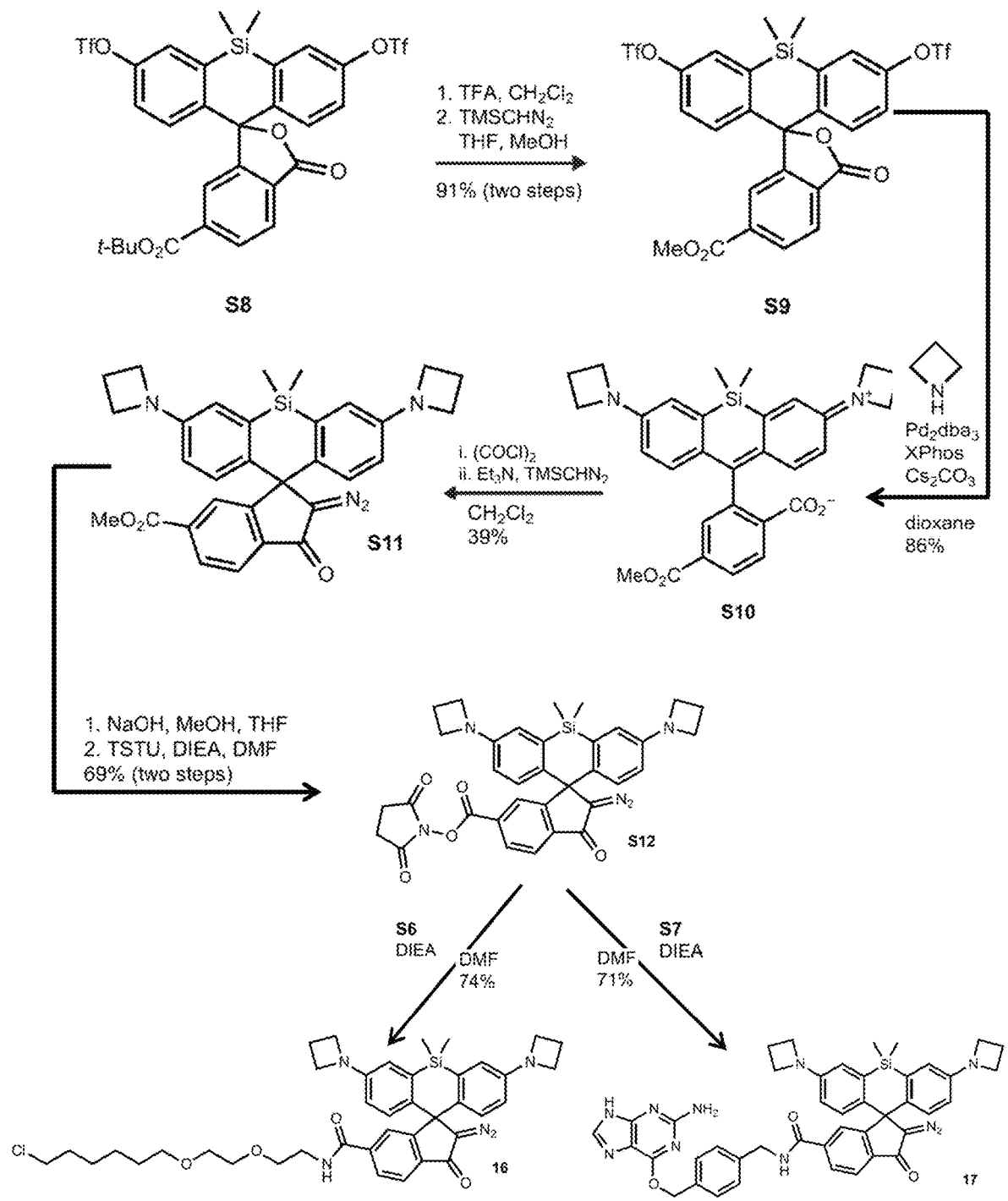
FIG. 6 shows a schematic view of the synthesis of PA-JF$_{646}$ derivatives.

To investigate the impact of protein conjugation on the uncaging reaction and evaluate the performance of PA-JF$_{549}$ and PA-JF$_{646}$ for cellular imaging, we synthesized the HaloTag (6, 16) and SNAP-tag (7, 17) ligands of these compounds (FIGS. 5 and 6). The azetidine rings were installed through C—N cross-coupling of dibromofluoran S2 or silafluorescein ditriflate S9. Treatment with oxalyl chloride followed by TMS-diazomethane yielded diazoketones S4 and S11. Hydrolysis of the methyl esters at the 6-position was followed by amide coupling to the HaloTag (S6) and SNAP-tag (S7) ligand fragments to provide the four desired labels: PA-JF$_{549}$-HaloTag ligand (6), PA-JF$_{549}$-SNAP-tag ligand (7), PA-JF$_{646}$-HaloTag ligand (16), and PA-JF$_{646}$-SNAP-tag ligand (17).

The photochemistry of the ligands was then evaluated in the presence or absence of the cognate protein (HaloTag or SNAP-tag) to test how conjugation to a protein affects photochemical outcome. To begin, PA-JF$_{549}$-HaloTag ligand (6) was incubated with excess HaloTag protein (1 h) and then exhaustively photolyzed with 365 nm light (FIG. 3A). The conjugate exhibited low visible absorption prior to photolysis but showed a substantial increase in absorption at ~550 nm after photolysis with 365 nm light (absorbance spectra were recorded at regular intervals from 5-60 min of irradiation time). The absorbance of the photoconverted conjugate of 6 ("6+HaloTag+hv," FIG. 3C) was similar in intensity to that of the traditional, non-photoactivatable JF$_{549}$-HaloTag ("8+HaloTag," FIGS. 3B and 3C). When ligand 6 was photoactivated in the absence of HaloTag protein, we observed a substantially reduced absorption at 550 nm (FIG. 1C). Comparing these results, it was found that conjugation to the HaloTag protein resulted in a nearly two-fold increase in the amount of product absorbing at 550 nm. This demonstrated that conjugation to a protein can increase the photochemical efficiency and partitioning to the desired fluorescent product. This may result from a conformational bias or restriction imposed on the dye by the enzyme, which could disfavor the pathway towards the planar dark product 5 and prevent its formation. When the same experiments were performed with PA-JF$_{549}$-SNAP-tag ligand (7), a similar result was seen (FIGS. 3D and 3F). Photolysis of the SNAP-tag conjugate of 7 ("7+SNAP-tag+hv") resulted in a 1.6-fold increase in the amount of fluorescent product when compared to the photoactivation of unbound 7; the absorbance spectrum for the standard JF$_{549}$-SNAP-tag ("10+SNAP-tag," FIGS. 3E and 3F) is shown for comparison.

The improved behavior of PA-JF$_{549}$ on enzyme encouraged us to pursue the PA-JF$_{646}$ ligands despite the poor photochemical behavior of free PA-JF$_{646}$ (vide supra). The PA-JF$_{646}$-HaloTag ligand (16) was incubated with HaloTag enzyme and photoactivated with 365 nm light. Low absorbance of the HaloTag conjugate prior to photolysis yet a substantial increase in far-red (~650 nm) absorbing species upon illumination with UV light (FIG. 4C) was also observed. Comparison of the photochemistry of 16 in the presence ("16+HaloTag+hv") and absence ("16+hv") of the HaloTag protein revealed that conjugation of the protein improves the generation of the far-red absorbing compound by nearly five-fold (FIG. 4D), suggesting that the desired photochemical outcome is enhanced when this PA-JF ligand is attached to protein. A significant improvement in photochemical outcome upon binding to protein was also seen for PA-JF$_{646}$-SNAP-tag ligand (17), although the magnitude of the effect (2.4-fold) was not as large (FIG. 4E). The absorbance spectra of the photoactivated conjugates ("16+HaloTag+hv" and "17+SNAP-tag+hv") also compare favorably to the conjugates of the non-photoactivatable ligands 18 (JF$_{646}$-HaloTag ligand) (FIGS. 4B and D) and 19 (JF$_{646}$-SNAP-tag ligand) (FIGS. 4B and 4E). For each PA-JF ligand, we also estimated the photoconversion efficiency to fluorescent product by comparison of the post-activation absorbance to the absorbance of the corresponding free methyl-JF photoproduct (methyl-JF$_{549}$ 4 or methyl-JF$_{646}$ 14) (Tables 3-4). For the conjugates of HaloTag ligands 6 and 16, we estimated conversions of 90% (PA-JF$_{549}$-HaloTag) and 76% (PA-JF$_{646}$-HaloTag). The efficiencies for the SNAP-tag conjugates of 7 and 17 were found to be somewhat lower, with estimated fluorescent product yields of 45% (PA-JF$_{549}$-SNAP-tag) and 39% (PA-JF$_{646}$-SNAP-tag). Nonetheless, all of these values are far greater than the photoconversion efficiencies measured for free PA-JF$_{549}$ (2, 50%) and PA-JF$_{646}$ (12, 4%).

TABLE 4

Photoconversion efficiency of free dyes PA-JF$_{549}$ and PA-JF$_{646}$ and the HaloTag and SNAP-tag ligands when bound to protein.

| starting material | product | % conversion |
| --- | --- | --- |
| | | 50%[a] |
| | | 4%[a] |
| | | 90%[b] |
| | | 76%[b] |

TABLE 4-continued

Photoconversion efficiency of free dyes PA-JF$_{549}$ and PA-JF$_{646}$ and the HaloTag and SNAP-tag ligands when bound to protein.

| starting material | product | % conversion |
|---|---|---|
| [structure] | [structure] | 45%[b] |
| [structure] | [structure] | 39%[b] |

[a]Measured by isolation of photoproducts.
[b]Estimated by absorbance relative to free methyl-substituted due.

The results of this example demonstrate that the Janelia Fluor dyes can be rendered photoactivatable using the diazoketone strategy. Activation of PA-JF$_{549}$ and PA-JF$_{646}$ yield unexpected fluorescent products, the methyl-JF$_{549}$ (4) and methyl-JF$_{646}$ (14), which maintain the brightness of the parent compounds. More importantly, it was shown that conjugation to a protein can influence the photochemical outcome of the reaction towards the desirable fluorescent form. Conjugation of PA-JF$_{549}$ HaloTag ligand (6) to the cognate HaloTag protein increases the yield of visible-absorbing product, and the conjugate has similar absorptivity to the conjugate with standard JF$_{549}$-HaloTag ligand (FIG. 3C). Similarly, the PA-JF$_{646}$ HaloTag ligand (16) shows a substantial five-fold increase in the far-red-absorbing product when attached to the HaloTag protein (FIG. 4D). The generality of this effect was confirmed with the SNAP-tag ligands of these probes (7, 17), which also demonstrate improved fluorescent product yield when photoactivated on protein. Overall, these results validate the utility of the PA-JF dyes, especially in the context of protein conjugates.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1 Lavis, L. D. & Raines, R. T. Bright ideas for chemical biology. *ACS Chem. Biol.* 3, 142-155 (2008).
2 Lavis, L. D. & Raines, R. T. Bright building blocks for chemical biology. *ACS Chem. Biol.* 9, 855-866 (2014).
3 Keppler, A. et al. A general method for the covalent labeling of fusion proteins with small molecules in vivo. *Nat. Biotechnol.* 21, 86-89 (2002).
4 Xue, L., Karpenko, I. A., Hiblot, J. & Johnsson, K. Imaging and manipulating proteins in live cells through covalent labeling. *Nat. Chem. Biol.* 11, 917-923 (2015).
5 Grimm, J. B. et al. A general method to improve fluorophores for live-cell and single-molecule microscopy. *Nat. Methods* 12, 244-250 (2015).

6 Grimm, J. B. et al. Carbofluoresceins and carborhodamines as scaffolds for high-contrast fluorogenic probes. *ACS Chem. Biol.* 8, 1303-1310 (2013).

7 Grimm, J. B. et al. Synthesis of a far-red photoactivatable Si-rhodamine for super resolution microscopy. *Angew. Chem. Int. Ed.* 55, 1723-1727 (2016).

8 Belov, V. N. et al. Masked rhodamine dyes of five principal colors revealed by photolysis of a 2-diazo-1-indanone caging group: Synthesis, photophysics, and light microscopy applications. *Chem. Eur. J.* 20, 13162-13173 (2014).

9 Habuchi, S., Tsutsui, H., Kochaniak, A. B., Miyawaki, A. & Van Oijen, A. M. mKikGR, a monomeric photoswitchable fluorescent protein. *PloS one* 3, e3944 (2008).

10 Epling, G. A. & Lopes, A. Fragmentation pathways in the photolysis of phenylacetic acid. *J. Am. Chem. Soc.* 99, 2700-2704 (1977).

11 Los, G. V. et al. HaloTag: A novel protein labeling technology for cell imaging and protein analysis. *ACS Chem. Biol.* 3, 373-382 (2008).

12 Zhang, M. et al. Rational design of true monomeric and bright photoactivatable fluorescent proteins. *Nat. Methods* 9, 727-729 (2012).

13 Wang, S., Moffitt, J. R., Dempsey, G. T., Xie, X. S. & Zhuang, X. Characterization and development of photoactivatable fluorescent proteins for single-molecule-based superresolution imaging. *Proc. Natl. Acad. Sci. USA* 111, 8452-8457 (2014).

14 Manley, S. et al. High-density mapping of single-molecule trajectories with photoactivated localization microscopy. *Nat. Methods* 5, 155-157 (2008).

15 Abrahamsson, S. et al. Fast multicolor 3D imaging using aberration-corrected multifocus microscopy. *Nat. Methods* 10, 60-63 (2013).

16 Betzig, E. et al. Imaging intracellular fluorescent proteins at nanometer resolution. *Science* 313, 1642-1645 (2006).

17 Legant, W. R. et al. High-density three-dimensional localization microscopy across large volumes. *Nat. Methods* 13, 359-365 (2016).

18 Lee, H. D. et al. Superresolution imaging of targeted proteins in fixed and living cells using photoactivatable organic fluorophores. *J Am. Chem. Soc.* 132, 1642-1645 (2010).

19 Banala, S., Maurel, D., Manley, S. & Johnsson, K. A caged, localizable rhodamine for superresolution microscopy. *ACS Chem. Biol.* 7, 289-293 (2011).

20 Li, L. et al. Real-time imaging of Huntingtin aggregates diverting target search and gene transcription. *eLife* 5, e17056 (2016).

21 English, B. P. & Singer, R. H. A three-camera imaging microscope for high-speed single-molecule tracking and super-resolution imaging in living cells. Proc. SPIE 9550 Biosensing and Nanomedicine VIII, 955008 (2015).

22 Halstead, J. M. et al. An RNA biosensor for imaging the first round of translation from single cells to living animals. *Science* 347, 1367-1671 (2015).

23 Preibisch, S., Saalfeld, S., Schindelin, J. & Tomancak, P. Software for bead-based registration of selective plane illumination microscopy data. *Nat. Methods* 7, 418-419 (2010).

24 Dedecker, P., Duwe, S., Neely, R. K. & Zhang, J. Localizer: Fast, accurate, open-source, and modular software package for superresolution microscopy. *J. Biomed. Opt.* 17, 126008 (2012).

25 Katz, Z. B. et al. Mapping translation 'hot-spots' in live cells by tracking single molecules of mRNA and ribosomes. *eLife* 5 (2016).

26 Vallotton, P. & Olivier, S. Tri-track: Free software for large-scale particle tracking. *Microsc. Microanal.* 19, 451-460 (2013).

27 Mortensen, K. I., Churchman, L. S., Spudich, J. A. & Flyvbjerg, H. Optimized localization analysis for single-molecule tracking and super-resolution microscopy. *Nat. Methods* 7, 377-381 (2010).

28 Lionnet, T. et al. A transgenic mouse for in vivo detection of endogenous labeled mRNA. *Nat. Methods* 8, 165-170 (2011).

29 Grimm, J. B., English, B. P., Chen, J. et al., *Nat. Methods* 12, 244-250 (2015).

30 Woodroofe, C. C., Lim, M. H., Bu, W. M. et al., *Tetrahedron* 61, 3097-3105 (2005).

31 Suzuki, K., Kobayashi, A., Kaneko, S. et al., *Phys. Chem. Chem. Phys.* 11, 9850-9860 (2009).

32 Belov, V. N., Wurm, C. A., Boyarskiy, V. P. et al., *Angew. Chem. Int. Ed.* 49, 3520-3523 (2010).

33 Belov, V. N., Mitronova, G. Y., Bossi, M. L. et al., *Chem. Eur. J.* 20, 13162-13173 (2014).

34 Epling, G. A. and Lopes, A., *J. Am. Chem. Soc.* 99, 2700-2704 (1977).

35 Budac, D. and Wan, P., *J. Photochem. Photobiol. A* 67, 135-166 (1992).

36 Los, G. V., Encell, L. P., Mcdougall, M. G. et al., *ACS Chem. Biol.* 3, 373-382 (2008).

36 Hatchard, C. and Parker, C., *Proc. R. Soc. A* 235, 518-536 (1956).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound of the formula:

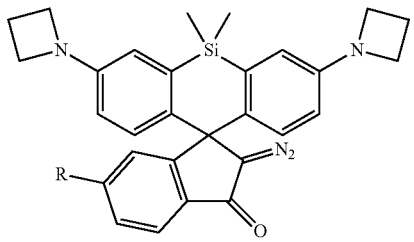

wherein R is selected from the group consisting of a ligand that is a protein tag, and N-hydroxysuccinimide (NHS) ester.

2. A photoactive complex, comprising the compound according to claim 1 wherein R is the ligand, conjugated to a protein that binds the ligand.

3. The photoactive complex of claim 2, wherein the compound is conjugated to the protein in vivo.

4. The compound of claim 1, wherein the ligand is selected from the group consisting of:
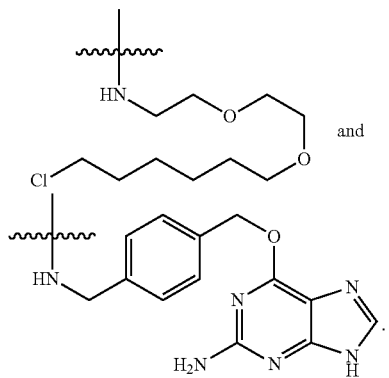
and
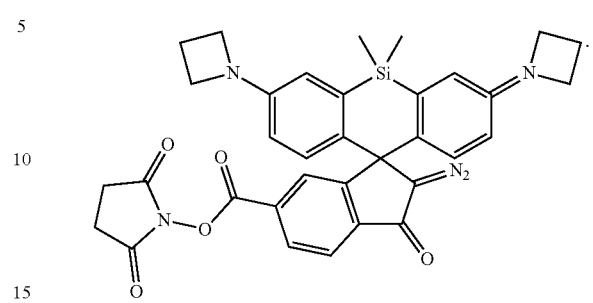
5. The compound of claim 1, of the formula:
6. The compound of claim 1, of the formula:
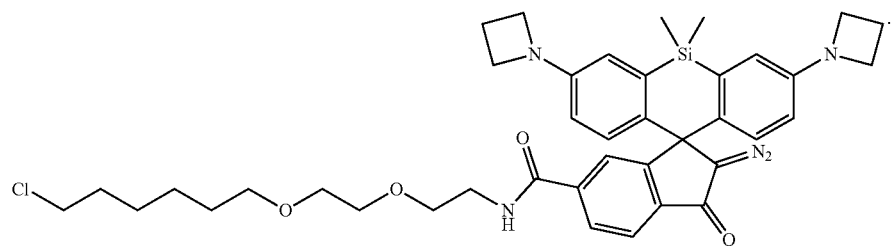
7. The compound of claim 1, of the formula:
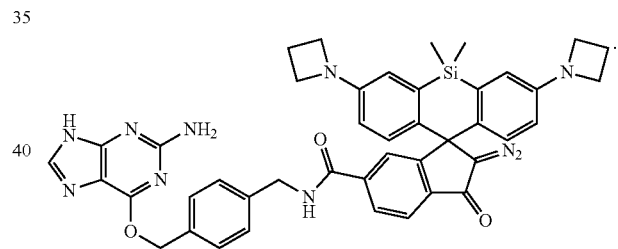
* * * * *